(12) United States Patent
Mukasa et al.

(10) Patent No.: US 11,311,249 B2
(45) Date of Patent: Apr. 26, 2022

(54) INFORMATION PROCESSING APPARATUS, INFORMATION PROCESSING METHOD, NON-TRANSITORY COMPUTER-READABLE MEDIUM, AND INFORMATION PROCESSING SYSTEM FOR DISPLAYING BIOLOGICAL SIGNAL MEASUREMENTS

(71) Applicants: Shinya Mukasa, Shizuoka (JP); Hideaki Yamagata, Kanagawa (JP); Noriyuki Tomita, Ishikawa (JP); Aritaka Hagiwara, Ishikawa (JP); Yutaka Yagiura, Kanagawa (JP); Daisuke Sakai, Tokyo (JP)

(72) Inventors: Shinya Mukasa, Shizuoka (JP); Hideaki Yamagata, Kanagawa (JP); Noriyuki Tomita, Ishikawa (JP); Aritaka Hagiwara, Ishikawa (JP); Yutaka Yagiura, Kanagawa (JP); Daisuke Sakai, Tokyo (JP)

(73) Assignee: Ricoh Company, Ltd., Tokyo (JP)

(*) Notice: Subject to any disclaimer, the term of this patent is extended or adjusted under 35 U.S.C. 154(b) by 23 days.

(21) Appl. No.: 16/290,095

(22) Filed: Mar. 1, 2019

(65) Prior Publication Data
US 2019/0274640 A1    Sep. 12, 2019

(30) Foreign Application Priority Data

Mar. 12, 2018  (JP) ............................ JP2018-044701
Dec. 10, 2018  (JP) ............................ JP2018-231110

(51) Int. Cl.
*A61B 5/00* (2006.01)
*G06F 3/0488* (2013.01)
(Continued)

(52) U.S. Cl.
CPC ............ *A61B 5/7445* (2013.01); *A61B 5/245* (2021.01); *A61B 5/7425* (2013.01);
(Continued)

(58) Field of Classification Search
CPC . A61B 5/04008; A61B 5/0476; A61B 5/7425; A61B 5/743; A61B 5/7435;
(Continued)

(56) References Cited

U.S. PATENT DOCUMENTS

| | | | |
|---|---|---|---|
| 8,478,393 B2* | 7/2013 | Ramanathan | A61B 5/044 600/523 |
| 2004/0051721 A1* | 3/2004 | Ramseth | G06F 19/00 345/689 |

(Continued)

FOREIGN PATENT DOCUMENTS

| | | |
|---|---|---|
| JP | 04-337868 | 11/1992 |
| JP | 2007-193399 | 8/2007 |

(Continued)

*Primary Examiner* — Tan H Tran
(74) *Attorney, Agent, or Firm* — Harness, Dickey & Pierce, P.L.C.

(57) ABSTRACT

An information processing apparatus includes an acquiring unit, a determining unit, and a changing unit. The acquiring unit is configured to acquire determination information for determining a display layout of a screen for displaying information related to one or more biological signals. The determining unit is configured to determine a display layout corresponding to the determination information acquired by the acquiring unit. The changing unit is configured to change a display layout of the screen in accordance with the display layout determined by the determining unit.

20 Claims, 47 Drawing Sheets

(51) Int. Cl.
*G06F 3/04886* (2022.01)
*A61B 5/245* (2021.01)
*G06F 9/451* (2018.01)
*G06F 3/04842* (2022.01)
*G06F 3/04845* (2022.01)

(52) U.S. Cl.
CPC ...... *G06F 3/04842* (2013.01); *G06F 3/04845* (2013.01); *G06F 3/04886* (2013.01); *G06F 9/451* (2018.02)

(58) Field of Classification Search
CPC ....... A61B 5/7445; A61B 5/245; A61B 5/369; G06F 2203/04806; G06F 3/04845; G06F 3/04886; G06F 9/451; G06F 3/04842
See application file for complete search history.

(56) References Cited

U.S. PATENT DOCUMENTS

| | | | |
|---|---|---|---|
| 2007/0168231 A1 | 7/2007 | Sasai | |
| 2010/0298718 A1* | 11/2010 | Gilham | H04W 16/10 600/484 |
| 2011/0105854 A1* | 5/2011 | Kiani | G16H 40/63 600/300 |
| 2012/0101396 A1* | 4/2012 | Solosko | A61B 5/0432 600/509 |
| 2012/0278099 A1* | 11/2012 | Kelly | G16H 10/60 705/3 |
| 2013/0129198 A1* | 5/2013 | Sherman | G06F 19/321 382/159 |
| 2015/0091778 A1* | 4/2015 | Day | G16H 40/63 345/1.3 |
| 2015/0160821 A1* | 6/2015 | Cho | G06F 3/0482 715/769 |
| 2015/0227702 A1* | 8/2015 | Krishna | A61B 5/7257 705/2 |
| 2016/0000382 A1* | 1/2016 | Jain | A61B 5/04012 600/545 |
| 2017/0017764 A1* | 1/2017 | Tsugo | G16H 40/63 |
| 2017/0168295 A1 | 6/2017 | Iwami | |
| 2018/0268588 A1 | 9/2018 | Shinohara et al. | |
| 2019/0059769 A1* | 2/2019 | Nenadovic | A61B 5/7253 |

FOREIGN PATENT DOCUMENTS

| | | |
|---|---|---|
| JP | 4228352 | 12/2008 |
| JP | 2015-000175 | 1/2015 |
| JP | 2017-107057 | 6/2017 |
| JP | 2018-089336 | 6/2018 |

* cited by examiner

Annotation List

☑ Show Markup on wave ——————— 180a

| No. | File | Time | Event | MEMO | Cluster |
|---|---|---|---|---|---|
| 2 ☐ | 001 | 00:09:30 | 🔥 | normal spike | B |
| 1 ☐ | 001 | 00:05:00 | 🔥 | strong spike | A |
| 0 ☐ | 000 | 00:00:00 | 🔥 | Dr.memo | A |

Exit Measurement

180

<ANALYSIS SCREEN>

LAYOUT TABLE  1001

| MEDICAL EXAMINATION RESULT | LAYOUT CONTENT |
|---|---|
| AFFECTED AREA IS PRESENT IN LEFT BRAIN | ENLARGE MAGNETOENCEPHALOGRAPHY SIGNAL WAVEFORM OF LEFT BRAIN AND REDUCE MAGNETOENCEPHALOGRAPHY SIGNAL WAVEFORM OF RIGHT BRAIN |
| AFFECTED AREA IS PRESENT IN RIGHT BRAIN | ENLARGE MAGNETOENCEPHALOGRAPHY SIGNAL WAVEFORM OF RIGHT BRAIN AND REDUCE MAGNETOENCEPHALOGRAPHY SIGNAL WAVEFORM OF LEFT BRAIN |
| THERE IS ABNORMALITY IN BRAIN WAVES | ENLARGE ELECTROENCEPHALOGRAPHY SIGNAL WAVEFORM |
| ... | ... |

FIG.32
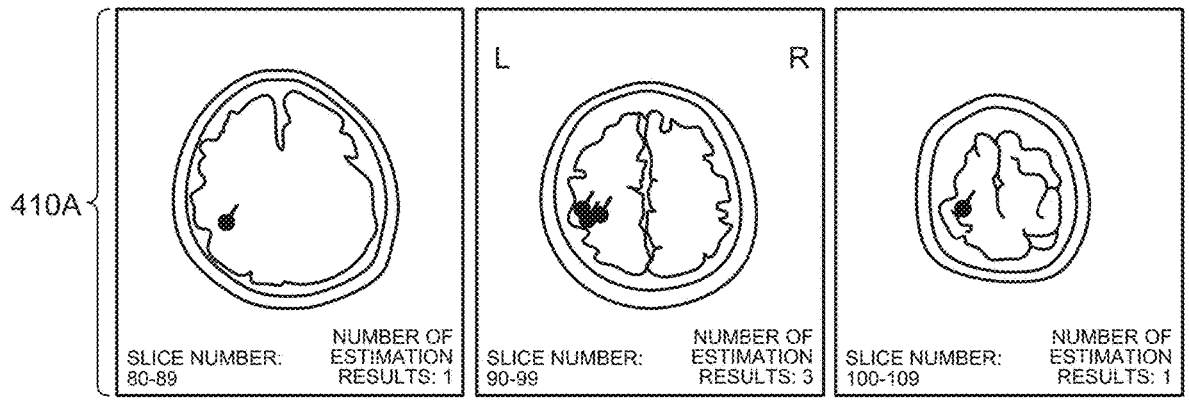
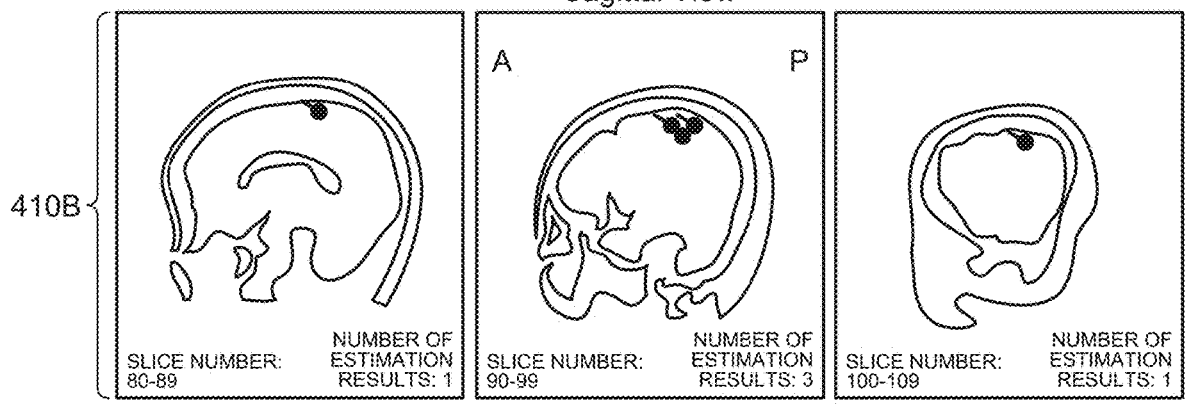
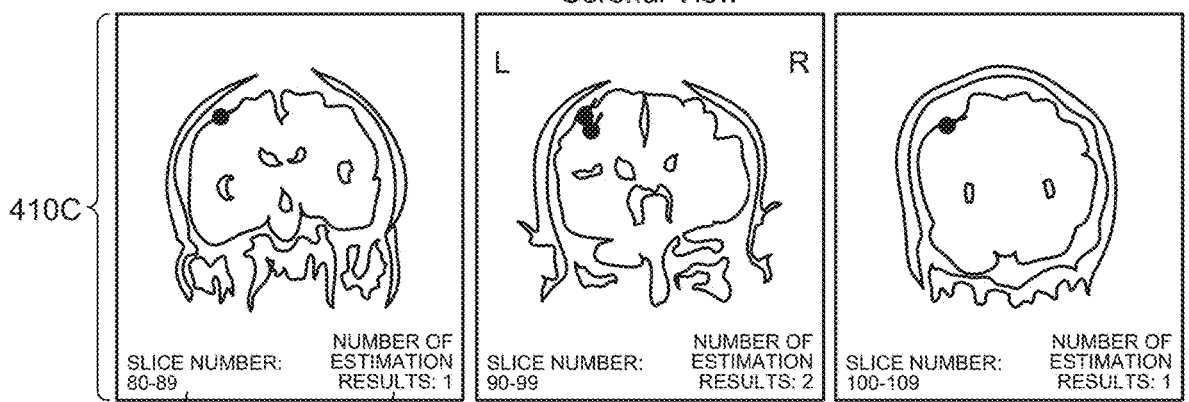

FIG.33
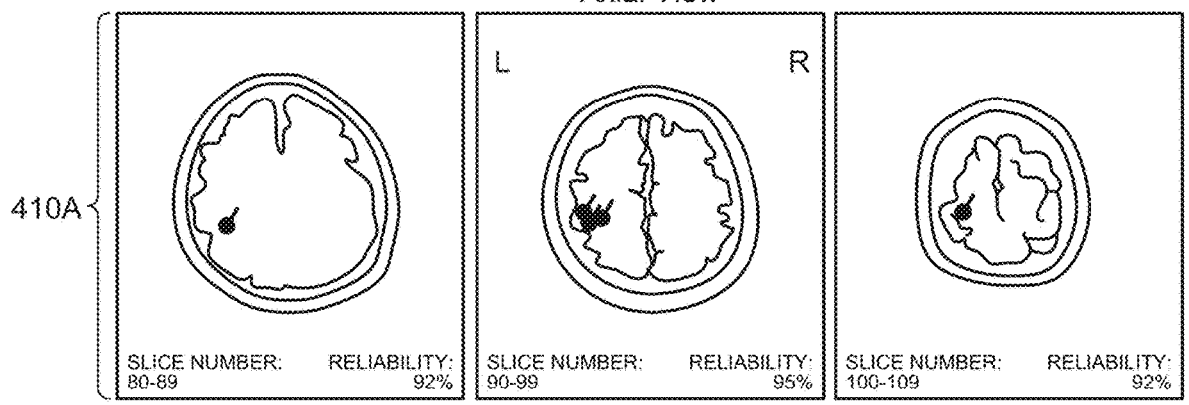
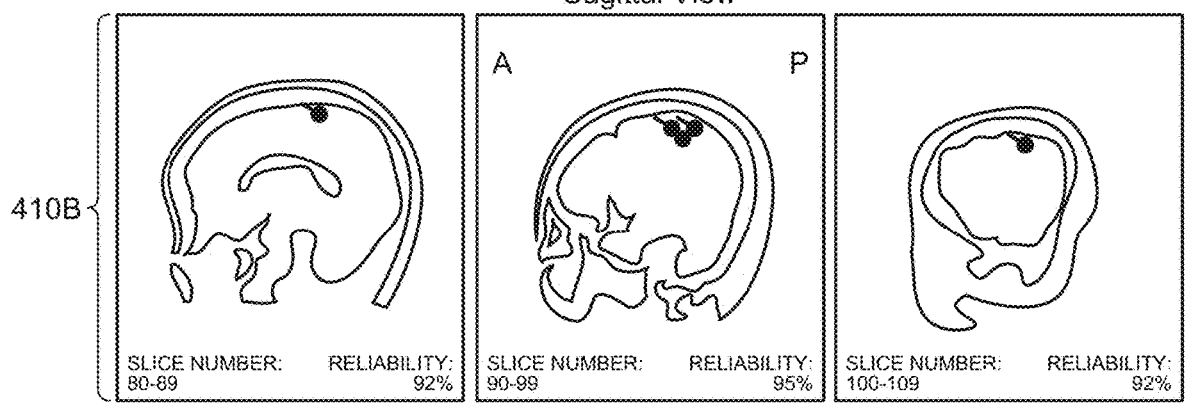
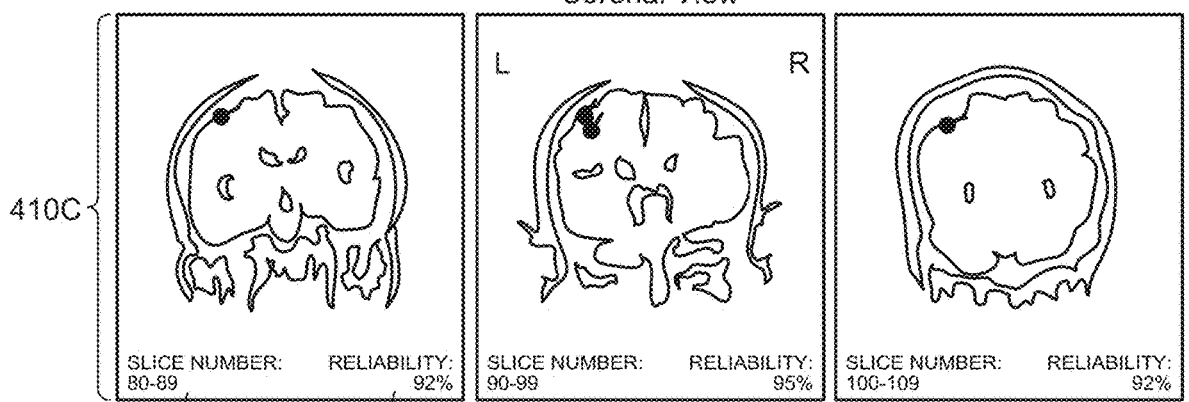

FIG.34

| MEDICAL EXAMINATION RESULT | LAYOUT CONTENT OF ANALYSIS SCREEN | LAYOUT CONTENT OF MERGE SCREEN |
|---|---|---|
| AFFECTED AREA IS PRESENT IN LEFT BRAIN | ENLARGE MAGNETOENCEPHALOGRAPHY SIGNAL WAVEFORM OF LEFT BRAIN AND REDUCE MAGNETOENCEPHALOGRAPHY SIGNAL WAVEFORM OF RIGHT BRAIN | DISPLAY SLICES OF LEFT BRAIN AND HIDE SLICES OF RIGHT BRAIN |
| AFFECTED AREA IS PRESENT IN RIGHT BRAIN | ENLARGE MAGNETOENCEPHALOGRAPHY SIGNAL WAVEFORM OF RIGHT BRAIN AND REDUCE MAGNETOENCEPHALOGRAPHY SIGNAL WAVEFORM OF LEFT BRAIN | DISPLAY SLICES OF RIGHT BRAIN AND HIDE SLICES OF LEFT BRAIN |
| THERE IS ABNORMALITY IN BRAIN WAVES | ENLARGE ELECTROENCEPHALOGRAPHY SIGNAL WAVEFORM | DISPLAY SLICES OF LEFT BRAIN AND RIGHT BRAIN |
| ... | ... | ... |

LAYOUT TABLE
1002

| SOURCE ESTIMATION STATE | LAYOUT CONTENT |
|---|---|
| TEN OR MORE SIGNAL SOURCES ARE ESTIMATED | ENLARGE MRI TOMOGRAPHY IMAGE |
| LESS THAN TEN SIGNAL SOURCES ARE ESTIMATED | DISPLAY MRI TOMOGRAPHY IMAGE IN NORMAL SIZE |
| ... | ... |

FIG.46

LAYOUT TABLE 1003

| CHANNEL, ETC. SELECTION STATE | LAYOUT CONTENT |
|---|---|
| SELECT CHANNEL GROUP (L) | DISPLAY WAVEFORM OF MONTAGE PATTERN CORRESPONDING TO CHANNEL GROUP (L) |
| SELECT CHANNEL GROUP (R) | DISPLAY WAVEFORM OF MONTAGE PATTERN CORRESPONDING TO CHANNEL GROUP (R) |
| SELECT CHANGE OF MONTAGE PATTERN | ENLARGE ELECTROENCEPHALOGRAPHY SIGNAL WAVEFORM |
| ... | ... |

FIG.49

LAYOUT TABLE 1004

| ROLL INFORMATION | LAYOUT CONTENT |
|---|---|
| BRAIN SURGEON | ENLARGE MRI TOMOGRAPHY IMAGE |
| EPILEPSY DOCTOR | ENLARGE WAVELENGTH AND HIDE MRI TOMOGRAPHY IMAGE |
| ... | ... |

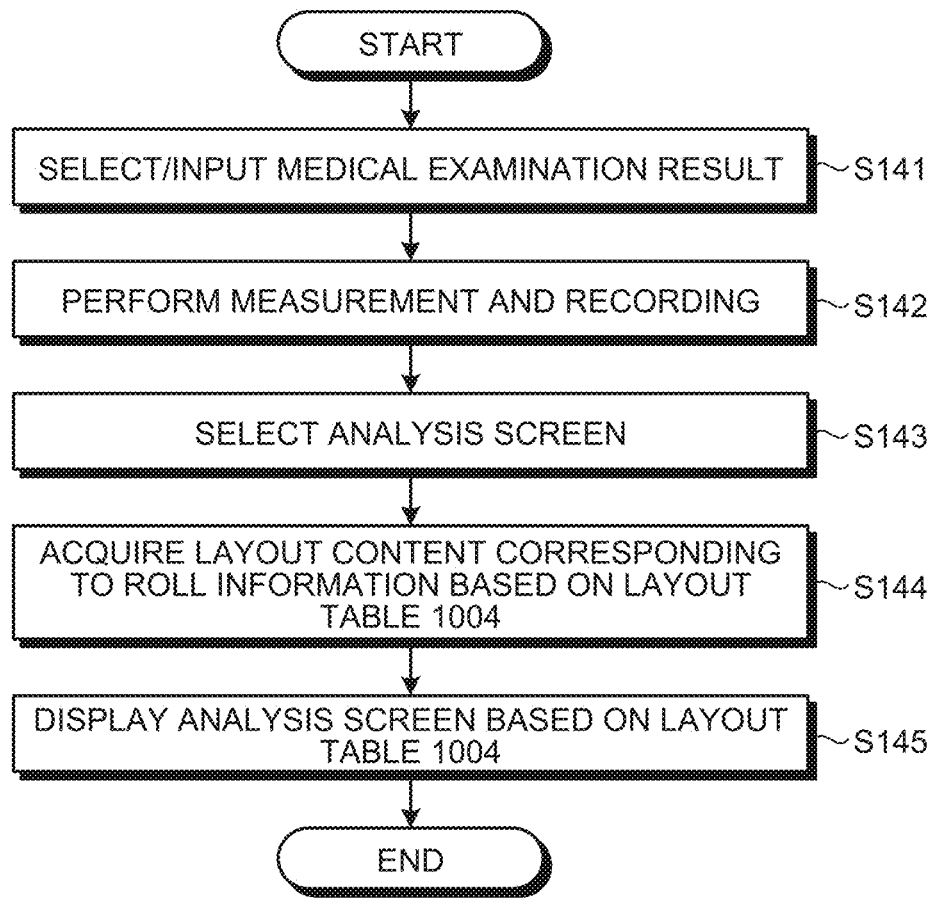

INFORMATION PROCESSING APPARATUS, INFORMATION PROCESSING METHOD, NON-TRANSITORY COMPUTER-READABLE MEDIUM, AND INFORMATION PROCESSING SYSTEM FOR DISPLAYING BIOLOGICAL SIGNAL MEASUREMENTS

CROSS-REFERENCE TO RELATED APPLICATIONS

The present application claims priority under 35 U.S.C. § 119 to Japanese Patent Application No. 2018-44701, filed on Mar. 12, 2018 and Japanese Patent Application No. 2018-231110 filed in Japan on Dec. 10, 2018. The contents of which are incorporated herein by reference in their entirety.

BACKGROUND OF THE INVENTION

1. Field of the Invention

The present invention relates to an information processing apparatus, an information processing method, a computer-readable medium, and a biological signal measurement system.

2. Description of the Related Art

In a magnetoencephalograph and an electroencephalograph for measuring brain neural activity, a system for distinguishing a waveform portion (hereinafter, referred to as a singularity) unique to epilepsy from measured waveforms, estimating a signal source from the singularity, displaying the waveforms, and displaying the signal source on a tomography image in a superimposed manner has been known. Further, a portion to be resected at operation (a portion that causes epilepsy) is identified on the basis of the position of the signal source on the tomography image.

When information measured by the magnetoencephalograph and the electroencephalograph as described above is to be displayed, it is often the case that a type of information and a type of mode of displaying the information are substantially determined depending on symptoms in a patient or depending on qualification, preference, etc. of a person (doctor or the like) who performs analysis. As a system that displays medical information as described above, a system that registers related items based on heuristics used by a doctor and displays related information in accordance with selection made by a user has been disclosed (see Japanese Unexamined Patent Application Publication No. 2007-193399).

However, the technique described in Japanese Unexamined Patent Application Publication No. 2007-193399 is to make it easy to select data to be displayed, rather than to change a data display mode to an optimal mode or a preferable mode. Therefore, it takes time and effort to generate an appropriate layout for displaying data.

SUMMARY OF THE INVENTION

According to one aspect of the present invention, an information processing apparatus includes an acquiring unit, a determining unit, and a changing unit. The acquiring unit is configured to acquire determination information for determining a display layout of a screen for displaying information related to one or more biological signals. The determining unit is configured to determine a display layout corresponding to the determination information acquired by the acquiring unit. The changing unit is configured to change a display layout of the screen in accordance with the display layout determined by the determining unit.

BRIEF DESCRIPTION OF THE DRAWINGS

FIG. 7 is an enlarged view of a left-side region of the measurement recording screen;

FIG. 10 is a diagram illustrating an updated annotation list;

FIG. 18 is a diagram illustrating an example in which a display region of one of magnetoencephalography signal waveforms in the analysis screen of the first embodiment is enlarged;

FIG. 19 is a diagram illustrating an example of a layout table of the first embodiment;

FIG. 32 is a diagram illustrating still another example of the screen that is displayed when the merge button is pressed;

FIG. 33 is a diagram illustrating still another example of the screen that is displayed when the merge button is pressed;

FIG. 34 is a diagram illustrating another example of the layout table of the first embodiment;

FIG. 42 is a diagram illustrating an example of a layout table of the second embodiment;

FIG. 46 is a diagram illustrating an example in which an electroencephalography signal waveform is enlarged in an analysis screen according to a third embodiment;

FIG. 49 is a diagram illustrating an example of a layout table of a fourth embodiment; and FIG. 50 is a flowchart illustrating operation of changing a layout of an analysis screen.

The accompanying drawings are intended to depict exemplary embodiments of the present invention and should not be interpreted to limit the scope thereof. Identical or similar reference numerals designate identical or similar components throughout the various drawings.

DESCRIPTION OF THE EMBODIMENTS

Figure 1:
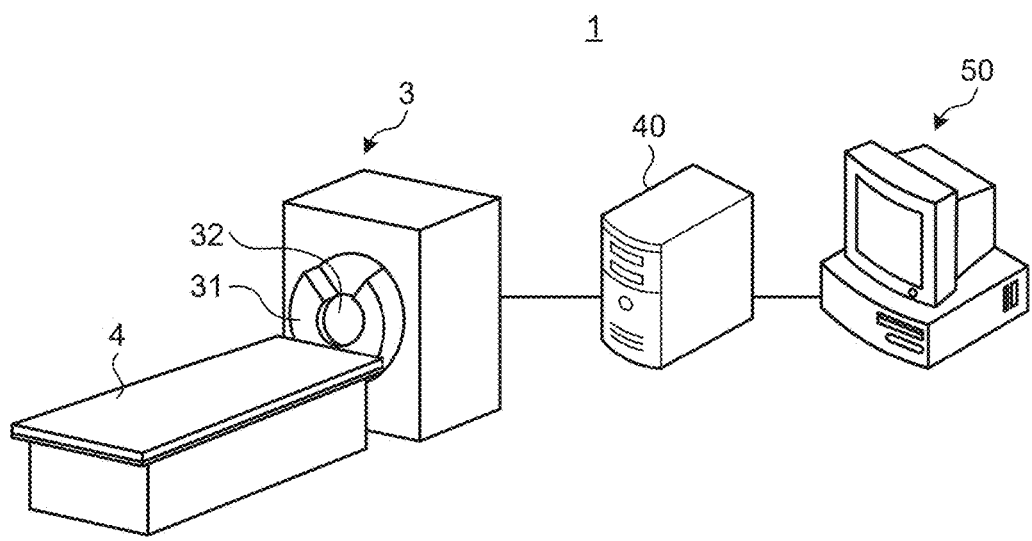
FIG. 1 is a schematic diagram of a biological signal measurement system according to embodiments.

The terminology used herein is for the purpose of describing particular embodiments only and is not intended to be limiting of the present invention.

As used herein, the singular forms "a", "an" and "the" are intended to include the plural forms as well, unless the context clearly indicates otherwise.

In describing preferred embodiments illustrated in the drawings, specific terminology may be employed for the sake of clarity. However, the disclosure of this patent specification is not intended to be limited to the specific terminology so selected, and it is to be understood that each specific element includes all technical equivalents that have the same function, operate in a similar manner, and achieve a similar result.

An embodiment of the present invention will be described in detail below with reference to the drawings.

An embodiment has an object to provide an information processing apparatus, an information processing method, a computer-readable medium, and a biological signal measurement system capable of appropriately changing a layout of information to be displayed, depending on a specific condition.

Exemplary embodiments of an information processing apparatus, an information processing method, a computer-readable medium, and a biological signal measurement system according to the present invention will be described in detail below with reference to the drawings. The present invention is not limited by the embodiments below, and components in the embodiments described below include one that can easily be thought of by a person skilled in the art, one that is practically identical, and one that is within an equivalent range. Further, within the scope not departing from the gist of the following embodiments, various omission, replacement, modifications, and combinations of the components may be made.

First Embodiment

Schematic Configuration of Biological Signal Measurement System

FIG. 1 is a schematic diagram of a biological signal measurement system according to embodiments. A biological signal measurement system 1 measures and displays, for example, a magnetoencephalography (MEG) signal and an electroencephalography (EEG) signal as a plurality of kinds of biological signals of a subject. The biological signals to be measured are not limited to the magnetoencephalography signal and the electroencephalography signal, but may be, for example, an electrical signal that is generated in accordance with activity of heart (electrical signal that can be represented on an electrocardiogram). As illustrated in FIG. 1, the biological signal measurement system 1 includes a measurement device 3 that measures one or more biological signals of the subject, a server 40 that records the one or more biological signals measured by the measurement device 3, and an information processing apparatus 50 that analyzes the one or more biological signals recorded in the server 40. In this example, the server 40 and the information processing apparatus 50 are described as separate devices, but at least a part of functions of the server 40 may be incorporated in the information processing apparatus 50, for example.

In the example in FIG. 1, the subject (to-be-measured person) lies on his/her back on a measurement table 4 while wearing electrodes (or sensors) for electroencephalography measurement on his/her head, and puts the head into a hollow 32 of a dewar 31 of the measurement device 3. The dewar 31 is a container in a cryogenic environment using liquid helium, and a number of magnetic sensors for magnetoencephalography measurement are arranged inside the hollow 32 of the dewar 31. The measurement device 3 collects electroencephalography signals from the electrodes and magnetoencephalography signals from the magnetic sensors and outputs data including the electroencephalography signals and the magnetoencephalography signals thus collected (hereinafter, may be referred to as "measurement data" in some cases) to the server 40. The measurement data recorded in the server 40 is read and displayed by the information processing apparatus 50 and then analyzed. In general, the dewar 31 with the built-in magnetic sensors and the measurement table 4 are arranged in a magnetic shielding room, but the magnetic shielding room is not illustrated for convenience of illustration.

The information processing apparatus 50 displays waveforms of the magnetoencephalography signals obtained from the plurality of magnetic sensors and waveforms of the electroencephalography signals obtained from the plurality of electrodes on the same time axis in a synchronous manner. However, as will be described later, any of the waveforms may be hidden depending on specific conditions. The electroencephalography signals are signals that represent electrical activity of nerve cells (the flow of ionic charge that occurs in neuronal dendrites during synapse transmission) by voltage values between the electrodes. The magnetoencephalography signals are signals that represent fine magnetic field variation that occurs due to electrical activity of the brain. The brain's magnetic field is detected by a high-sensitive superconducting quantum interference device (SQUID) sensor. The electroencephalography signals and the magnetoencephalography signals are one example of a "biological signal".

Hardware Configuration of Information Processing Apparatus

Figure 2:
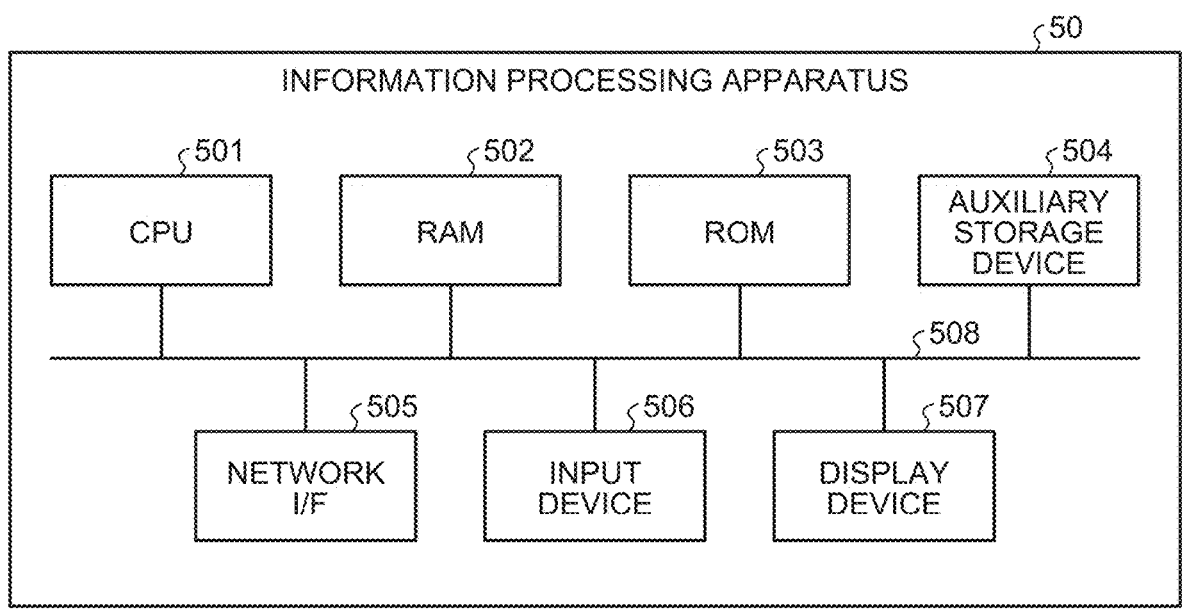
FIG. 2 is a diagram illustrating an example of a hardware configuration of an information processing apparatus.

FIG. 2 is a diagram illustrating an example of a hardware configuration of the information processing apparatus. A hardware configuration of the information processing apparatus 50 according to the first embodiment will be described with reference to FIG. 2.

As illustrated in FIG. 2, the information processing apparatus 50 includes a central processing unit (CPU) 501, a random access memory (RAM) 502, a read only memory (ROM) 503, an auxiliary storage device 504, a network interface (I/F) 505, an input device 506, and a display device 507, all of which are connected to one another via a bus 508.

The CPU 501 is an arithmetic device that controls entire operation of the information processing apparatus 50 and performs various kinds of information processing. The CPU 501 executes an information display program that is stored in the ROM 503 or the auxiliary storage device 504 and controls operation of displaying a measurement collection screen, an analysis screen, and the like.

The RAM 502 is a volatile storage device that is used as a working area for the CPU 501 and stores therein main control parameters and information. The ROM 503 is a nonvolatile storage device that stores therein a basic input/output program and the like. For example, the information display program as described above may be stored in the ROM 503.

The auxiliary storage device 504 is a storage device, such as a hard disk drive (HDD) or a solid state drive (SSD). The auxiliary storage device 504 stores therein, for example, a control program for controlling operation of the information processing apparatus 50, a layout table (to be described later) for associating specific conditions and layout contents, various kinds of data and files that are needed for operation of the information processing apparatus 50, and the like.

The network I/F 505 is a communication interface for performing communication with an apparatus, such as the server 40, on the network. The network I/F 505 is implemented by, for example, a network interface card (NIC) that is compatible with transmission control protocol (TCP)/Internet protocol (IP), or the like.

The input device 506 is, for example, a user interface, such as an input function of a touch panel, a keyboard, a mouse, or an operation button. The display device 507 is a display device that displays various kinds of information. The display device 507 is, for example, a display function of a touch panel, a liquid crystal display (LCD), an organic electro-luminescence (EL), or the like. The display device 507 displays the measurement collection screen and the analysis screen, and the screens are updated in accordance with input-output operation that is performed via the input device 506.

Meanwhile, the hardware configuration of the information processing apparatus 50 illustrated in FIG. 2 is one example, and it may be possible to include other devices. Further, the information processing apparatus 50 illustrated in FIG. 2 has a hardware configuration that is based on, for example, a personal computer (PC), but is not limited thereto, and may be a mobile terminal, such as a tablet. In this case, it is sufficient to adopt, as the network I/F 505, a communication interface that has a wireless communication function.

Furthermore, a hardware configuration of the server 40 is basically the same as the hardware configuration of the information processing apparatus 50 illustrated in FIG. 2. However, for example, if it is not necessary to display processing contents or the like of the server 40, it is not necessary to include the display device 507.

Figure 3:
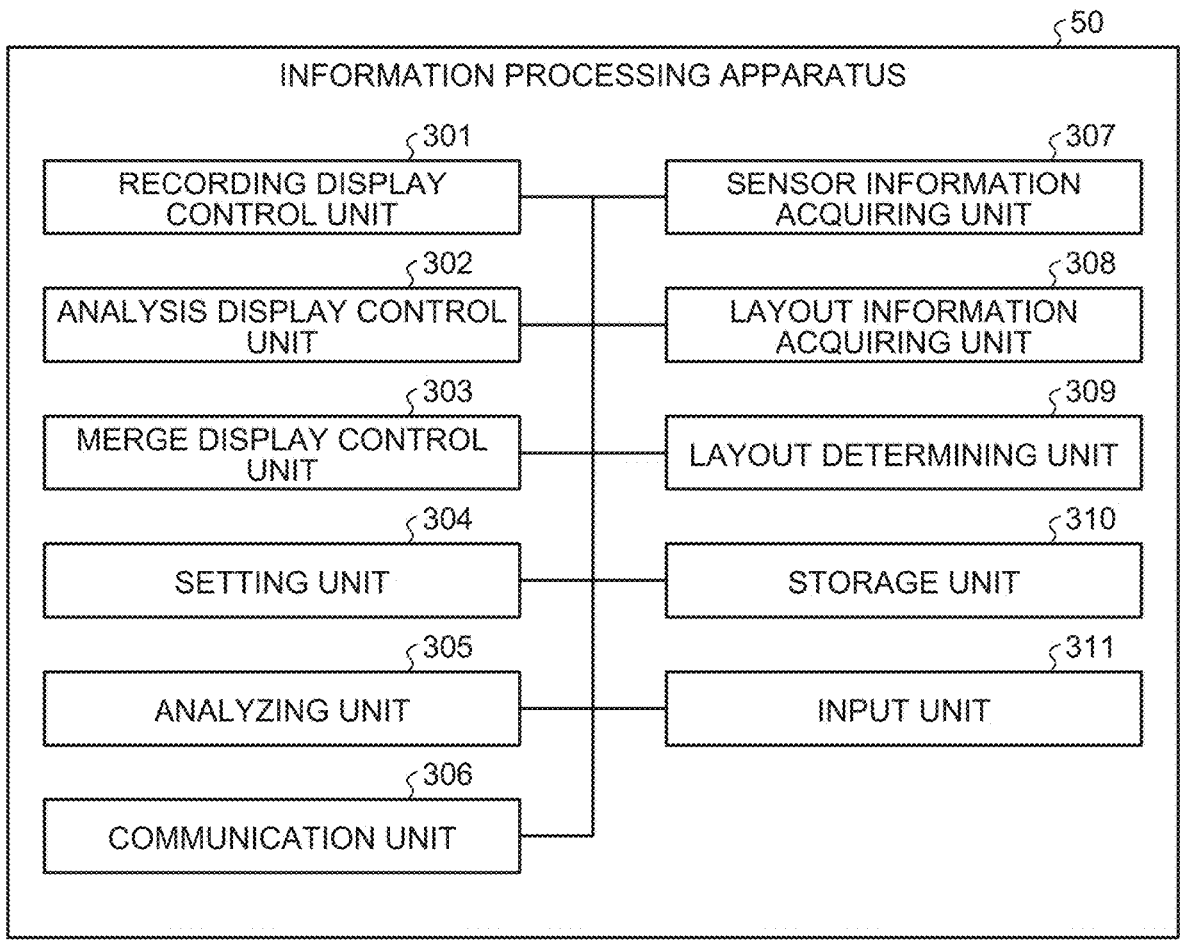
FIG. 3 is a diagram illustrating an example of a functional block configuration of the information processing apparatus.

Functional Block Configuration and Operation of Information Processing Apparatus FIG. 3 is a diagram illustrating an example of a functional block configuration of the information processing apparatus. The functional block configuration and operation of the information processing apparatus 50 according to the first embodiment will be described with reference to FIG. 3.

As illustrated in FIG. 3, the information processing apparatus 50 includes a recording display control unit 301, an analysis display control unit 302, a merge display control unit 303 (changing unit), a setting unit 304, an analyzing unit 305, a communication unit 306, a sensor information acquiring unit 307, a layout information acquiring unit 308 (acquiring unit), a layout determining unit 309 (determining unit), a storage unit 310, and an input unit 311.

Figure 6:
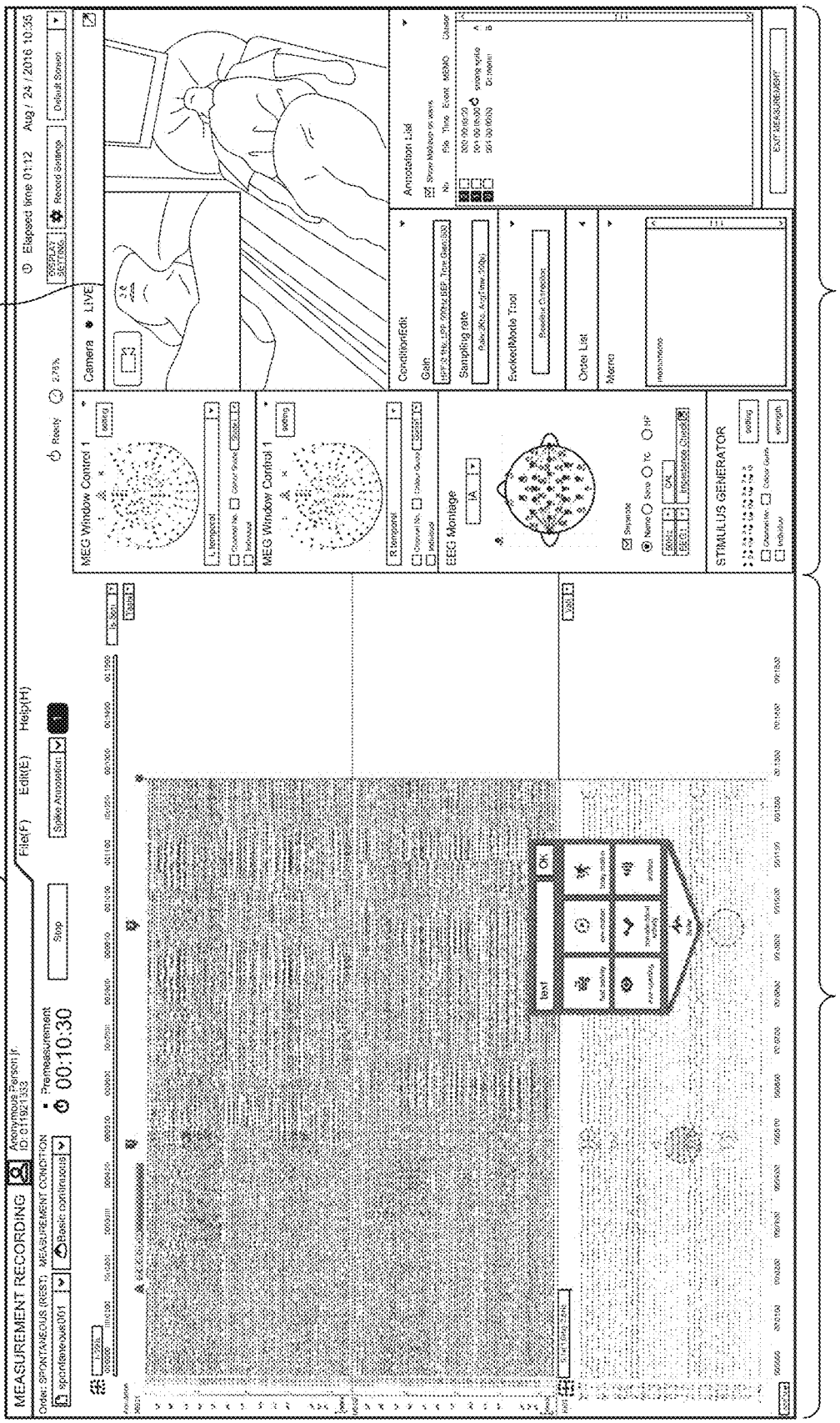
FIG. 6 is a diagram illustrating an example of a measurement recording screen.

The recording display control unit 301 is a functional unit that controls, for example, operation of displaying a measurement recording screen as illustrated in FIG. 6 etc. to be described later.

Figure 12:
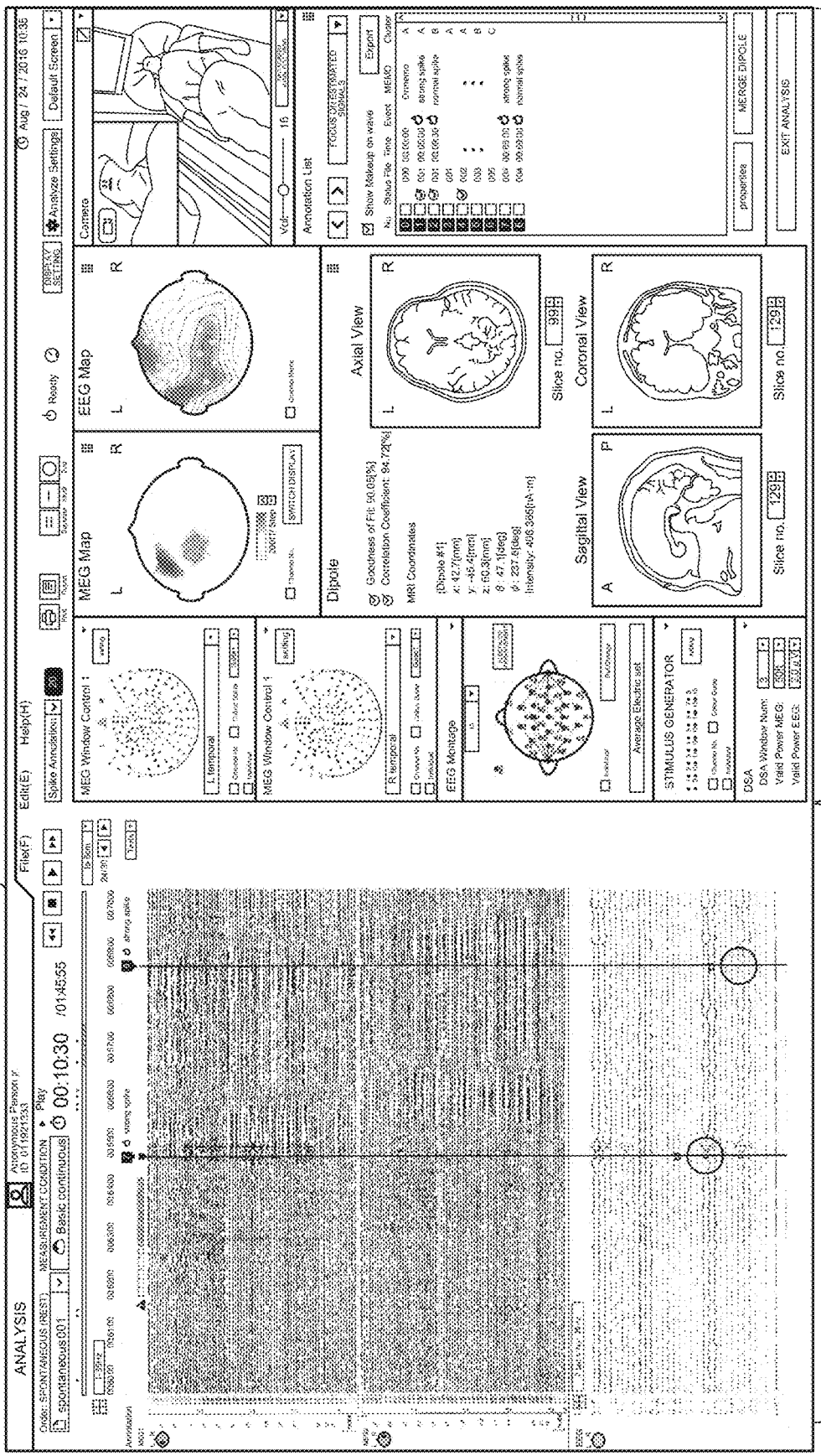
FIG. 12 is a diagram illustrating an example of an analysis screen.
Figure 18:
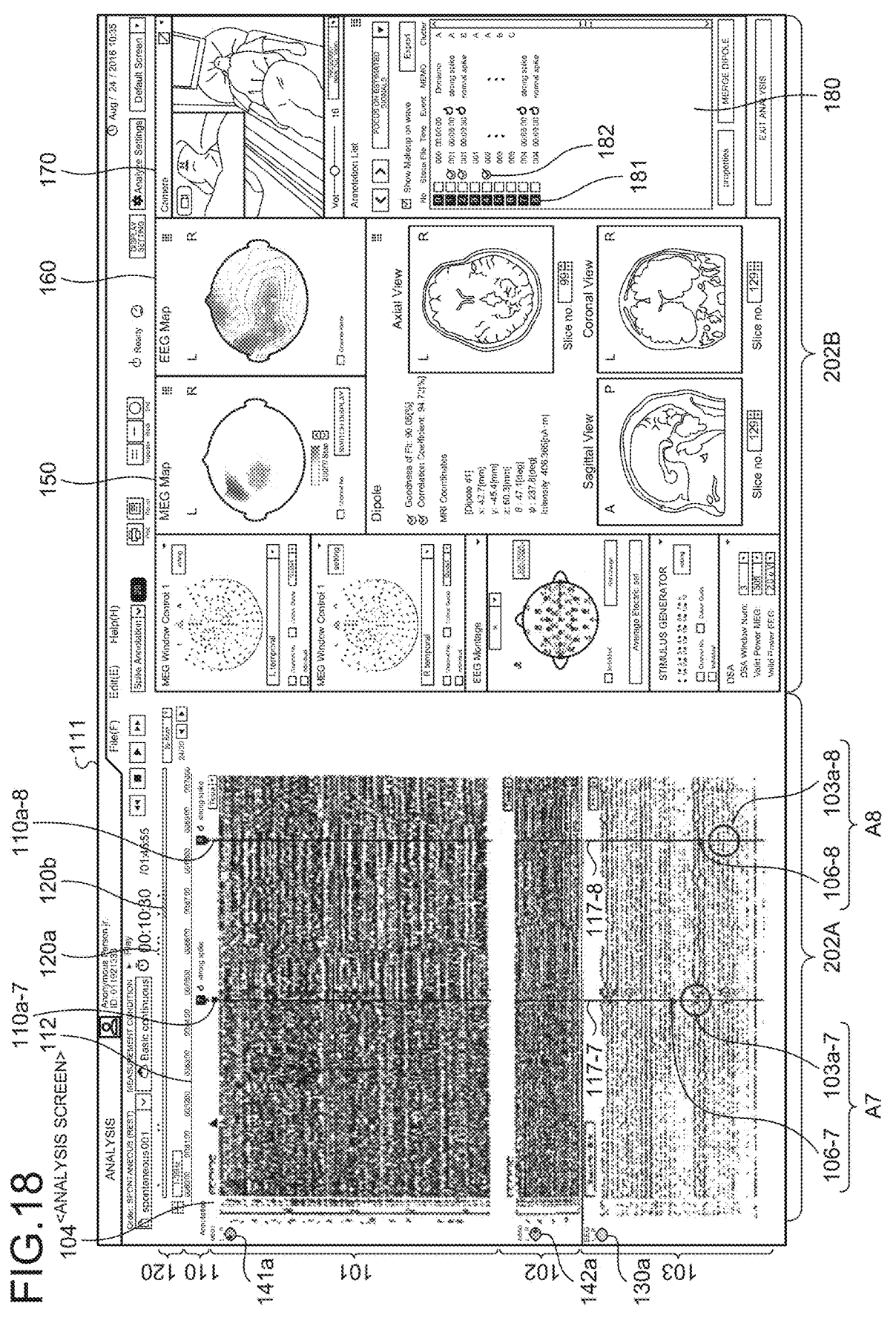

The analysis display control unit 302 is a functional unit that controls, for example, operation of displaying an analysis screen as illustrated in FIG. 12, FIG. 18, etc. to be described later.

Figure 26:
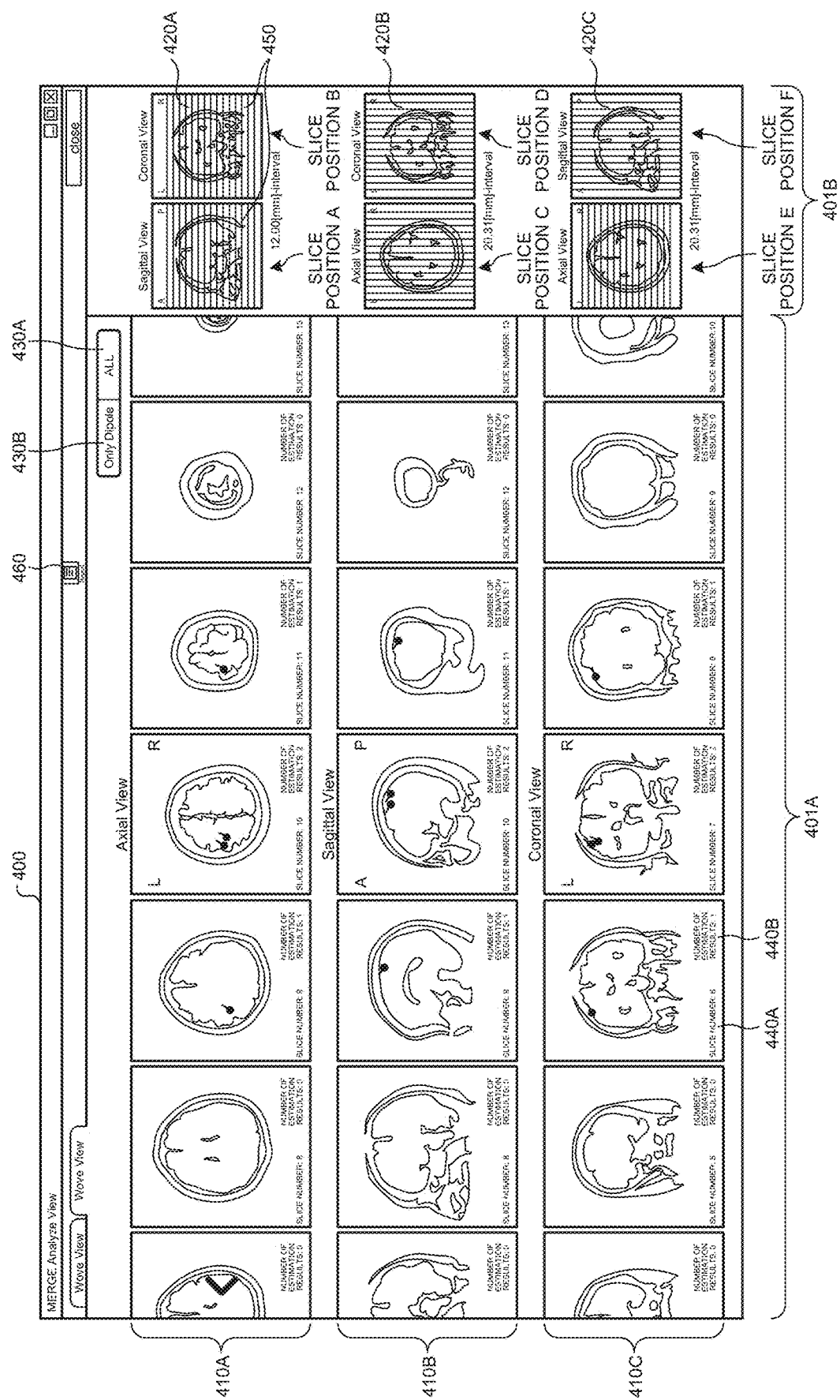
FIG. 26 is a diagram illustrating a screen that is displayed when a merge button is pressed.

The merge display control unit 303 is a functional unit that controls, for example, operation of displaying a merge screen 400 as illustrated in FIG. 26 etc. to be described later.

The setting unit 304 is a functional unit that sets a layout table for associating a result of a medical examination on a patient with a layout content to be displayed in the analysis screen, in accordance with input operation received by the input unit 311, and stores the layout table in the storage unit 310.

The analyzing unit 305 is a functional unit that analyzes sensor information (measured signal) that is acquired by the sensor information acquiring unit 307. Analysis of the sensor information includes analysis of signal waveforms, analysis of a singularity of amplitude, analysis of the brain's magnetic field including orientation of a current dipole, and the like. In other words, in this example, the analyzing unit 305 has a function to estimate a signal source corresponding to an annotation that is selected from the analysis screen.

The communication unit 306 is a functional unit that performs data communication with the measurement device 3, the server 40, or the like. The communication unit 306 is implemented by the network I/F 505 illustrated in FIG. 2.

The sensor information acquiring unit 307 is a functional unit that acquires sensor information (an electroencephalography signal or a magnetoencephalography signal) from the measurement device 3 or the server 40 via the communication unit 306.

The layout information acquiring unit 308 is a functional unit that acquires information (one example of determination information) indicating a specific condition for determining a layout of the analysis screen (to be described later) from the server 40 via the communication unit 306. Specifically, in the first embodiment, the layout information acquiring unit 308 acquires, as the information indicating the specific condition, patient information including a medical examination result on a patient (including a medical interview result) from the server 40.

The layout determining unit 309 is a functional unit that refers to a layout table, which is stored in the storage unit 310 (to be described later) and in which the medical examination result and the layout content of the analysis screen are associated, acquires a layout content corresponding to the medical examination result that is acquired by the layout information acquiring unit 308 and that serves as the information indicating the specific condition, and determines the acquired layout content as a layout of the analysis screen.

The storage unit 310 is a functional unit that stores therein measurement data, an analysis result, the layout table (to be described later), and the like. The storage unit 310 is implemented by the RAM 502 or the auxiliary storage device 504 illustrated in FIG. 2.

The input unit 311 is a functional unit that receives various kinds of input operation, such as operation of inputting annotation information to be added to the sensor information and input operation for causing the setting unit 304 to set the layout table. The input unit 311 is implemented by the input device 506 illustrated in FIG. 2.

The recording display control unit 301, the analysis display control unit 302, the merge display control unit 303, the setting unit 304, the analyzing unit 305, the sensor information acquiring unit 307, the layout information acquiring unit 308, and the layout determining unit 309 described above are implemented by causing the CPU 501 illustrated in FIG. 2 to read a program stored in the ROM 503 or the like, loads the program onto the RAM 502, and executes the program. Meanwhile, a part or all of the recording display control unit 301, the analysis display control unit 302, the merge display control unit 303, the setting unit 304, the analyzing unit 305, the sensor information acquiring unit 307, the layout information acquiring unit 308, and the layout determining unit 309 may be implemented by a hardware circuit, such as an application specific integrated circuit (ASIC) or a field-programmable gate array (FPGA), instead of the program that is software.

Furthermore, each of the functional units illustrated in FIG. 3 is presented to schematically illustrate the functions, and need not always be configured in the same manner. For example, a plurality of independent functional units illustrated in FIG. 3 may be configured as a single functional unit. Alternatively, functions included in a single functional unit illustrated in FIG. 3 may be divided into a plurality of parts and configured as a plurality of functional units.

Functional Block Configuration of Server

Figure 4:
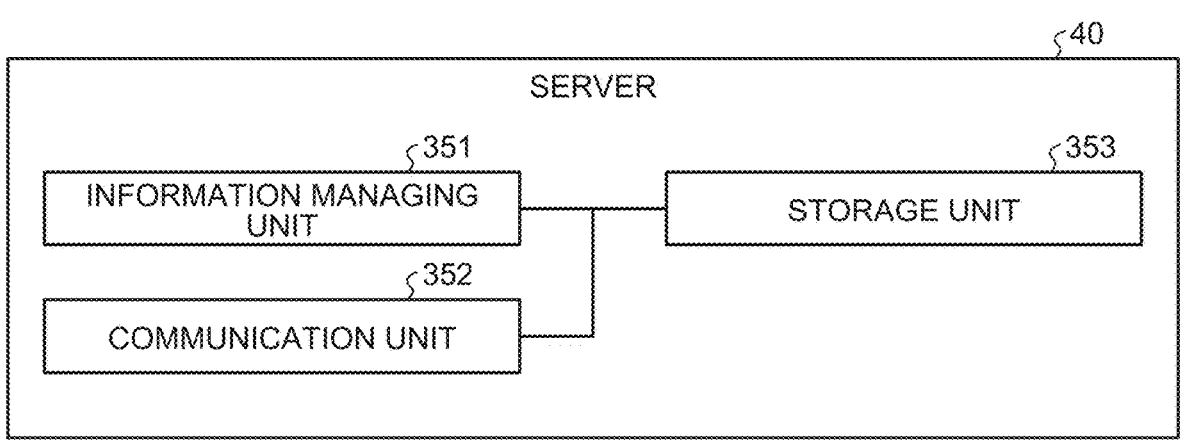
FIG. 4 is a diagram illustrating an example of a functional block configuration of a server.

FIG. 4 is a diagram illustrating an example of a functional block configuration of the server. The functional block configuration of the server 40 according to the first embodiment will be described with reference to FIG. 4.

As illustrated in FIG. 4, the server 40 includes an information managing unit 351, a communication unit 352, and a storage unit 353.

The information managing unit 351 is a functional unit that manages patient information including a medical examination result (including a medical interview result), role (specialty) information on a doctor etc., and the like. Specifically, for example, the information managing unit 351 reads, from the storage unit 353, the patient information, the role information, or the like requested by the information processing apparatus 50 and transmits the read information to the information processing apparatus 50, or the information managing unit 351 adds or updates new patient information or new role information in the storage unit 353 in accordance with an addition request or an update request issued by the information processing apparatus 50. The information managing unit 351 is implemented by causing the CPU 501 illustrated in FIG. 2 to load a program stored in the ROM 503 or the like onto the RAM 502 and execute the program.

The communication unit 352 is a functional unit that performs data communication with the information processing apparatus 50 or the like. The communication unit 352 is implemented by the network I/F 505 illustrated in FIG. 2.

The storage unit 353 is a functional unit that stores therein the patient information, user information including the role information, sensor information, measurement data, an analysis result, and the like. The storage unit 353 is implemented by the RAM 502 or the auxiliary storage device 504 illustrated in FIG. 2.

Meanwhile, each of the functional units illustrated in FIG. 4 is presented to schematically illustrate the functions, and need not always be configured in the same manner. For example, a plurality of independent functional units illustrated in FIG. 4 may be configured as a single functional unit. Alternatively, functions included in a single functional unit illustrated in FIG. 4 may be divided into a plurality of parts and configured as a plurality of functional units.

Start Screen

Figure 5:
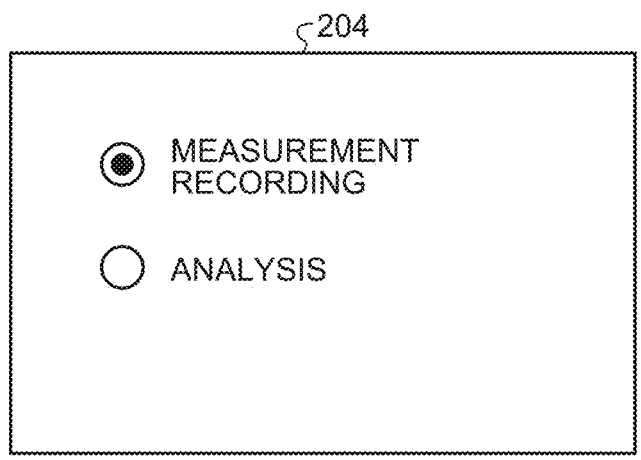
FIG. 5 is a diagram illustrating an example of a start screen displayed in the information processing apparatus.

FIG. 5 is a diagram illustrating an example of a start screen displayed by the information processing apparatus. A start screen 204 displays selection buttons for "measurement/recording" and "analysis". In electroencephalography and magnetoencephalography measurement, it is often the case that data measurement/recording and data analysis are performed by different entities. For example, when a measurement technician (measurer) selects the button of "measurement/recording", pieces of data measured by the measurement device 3 are sequentially stored in the server 40 and then read and displayed by the information processing apparatus 50. When a doctor selects the button of "analysis" after measurement and recording are completed, the recorded measurement data are read and analyzed.

Operation at the Time of Measurement/Recording

FIG. 6 is a diagram illustrating an example of the measurement recording screen. A tab 111 on the screen indicates that the screen is a "measurement recording" screen. The measurement recording screen includes a region 201A for displaying measured signal waveforms and a region 201B for displaying monitor information other than the signal waveforms. The region 201A for displaying the signal waveforms is arranged on the left side of the screen when viewed from the measurer's side, and the region 201B for displaying monitor information other than the signal waveforms is arranged on the right side of the screen when viewed from the measurer's side. This configuration prevents unnecessary movement of the line of sight of the measurer along with movement of a waveform that is detected and displayed in real time (displayed from the left side to the right side on the screen) and unnecessary movement of a mouse from the left-side region 201A to the right-side region 201B of the screen, so that it is possible to improve operation efficiency.

A monitor window 170 for checking the condition of a to-be-measured person during measurement is displayed in the region 201B of the display screen. By displaying a live video of the to-be-measured person during the measurement, it is possible to improve the reliability of checking and determination of signal waveforms as will be described later. While FIG. 6 illustrates a case in which the entire measurement recording screen is displayed in a display screen of a single monitor display (the display device 507), it may be possible to separately display the left-side region 201A and the right-side region 201B using two or more monitor displays.

Figure 7:
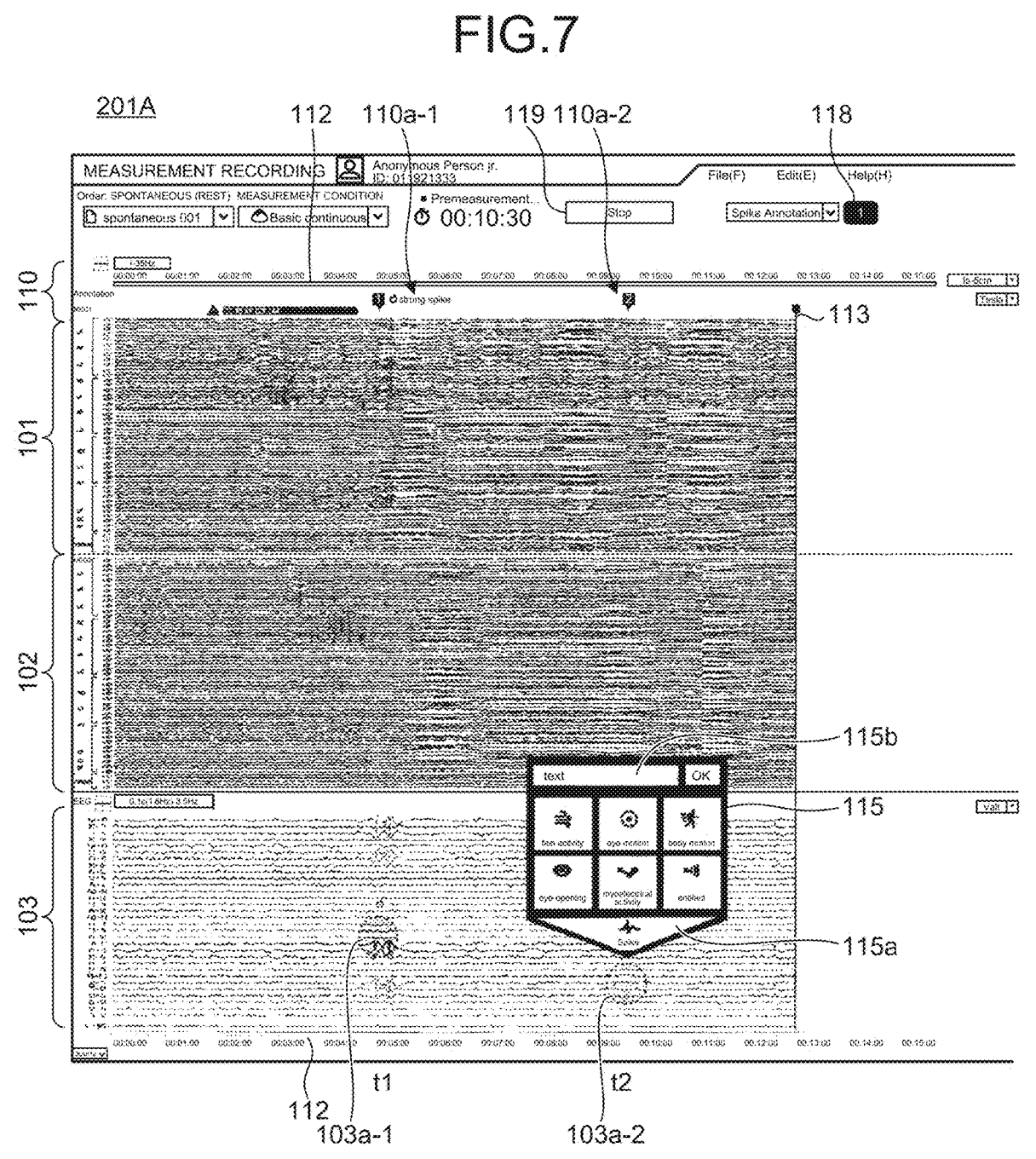

FIG. 7 is an enlarged view of the left-side region of the measurement recording screen. The region 201A includes a display region 110 for displaying time information on signal detection in a horizontal direction (first direction) of the screen, and display regions 101 to 103 for displaying a plurality of signal waveforms, which are based on the signal detection, in parallel in a vertical direction (second direction) of the screen.

The time information displayed in the display region 110 is a timeline including time display that is added along a time axis 112 in the example in FIG. 7, but it may be possible to display only a stripe-shaped axis without displaying time (number) or it may be possible to display only time (number) without arranging the axis. Meanwhile, it may be possible to display the time axis 112 to display a timeline below the display region 103, in addition to the display region 110 that is arranged on the upper side of the screen.

The recording display control unit 301 displays, in the region 201A, a plurality of signal waveforms that are acquired from a plurality of sensors of the same kind or a plurality of kinds of signal waveforms that are acquired from a plurality of kinds of sensors, in a synchronous manner on the same time axis 112. For example, waveforms of a plurality of magnetoencephalography signals that are obtained from the right side of the head of the to-be-measured person are displayed in parallel in the display region 101, and waveforms of a plurality of magnetoencephalography signals that are obtained from the left side of the head of the to-be-measured person are displayed in parallel in the display region 102. Waveforms of a plurality of electroencephalography signals are displayed in parallel in the display region 103. The plurality of electroencephalography signal waveforms are voltage signals that are measured among a plurality of electrodes. Each of the signal waveforms is displayed in association with an identification number or a channel number of a sensor that has acquired the signal.

When measurement is started and measurement information is collected from each of the sensors, signal waveforms are displayed rightward from the left edge of each of the display regions 101 to 103 in the region 201A with time. A line 113 indicates a measurement time (current time) and moves from left to right in the screen. When a signal waveform is displayed up to the right edge of the region 201A (the right edge of the time axis 112), the signal waveform is gradually deleted from the left edge to the right side of the screen, and a new signal waveform is sequentially displayed form left to right in the deleted position and the line 113 moves rightward from the left edge. Along with this operation, a lapse of time is displayed on the time axis 112 in the display region 110 in the horizontal direction in accordance with the progress of the measurement. The measurement and recording are continued until a termination button 119 is pressed.

As a feature of the embodiments, when a measurer (recording person) finds waveform disturbance on a signal waveform, a singularity of amplitude, or the like during data recording, it is possible to mark a problematic portion or range on the signal waveform. The portion or the range to be marked can be specified by click operation or the like using a mouse (one example of the input unit 311). The specified portion (or range) is displayed with emphasis on the signal waveforms in the display regions 101 to 103, and a temporal position or a time range corresponding to a specification result is displayed along the time axis 112 in the display region 110. Information on the marking including the display on the time axis 112 is stored in the storage unit 353 of the server 40 (or the storage unit 310) together with signal waveform data. The specified portion corresponds to a certain time, and the specified range corresponds to a certain range including a certain time.

In the example in FIG. 7, a range including one or more channels is specified at a time t1 in the display region 103, and a mark 103a-1 representing a time period including the time t1 is displayed in a highlighted manner. An annotation 110a-1 indicating a specification result is displayed at a corresponding temporal position in the display region 110 in association with the display of the mark 103a-1. At a time t2, a different waveform position or a neighboring position of the different waveform position is marked in the display region 103, and a mark 103a-2 is displayed in a highlighted manner at this position (the time t2) or a neighboring region (at least a time range or any one of the waveforms is specified). At the same time, an annotation 110a-2 is displayed at a corresponding temporal position (time range) in the display region 110. Here, the annotation indicates that related information is added as an annotation to certain data. In the first embodiment, the annotation is displayed based on at least the specified time information and is displayed in association with at least a position at which a waveform based on the time information is displayed. Further, when a plurality of channels are displayed, annotations may be displayed in association with corresponding channel information.

The annotation 110a-1 added to the time t1 in the display region 110 contains, as one example, an annotation identification number and information indicating an attribute of the waveform. In this example, an annotation number of "1", an icon indicating an attribute of the waveform, and text information of "strong spike" are displayed.

If the measurer specifies a different waveform portion or a neighboring region of the different waveform portion at the time t2, the recording display control unit 301 displays the mark 103a-2 in a highlighted manner in the specified portion, and simultaneously displays an annotation number of "2" at a corresponding temporal position in the display region 110. Furthermore, the recording display control unit 301 displays a pop-up window 115 for selecting an attribute in the portion that is displayed in a highlighted manner. The pop-up window 115 includes selection buttons 115*a* for selecting various attributes, and an input box 115*b* for inputting comments and additional information. The selection buttons 115*a* indicate, as attributes of a waveform, causes of waveform disturbance, such as "fast activity", "eye motion", "body motion", and "spike". The measurer is able to check the condition of the to-be-measured person using the monitor window 170 (see FIG. 6) in the region 201B of the screen, and therefore is able to appropriately select an attribute indicating a cause of waveform disturbance. For example, when a spike occurs in a waveform, it is possible to determine whether the spike indicates a symptom of epilepsy or the spike is caused by body motion (sneeze or the like).

The same operation is performed at the time t1. In FIG. 7, the selection button 115*a* for "spike" is selected in the pop-up window 115 and "strong spike" is input in the input box 115*b*, so that the recording display control unit 301 displays the annotation 110*a*-1 in the display region 110. With this display mode, when displaying a number of signal waveforms in a synchronous manner on the same time axis 112, it is possible to easily and visually specify a portion or range of interest in the signal waveforms, and it is possible to easily recognize basic information on the portion of interest.

Meanwhile, a part or all of the annotation 110*a*-1, e.g., at least one of the attribute icon and the text annotation, may also be displayed near the mark 103*a*-1 on the signal waveform in the display region 103. Adding an annotation on a signal waveform may cause interference with checking of a waveform shape; therefore, when displaying an annotation on the signal waveforms in the display regions 101 to 103, it is preferable to allow selection of display or non-display of the annotation.

A counter box 118 displays a cumulative number of spike annotations. Every time "spike" is selected, a counter value of the counter box 118 is incremented, so that it is possible to recognize the total number of spikes from the start of recording to the current time (the line 113) at a glance.

Figure 8:
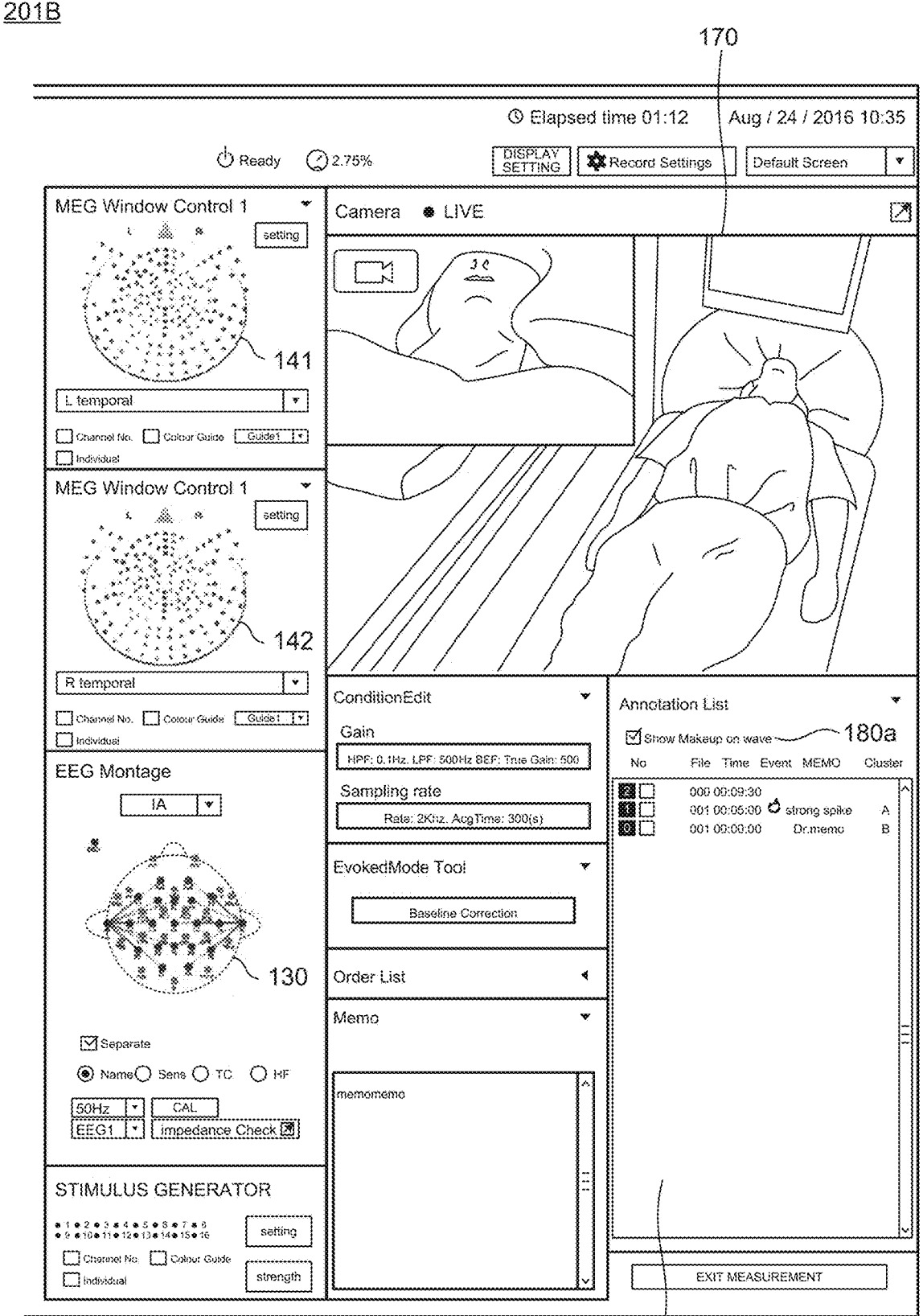
FIG. 8 is an enlarged view of a right-side region of the measurement recording screen.

FIG. 8 is an enlarged view of the right-side region of the measurement recording screen. FIG. 8 illustrates a state at the same time (a time point indicated by the line 113) as the case illustrated in FIG. 7. The monitor window 170 in the region 201B displays a live video of the condition of the to-be-measured person who is lying down on the measurement table 4 with his/her head in the measurement device 3. In the region 201B, distribution maps 141, 142, and 130 corresponding to the respective signal waveforms in the display regions 101, 102, and 103 and an annotation list 180 are displayed. The annotation list 180 is a list of annotations that are marked on the signal waveforms illustrated in FIG. 7. Every time a certain position or range is specified on the signal waveforms in the display regions 101 to 103 and an annotation is added, corresponding information is sequentially added to the annotation list 180. Annotations are added and displayed in the annotation list 180 on the measurement recording screen in descending order (the newest data is displayed at the top) for example, but embodiments are not limited to this example. It may be possible to display the annotation list 180 in ascending order, but in this case, the annotation list 180 is displayed such that correspondence relationships with the annotations that are displayed along the time axis 112 in the display region 110 can be clarified. Further, it may be possible to change a display order or sort the annotations by items.

In the example in FIG. 8, time information that corresponds to the annotation number of "1" and annotation information that has been added are listed. As the annotation information, an attribute icon representing "spike" and text of "strong spike" are recorded. Further, time information corresponding to the annotation number of "2" is listed at the time at which the mark 103*a*-2 is displayed in a highlighted manner. In this example, the "annotation" may be regarded as a combination of the annotation number, the time information, and the annotation information, may be regarded as only the annotation information, or may be regarded as a combination of the annotation information and either one of the annotation number and the time information.

Furthermore, a selection box 180*a* for selecting display or non-display is arranged near the annotation list 180. When non-display is selected by the selection box 180*a*, annotations other than highlighted marks on the signal waveforms in the display regions 101 to 103 are hidden, but annotations displayed along with the time axis 112 in the display region 110 are maintained. With this configuration, it is possible to recognize the annotation information without interfering with visibility of the signal waveforms.

Figure 9:
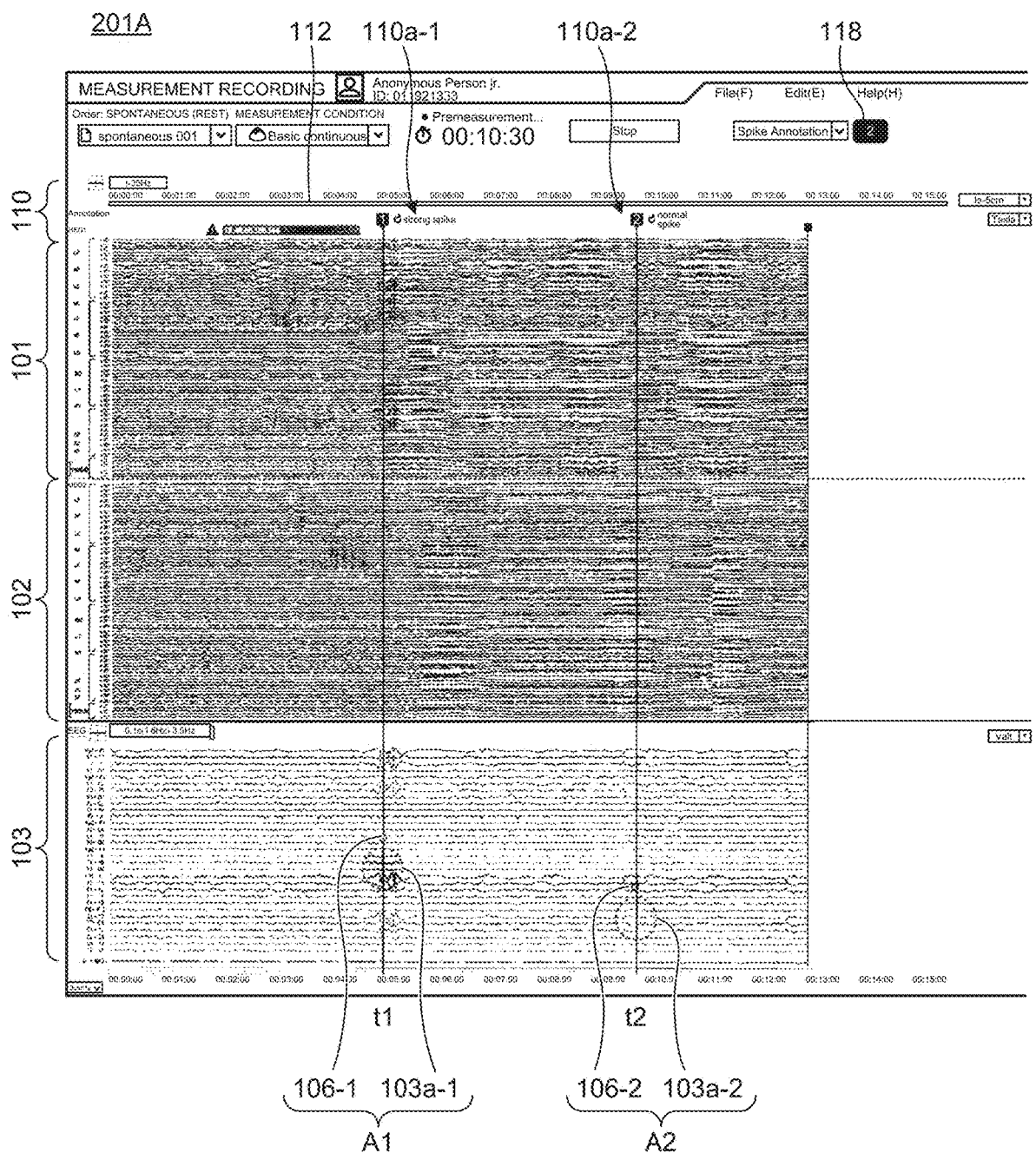
FIG. 9 is a diagram illustrating a screen that is displayed immediately after annotation information is input.

FIG. 9 is a diagram illustrating a screen that is displayed immediately after the annotation information is input. Specifically, FIG. 9 illustrates a screen that is displayed immediately after "spike" is selected in the pop-up window 115 and text of "normal spike" is input at the time t2. If an "OK" button is selected in the pop-up window 115 illustrated in FIG. 7, the recording display control unit 301 closes the pop-up window 115 and displays the annotation 110*a*-2 at a corresponding temporal position in the display region 110 as illustrated in FIG. 9. The recording display control unit 301 displays an attribute icon representing "spike" and text information of "normal spike" in association with the annotation number of "2". At the same time, the value of the counter box 118 is incremented. Further, the recording display control unit 301 displays an attribute icon 106-2 near the mark 103*a*-2 that is displayed in a highlighted manner. In this example, an attribute icon 106-1 is also displayed near the mark 103*a*-1, but it is possible to select whether to display or hide the attribute icons 106-1 and 106-2 as described above. An annotation A1 including the mark 103*a*-1 and the attribute icon 106-1 and an annotation A2 including the mark 103*a*-2 and the attribute icon 106-2 are also included in the annotation information.

FIG. 10 is a diagram illustrating an updated annotation list. When an annotation corresponding to the mark 103*a*-2 is added in the left-side region 201A of the measurement recording screen, the annotation list 180 is updated. A text of "normal spike" is added to the annotation number of "2".

Similarly, every time a specific portion or range is specified on a signal waveform in the region 201A during measurement, the specified portion is displayed with emphasis and annotation information is displayed along the time axis 112 in the display region 110. In the region 201B, the annotation information is sequentially added to the annotation list 180.

Meanwhile, it is not always necessary to display the annotation number in the annotation list 180 and the region 201A in which the signal waveforms are displayed, and it may be possible not to use the annotation number. It is possible to use, as identification information, arbitrary information that can identify an added annotation. For example, it may be possible to display an attribute icon, display an attribute text ("strong spike" or the like), and display a time near the time axis 112, in an associated manner. Further, it may be possible to additionally display a file number (a number that is displayed in an item of "File" in FIG. 10) in the region 201A.

If the termination button 119 (see FIG. 7) is selected (pressed) and measurement is terminated, the highlighted portions specified in the display regions 101 to 103 are stored in association with the signal waveforms. The annotation information that is displayed at the corresponding temporal position in the display region 110 is also stored in association with the annotation number and the time. The counter value of the counter box 118 and related information, such as contents of the annotation list 180, are also stored. By storing the display information as described above, an analyzer can easily recognize and analyze a problematic portion even when the analyzer and the measurer are different persons.

Figure 11:
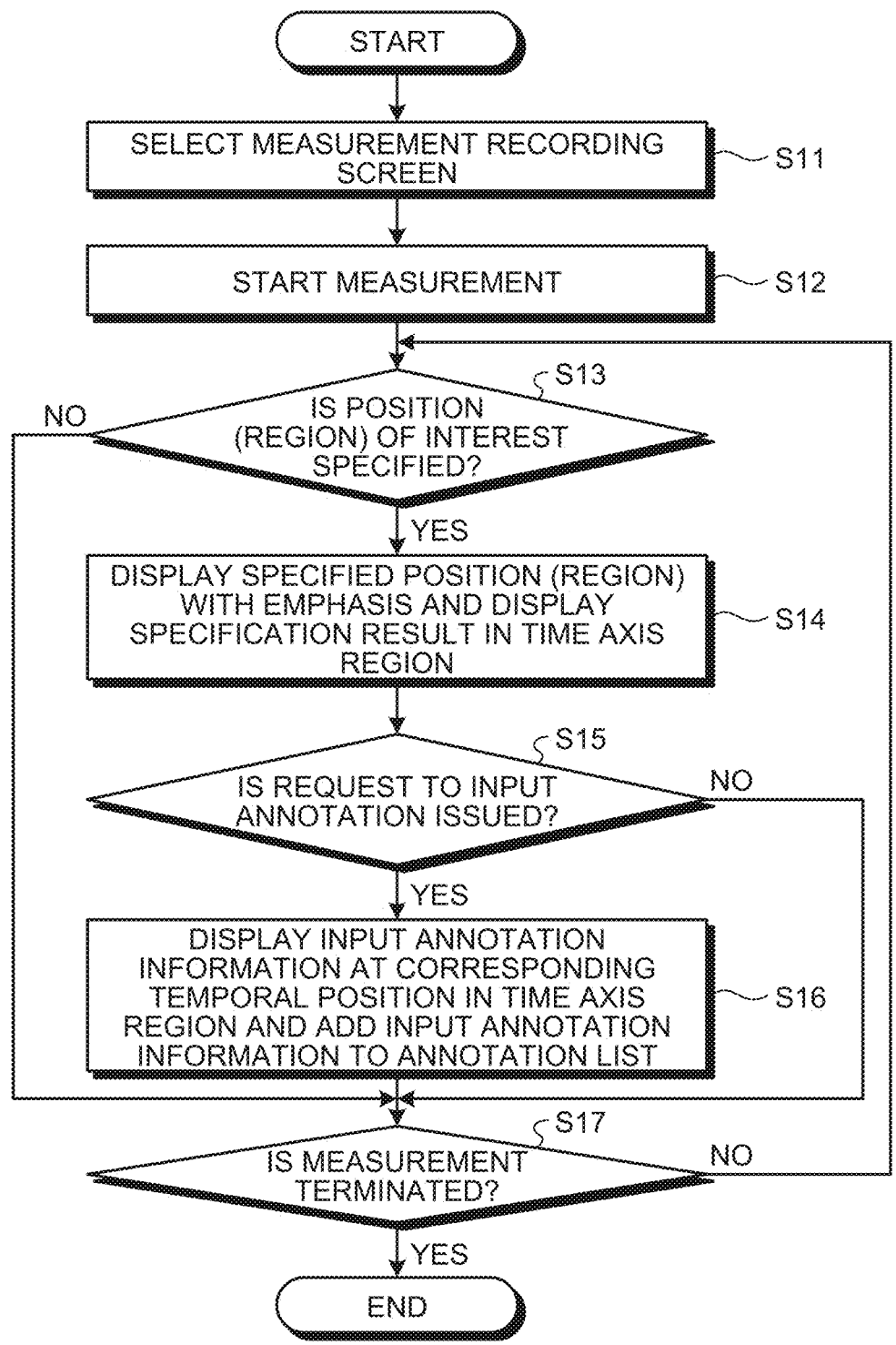
FIG. 11 is a flowchart illustrating operation that is performed by the information processing apparatus at the time of measurement and recording.

FIG. 11 is a flowchart illustrating operation performed by the information processing apparatus at the time of measurement and recording. If "measurement recording" is selected in the start screen 204 illustrated in FIG. 5 (Step S11), measurement is started, and waveforms of a plurality of signals are displayed in a synchronous manner along the same time axis (Step S12). Here, "a plurality of signal waveforms" includes both of a plurality of signal waveforms that are detected by a plurality of sensors of the same kind and a plurality of signal waveforms that are detected by a plurality of kinds of sensors. In this example, waveforms of a plurality of biological signals include waveforms of magnetoencephalography signals that are obtained from a group of magnetic sensors corresponding to the right side of the head of the to-be-measured person, waveforms of magnetoencephalography signals that are obtained from a group of magnetic sensors corresponding to the left side of the head of the to-be-measured person, and waveforms of electroencephalography signals that are obtained from electrodes for electroencephalography measurement on the to-be-measured person, but embodiments are not limited to this example. Meanwhile, it is possible to arbitrarily select sensors not only from left and right sensor groups, but also from arbitrary parts, such as a parietal region, a frontal lobe, and a temporal lobe. For example, when a sensor corresponding to the parietal region is selected in "MEG Window Control 1" (the distribution map 141) illustrated in FIG. 8, other sensors are selected in "MEG Window Control 2" (the distribution map 142).

The information processing apparatus 50 determines whether a portion or range of interest is specified on the displayed signal waveforms (Step S13). If the portion or range of interest is specified (YES at Step S13), the specified portion is displayed with emphasis in the display regions (the display regions 101 to 103) of the signal waveforms, and a specification result is displayed at a corresponding temporal position in the time axis region (the display region 110) (Step S14). The specification result includes information indicating that specification is performed or information for identifying the specification. At the same time, before, or after the specification result is displayed in the time axis region, it is determined whether a request to input an annotation is issued (Step S15). If the request to input an annotation is issued (YES at Step S15), input annotation information is displayed at a corresponding temporal position in the time axis region and is added to the annotation list 180 (Step S16). Thereafter, it is determined whether a measurement termination command is input (Step S17). If a position (region) of interest is not specified (NO at Step S13) or if the request to input an annotation is absent (NO at Step S15), the process proceeds to Step S17 and it is determined whether to terminate the measurement. The processes from Step S13 to S16 are repeated until the measurement is terminated (YES at Step S17).

Through the information display method as described above, it is possible to provide a measurement recording screen in which visibility of signal information is improved when signals are collected from a plurality of sensors.

Operation at the Time of Analysis

FIG. 12 is a diagram illustrating an example of the analysis screen. The analysis screen is displayed when an "analysis" button is selected in the start screen 204 illustrated in FIG. 5. The tab 111 on the screen indicates that the screen is the "analysis" screen. The analysis screen is a screen in which biological data indicating a temporal change of one or more biological signals of a subject measured by measurement (in this example, magnetoencephalography signals that are obtained from a group of magnetic sensors corresponding to the right side of the head of the to-be-measured person, magnetoencephalography signals that are obtained from a group of magnetic sensors corresponding to the left side of the head of the to-be-measured person, and electroencephalography signals that are obtained from electrodes for electroencephalography measurement on the to-be-measured person) is associated with an annotation that is input with respect to the biological data at the time of measurement. Meanwhile, in the first embodiment, a layout of the analysis screen is changed depending on information indicating a specific condition (in the first embodiment, patient information including a medical examination result) as will be described later; however, in FIG. 12 to FIG. 17, display operation in the analysis screen with a basic layout that is used before the layout is changed.

The information processing apparatus 50 (the analysis display control unit 302) of the first embodiment has a function to control display of the analysis screen on a display unit (a display device 28 to be described later). In the example illustrated in FIG. 12, the analysis screen includes a region 202A for displaying waveforms (corresponding to the biological data) indicating temporal changes of three recorded biological signals together with annotations, and a region 202B for displaying analysis information. The region 202A for displaying the recorded signal waveforms and the annotation information is arranged on the left side of the screen when viewed from the measurer's side, and the region 202B for displaying analysis is arranged on the right side of the screen when viewed from the measurer's side. This is because this configuration can improve operation efficiency for checking or confirming an analysis result in the region 202B by operating a mouse or the like while checking or selecting a signal waveform in the region 202A at the time of analysis.

In the first embodiment, the waveforms of the magnetoencephalography signals in the display regions 101 and 102 (to be described later in FIG. 13) are displayed above a screen of the waveforms of the electroencephalography signals in the display region 103 (to be described later in FIG. 13) of the region 202A. Further, in the region 202B arranged on the right side of the region 202A, the magnetoencephalography distribution maps 141 and 142 (to be described later in FIG. 14) are displayed in a screen region that is near the region 202A and on the upper part of the screen, and the electroencephalography distribution map 130 (to be described later in FIG. 14) is displayed below the magnetoencephalography distribution maps 141 and 142. Therefore, the analyzer is able to move the line of sight in order of "the waveforms of the electroencephalography signals" in the display region 103, "waveforms of the magnetoencephalography signals" in the display regions 101 and 102, the magnetoencephalography distribution maps 141 and 142, and the electroencephalography distribution map 130 (clockwise in this example). Consequently, the analyzer (or the measurer) can efficiently move the line of sight, so that it is possible to improve the analysis operation efficiency. Meanwhile, while it is explained that the line of sight moves clockwise in the example described above, embodiments are not limited to this example.

Figure 13:
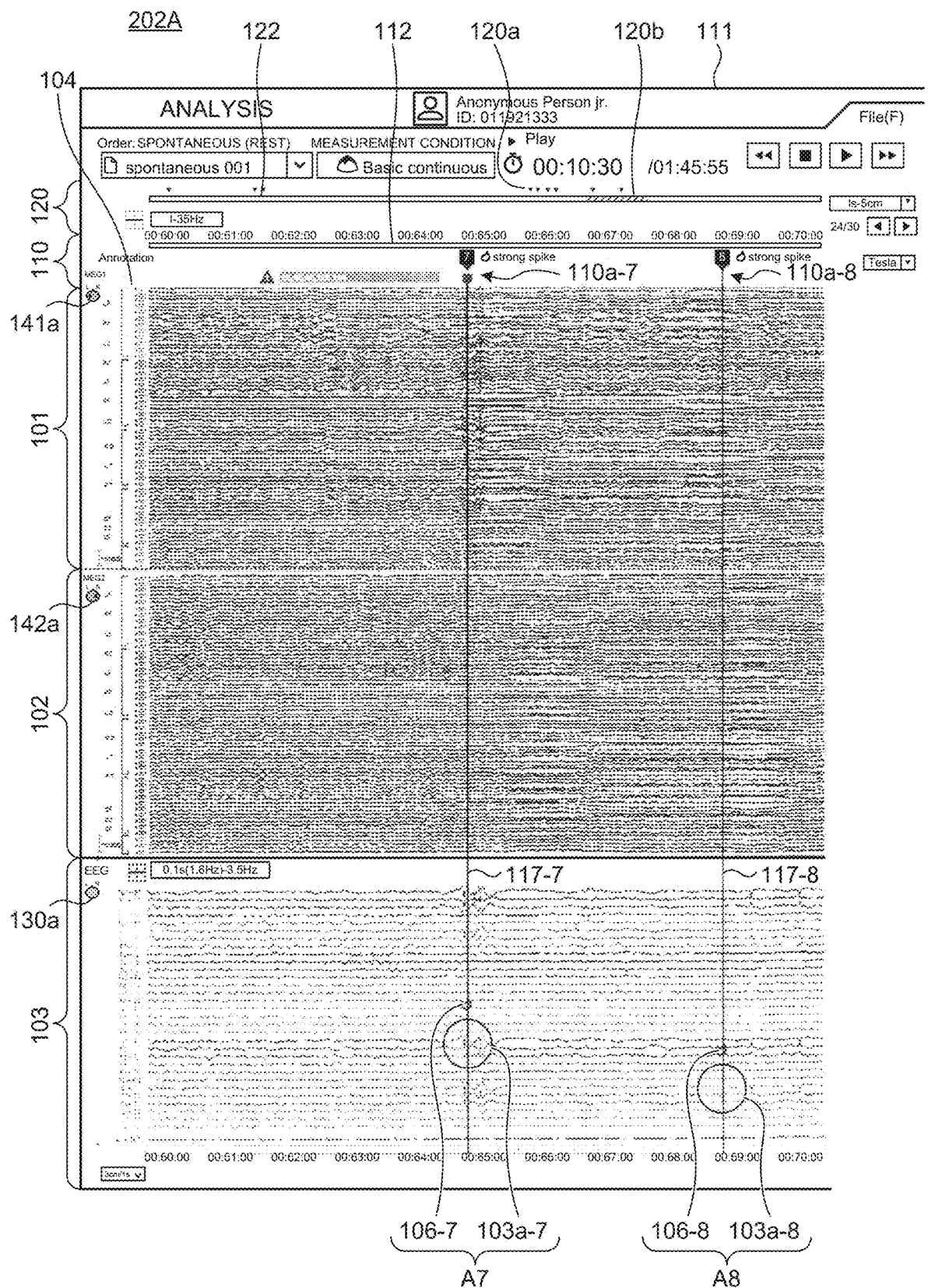
FIG. 13 is an enlarged view of a left-side region of the analysis screen.

FIG. 13 is an enlarged view of the left-side region of the analysis screen. The region 202A includes the display region 110 and a display region 120 for displaying time information at the time of measurement in the horizontal direction (first direction) of the screen, and includes the display regions 101 to 103 for displaying different kinds of recorded signal waveforms in parallel in the vertical direction (second direction) of the screen. Waveforms of a plurality of magnetoencephalography signals that are obtained from the right side of the head of the to-be-measured person are displayed in parallel in the display region 101, and waveforms of a plurality of magnetoencephalography signals that are obtained from the left side of the head of the to-be-measured person are displayed in parallel in the display region 102. Waveforms of a plurality of electroencephalography signals are displayed in parallel in the display region 103. The plurality of electroencephalography signal waveforms are voltage signals that are measured among a plurality of electrodes. Each of the signal waveforms is displayed at a channel axis 104, in association with an identification number or a channel number of a sensor that has acquired the signal.

The time axis 112 that indicates a lapse of time at the time of recording and annotations 110a-7 and 110a-8 that are added along the time axis 112 are displayed in the display region 110. A time axis 122 that displays the entire recording time is displayed in the display region 120. A pointer mark 120a indicating a temporal position at which an annotation is added and a time zone 120b indicating a time zone in which signal waveforms that are currently displayed in the display regions 101 to 103 are recorded are displayed along the time axis 122. With this display, the analyzer is able to intuitively recognize a timing at which a currently-analyzed signal waveform is acquired during measurement and recording.

The analyzer is able to display signal waveforms corresponding to a desired time zone in the display regions 101 to 103 by, for example, dragging the time zone 120b on the time axis 122 after opening the analysis screen. Alternatively, as will be described later, by selecting a desired annotation from the annotation list 180, it is possible to display signal waveforms that are present at and around the annotation in the display regions 101 to 103.

The display regions 101 to 103 display annotations A7 and A8 that are added to the signal waveforms at the time of recording. Marks 103a-7 and 103a-8 are displayed in a highlighted manner, and corresponding attribute icons 106-7 and 106-8 are displayed near the marks 103a-7 and 103a-8. Further, vertical lines 117-7 and 117-8 indicating temporal positions of the marks 103a-7 and 103a-8 are displayed. With the display of the lines 117-7 and 117-8, when an annotation is added in association with specification of a predetermined portion in the display region 103 for example, it is possible to easily view the specification result even in the display regions 101 and 102 that are display areas for different kinds of signals. The lines 117-7 and 117-8 may be included in the annotation information because they make it possible to easily view the annotation information, and therefore may be referred to as "annotation lines". By selecting the line 117-7 or the line 117-8, signal waveforms in a predetermined time period at around the selected time are displayed in an enlarged manner. This process will be described later.

Further, reduced images 141a, 142a, and 130a of the magnetoencephalography distribution maps 141, 142, and the electroencephalography distribution map 130 are displayed near the channel axis 104. The reduced images 141a, 142a, and 130a are respective reduced views of the magnetoencephalography distribution maps 141, 142, and the electroencephalography distribution map 130, and show setting states of the magnetoencephalography distribution maps 141, 142, and the electroencephalography distribution map 130. For example, ranges of sensors selected in the magnetoencephalography distribution maps 141 and 142 are colored with black in the reduced images 141a and 142a.

Figure 14:
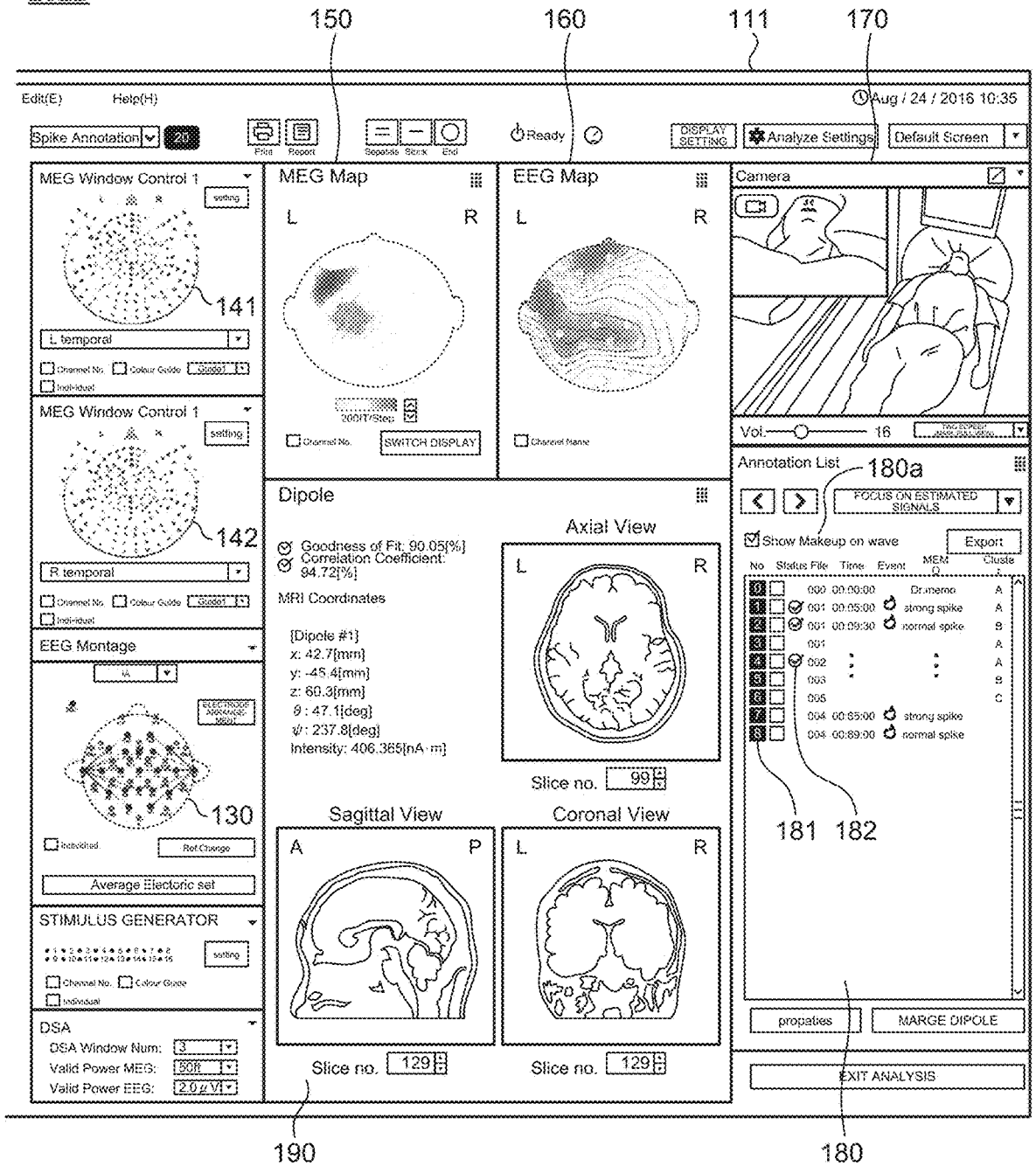
FIG. 14 is an enlarged view of a right-side region of the analysis screen.

FIG. 14 is an enlarged view of the right-side region of the analysis screen. The region 202B displays the magnetoencephalography distribution maps 141 and 142 corresponding to the signal waveforms that are displayed in the display regions 101 and 102, and the electroencephalography distribution map 130 corresponding to the signal waveform that is displayed in the display region 103. Further, the region 202B displays an isofield contour map 150 of a magnetoencephalograph, a map area 160 of an electroencephalograph, and a display window 190 for a tomography image that is acquired by magnetic resonance imaging (MRI) of the brain of the to-be-measured person. In the isofield contour map 150, a spring region and a sucking region of a magnetic field are displayed in different colors, so that it is possible to visually recognize a direction of the flow of electrical current. The isofield contour map 150 and the map area 160 are information that are obtained after measurement is completed, and the MRI tomography image displayed in the display window 190 is information that is separately obtained through an examination.

A video of the to-be-measured person at the time of measurement is displayed in the monitor window 170 in synchronization with times at which the signal waveforms in the display regions 101 to 103 are obtained. The analyzer is able to analyze the signal waveforms while checking the condition of the to-be-measured person by viewing the monitor window 170.

The annotation list 180 contains a list of all of annotations that are added during the measurement and recording. In the annotation list 180, pieces of annotation information (an attribute icon, text input information, and the like) that are added in association with annotation numbers 181 are written.

Meanwhile, the annotation list 180 in the analysis screen is displayed such that the added annotations are listed in ascending order for example (the oldest data is listed at the top), but embodiments are not limited to this example. Similarly to the measurement recording screen, it is not always necessary to use the annotation number and it may be possible to identify an annotation by using a combination of a time, a file name, an attribute, and the like. Further, it may be possible to change a display order of the annotations contained in the annotation list 180 or sort the annotations by items.

By clicking the desired annotation number 181 or a desired row, it is possible to display, in the display regions 101 to 103 illustrated in FIG. 13, signal waveforms corresponding to a predetermined time zone including the temporal position to which the annotation is added.

The analysis display control unit 302 displays an estimation completion mark 182 with respect to an annotation, for which the analyzer has estimated a final signal source by checking the signal waveform corresponding to the annotation portion, unlike the measurement recording screen.

If non-display is specified by the selection box 180a for selecting whether to display or hide an annotation, the attribute icons 106-7 and 106-8 in the display region 103 illustrated in FIG. 13 are hidden. Meanwhile, it may be possible to allow selection of non-display of the highlighted marks 103a-7 and 103a-8 by the selection box 180a that is for selecting display or non-display.

Figure 15:
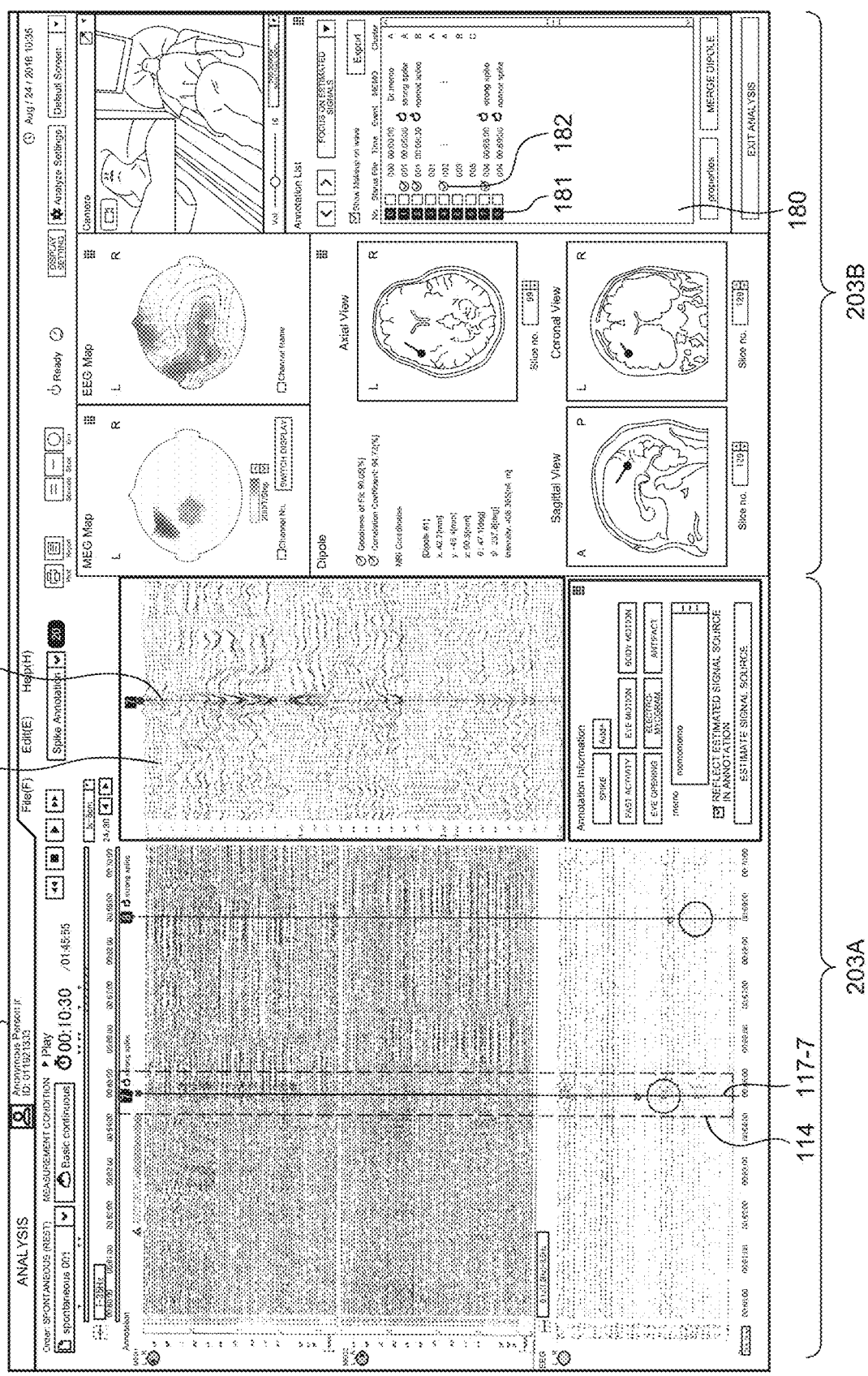
FIG. 15 is a diagram illustrating a screen that is displayed immediately after a specific annotation line is selected in the analysis screen.

FIG. 15 is a diagram illustrating a screen that is displayed immediately after a specific annotation line is selected in the analysis screen. Specifically, FIG. 15 illustrates an entire screen that is displayed immediately after the line 117-7 is selected (for example, double clicked) in the analysis screen illustrated in FIG. 13. When the analyzer focuses attention on the annotation A7 and selects (for example, double clicks) the line 117-7 to analyze waveforms in this region, the analysis display control unit 302 displays enlarged views of signal waveforms near the highlighted signal waveforms in an enlarged display region 200. The analysis display control unit 302 displays enlarged views of the signal waveforms over a certain time range indicated in a region 114, together with a line 217-7 that indicates a temporal position.

Figure 16:
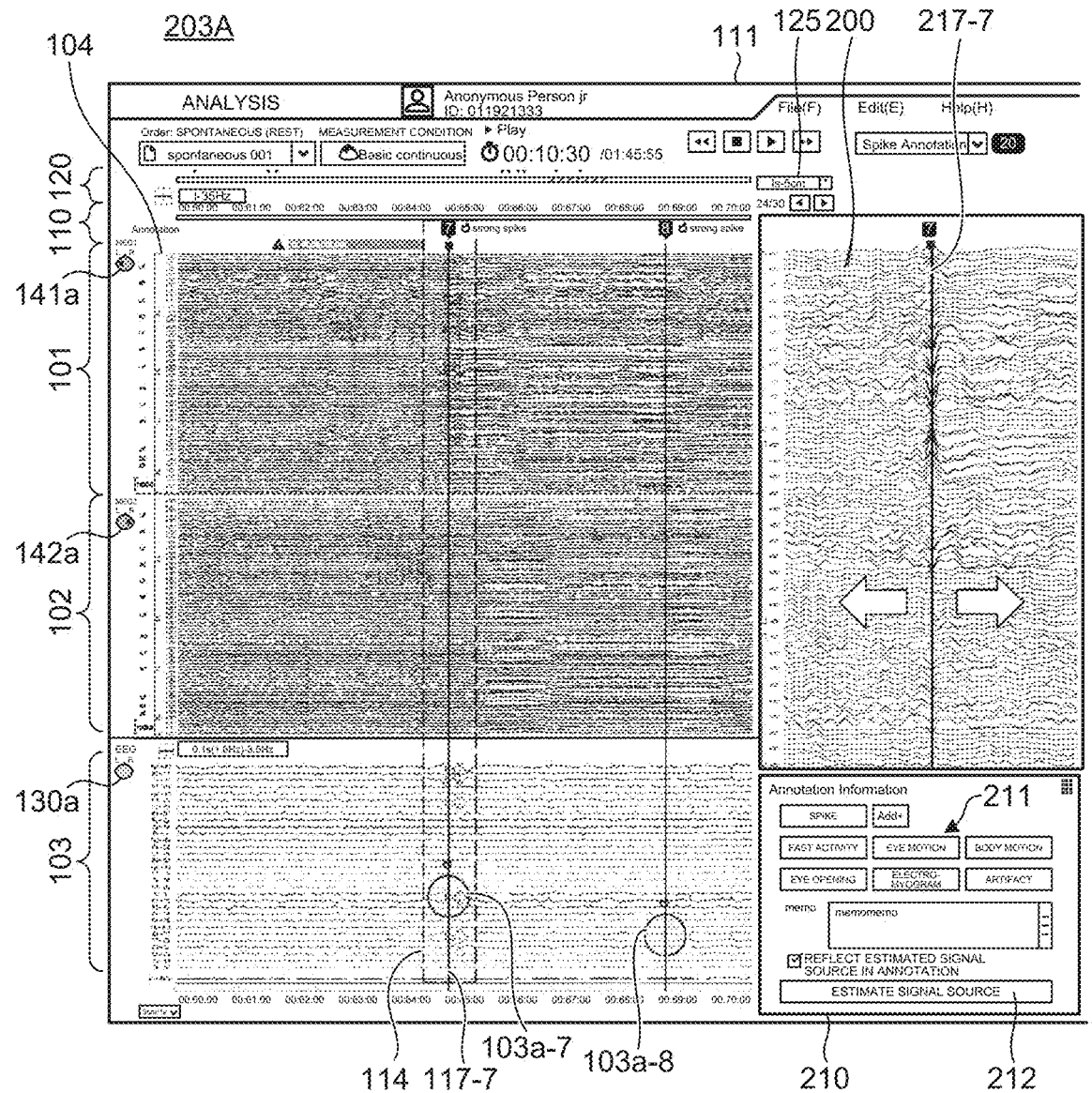
FIG. 16 is an enlarged view of a left-side region of the screen illustrated in FIG. 15.

FIG. 16 is an enlarged view of a left-side region of the screen illustrated in FIG. 15. In other words, FIG. 16 is an enlarged view of a left-side region 203A (a display region for signal waveforms) illustrated in FIG. 15. By displaying the enlarged views of the signal waveforms in the enlarged display region 200, the analyzer is able to reconfirm the validity of the mark that is added at the time of recording or check a waveform portion that has not been checked during measurement and recording. For example, by dragging the line 217-7 to the left or right, it is possible to identify or change an accurate portion of a problematic waveform. It may be possible to reflect, in the enlarged display region 200, the mark 103a-7 and the attribute icon 106-7 (see FIG. 13) that are displayed in a highlighted manner in the display region 103. However, because this may interfere with visual confirmation for accurately determining a singularity of amplitude, it is desirable to allow selection of display or non-display of the highlighted mark 103a-7 and the highlighted attribute icon 106-7 when displaying them in the enlarged display region 200.

It may be possible to specify a type of signal waveforms and a channel range to be displayed in the enlarged display region 200. For example, the analyzer moves the line of sight from the mark 103a-7 that is highlighted in the display region 103 to the upper part of the screen and checks whether a singularity of amplitude is present in the waveforms displayed in any of the display regions 101 and 102 of magnetoencephalography waveforms. In this case, it is possible to display enlarged views of magnetoencephalography waveforms related to the mark 103a-7 in the enlarged display region 200 by specifying a target channel region of the display region 101 or the display region 102 in a box 125.

A confirmation window 210 is displayed below the screen of the enlarged display region 200. The confirmation window 210 includes signal waveform attribute buttons 211 and a signal source estimation button 212. The attribute buttons 211 correspond to pieces of attribute information that are included in the pop-up window 115 of the measurement recording screen, and it is possible to select any of the attribute buttons 211 to select a correct attribute when an attribute that is added at the time of recording is wrong. If a correct position or selection of an attribute of the signal waveform is confirmed, it is possible to reflect estimation of a signal source in the annotation by clicking the estimation button 212. In other words, the information processing apparatus 50 (the analyzing unit 305) of the first embodiment has a function to estimate a signal source corresponding to an annotation that is selected from the analysis screen. As will be described later, the estimated signal source is displayed, in a superimposed manner, on a tomography image that corresponds to the estimated signal source among a plurality of MRI tomography images.

Figure 17:
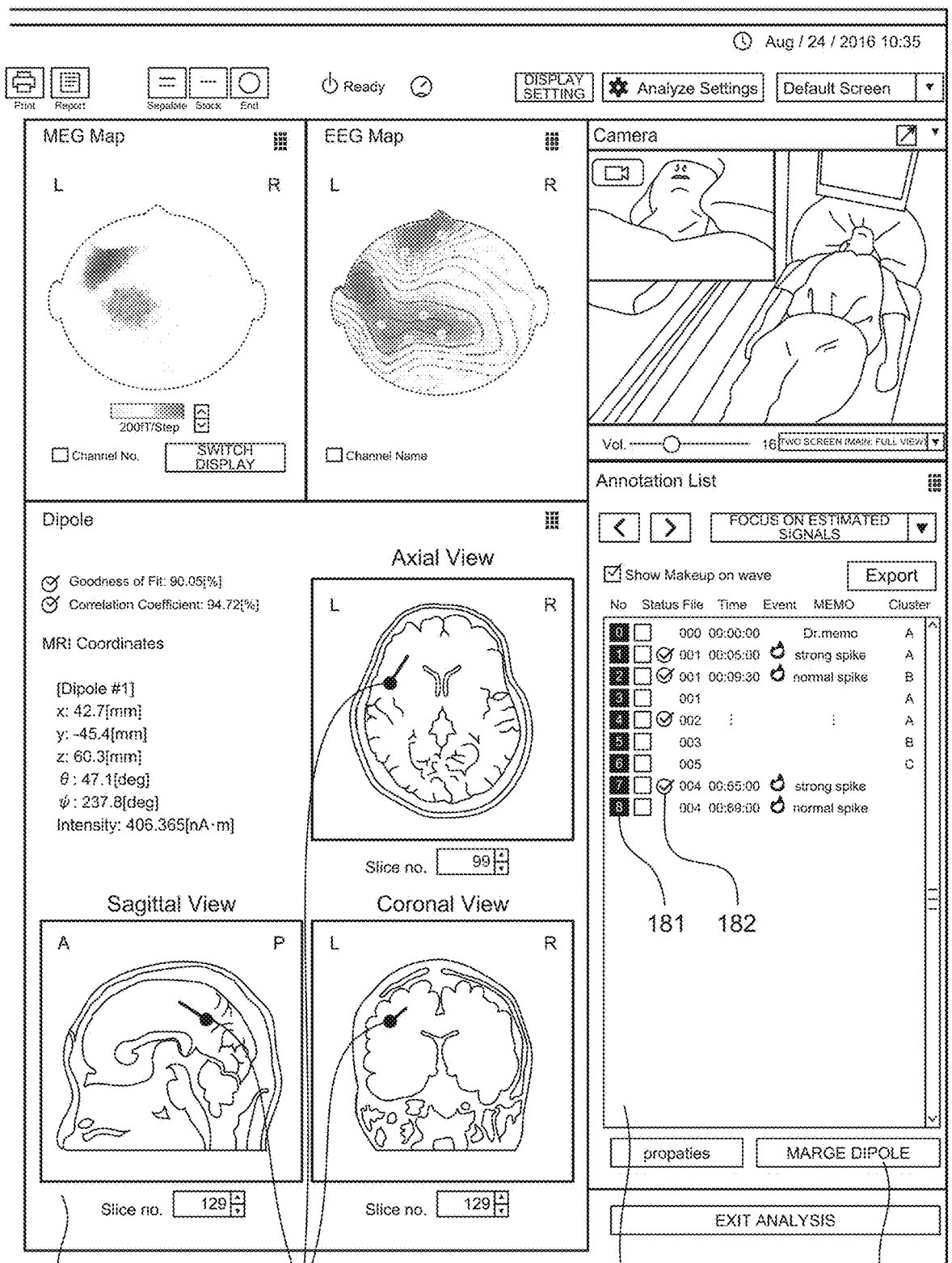
FIG. 17 is an enlarged view of a right-side region of the screen illustrated in FIG. 15.

FIG. 17 is an enlarged view of a right-side region of the screen illustrated in FIG. 15. In other words, FIG. 17 is an enlarged view of a right-side region 203B illustrated in FIG. 15. When the signal waveform position and the attribute for a desired annotation are confirmed and the signal source estimation button 212 is selected in FIG. 16, the estimation completion mark 182 is added to a corresponding annotation (in this example, an annotation number of "7") in the annotation list 180. Further, dipole estimation results 190a are displayed in MRI tomography images in the display window 190.

When the analyzer changes a mark position displayed in a highlighted manner in the display regions 101 to 103 or changes contents of an annotation, the annotation list 180 is updated by one of the following two update methods. That is, one is a method of reflecting latest update information provided by the analyzer in the annotation list 180, and the other is a method of adding new annotation information while maintaining annotation information obtained at the time of measurement and recording. If the latter method is adopted, for example, it may be possible to assign, as annotation identification information, a branch number from the annotation number that is assigned at the time of recording. In this case, it may be possible to add new annotation information in the display region 110 and display the added annotation information in a different color along the time axis.

Figure 20:
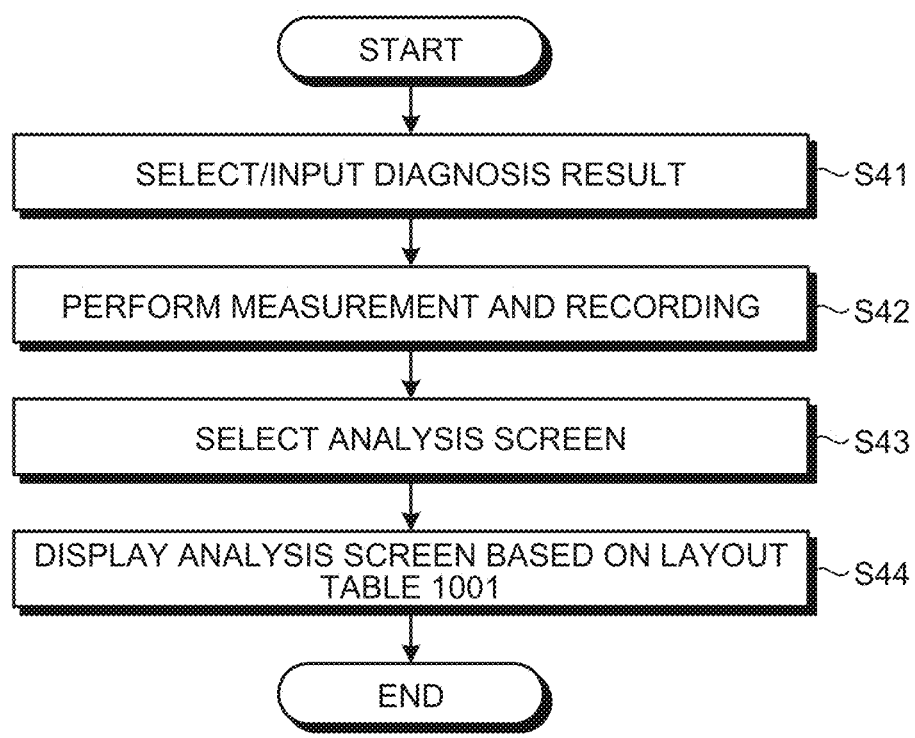
FIG. 20 is a flowchart illustrating operation of changing a layout of the analysis screen.

FIG. 18 is a diagram illustrating an example in which a display region of one of magnetoencephalography signal waveforms in the analysis screen of the first embodiment is enlarged. FIG. 19 is a diagram illustrating an example of a layout table of the first embodiment. FIG. 20 is a flowchart illustrating operation of changing a layout of the analysis screen. Operation performed by the information processing apparatus 50 according to the first embodiment for changing a layout of display contents of the analysis screen will be described below with reference to FIG. 18 to FIG. 20.

As described above, when information measured by magnetoencephalograph or electroencephalograph is to be displayed, in some cases, an appropriate mode of displaying the information in the analysis screen may be substantially determined depending on, for example, the result of a medical examination (including a medical interview) that is performed on a patient in advance. For example, if it is expected that an affected area is present on the left side of the brain as a result of a medical examination, and when the analysis display control unit 302 initially displays the analysis screen, the analysis display control unit 302 displays the display region 101, which displays a magnetoencephalography signal obtained from the left side of the head of the patient (to-be-measured person), in an enlarged manner as illustrated in FIG. 18. In this case, as illustrated in FIG. 18, the analysis display control unit 302 may reduce the vertical width of the display region 102 that displays a magnetoencephalography signal obtained from the right side of the head of the patient, as compared to the vertical width of the display region 101. Further, when displaying the display region 102 in a reduced manner, it may be possible to display all of signals by reducing intervals between the signals corresponding to channels that are selected in the reduced image 142*a*, or may display only signals corresponding to channels after thinning the selected channels. Furthermore, the numbers of sensors (channels) that are displayed on the channel axis 104 of the display region 101 and the display region 102 may be the same and all of the sensors (channels) may be displayed. Meanwhile, if it is expected that there is no affected area in the right side of the brain as a result of the medical examination, the analysis display control unit 302 may hide the display region 102 that displays a magnetoencephalography signal obtained from the right side of the head. Alternatively, if there is no abnormality in the electroencephalography signal, the analysis display control unit 302 may hide the display region 103 that displays an electroencephalography signal. In this case, the analysis display control unit 302 may hide the display region upon receiving information indicating that there is no affected area in the right side of the brain or information indicating that there is no abnormality in the electroencephalography signal.

Details of the above-described operation of changing the layout of display contents of the analysis screen (for example, operation of displaying the display region 101 in an enlarged manner and displaying the display region 102 in a reduced manner as described above) depending on the result of the medical examination (including the medical interview) that is performed on the patient in advance will be described below with reference to FIG. 19 and FIG. 20. First, the information processing apparatus 50 has a layout table for associating a type of the medical examination result on the patient with a type of the layout of the analysis screen. For example, when a user (doctor or the like) of the analysis screen performs operation of inputting a medical examination result (diagnosis result) via the input unit 311 illustrated in FIG. 3, the setting unit 304 sets, in accordance with the input operation, a layout table 1001 (one example of layout information) for associating the medical examination result (including the medical interview result) with a layout content to be displayed in the analysis screen, and stores the layout table 1001 in the storage unit 310 (Step S41). For example, with use of the input unit 311, it may be possible to perform operation of selecting one of options such as a medical examination result in the layout table 1001 or inputting the medical examination result via a menu in the measurement recording screen, or it may be possible to perform the selection operation or the input operation via an input screen that is different from the measurement recording screen. In the example of the layout table 1001 illustrated in FIG. 19, for example, a layout content of "enlarge a magnetoencephalography signal waveform of the right brain and reduce a magnetoencephalography signal waveform of the left brain" is associated with a medical examination result of "affected area is present in the right brain". Meanwhile, while the layout table 1001 is described as information in a table format, embodiments are not limited to this example, and the layout table may be in any format as long as values in a plurality of fields of the layout table can be managed in an associated manner.

Further, when the doctor performs a medical examination on the patient before performing measurement and recording using the measurement recording screen illustrated in FIG. 6, the doctor reflects information on a medical examination result (including a medical interview result) in the patient information that is about the patient and that is stored in the storage unit 353 of the server 40. The patient information may be reflected (updated) by performing input operation on the information processing apparatus 50 or by directly inputting the patient information to the server 40.

Then, after performing measurement and recording on the specific patient (Step S42), the user (doctor or the like) of the analysis screen selects and opens an analysis screen in the information processing apparatus 50 to analyze measurement data (a magnetoencephalography signal, an electroencephalography signal, and the like) on the specific patient (Step S43), and the layout information acquiring unit 308 acquires the patient information (including the medical examination result) associated with the measurement data of the patient from the server 40 via the communication unit 306. The layout determining unit 309 refers to the layout table 1001 stored in the storage unit 310, acquires a layout content corresponding to the medical examination result in the patient information acquired by the layout information acquiring unit 308, and determines the layout content as a layout of the analysis screen. The analysis display control unit 302 constructs an initial layout by changing the layout of the analysis screen that has a basic layout as illustrated in FIG. 12 etc., in accordance with the layout content of the analysis screen determined by the layout determining unit 309, and displays the initial layout (Step S44).

In this manner, by changing the layout of the analysis screen and constructing and displaying the initial layout in accordance with the medical examination (including the medical interview) that is performed on the patient in advance, it is possible to appropriately change the layout of information to be displayed, in accordance with the medical examination result (one example of a specific condition). With this configuration, it is possible to hide information that is not needed based on an observation on the patient and display necessary information in an easily viewable manner, so that is possible to simplify analysis operation.

Meanwhile, it is of course possible for the user to manually change, through input operation, a layout of the initially-displayed analysis screen for which the layout has been changed.

Figure 21:
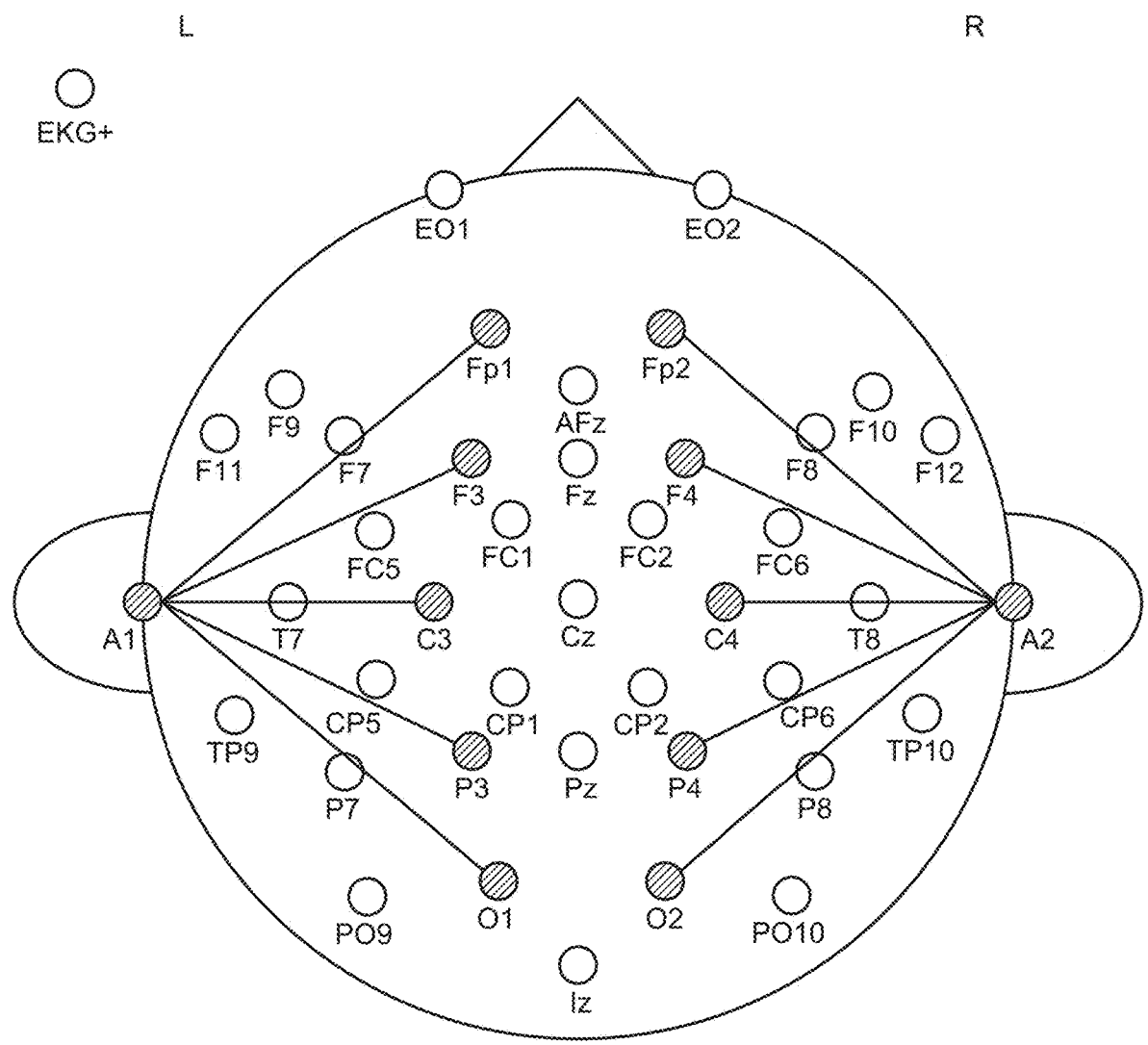
FIG. 21 is a diagram illustrating an example of a monopolar montage.
Figure 22:
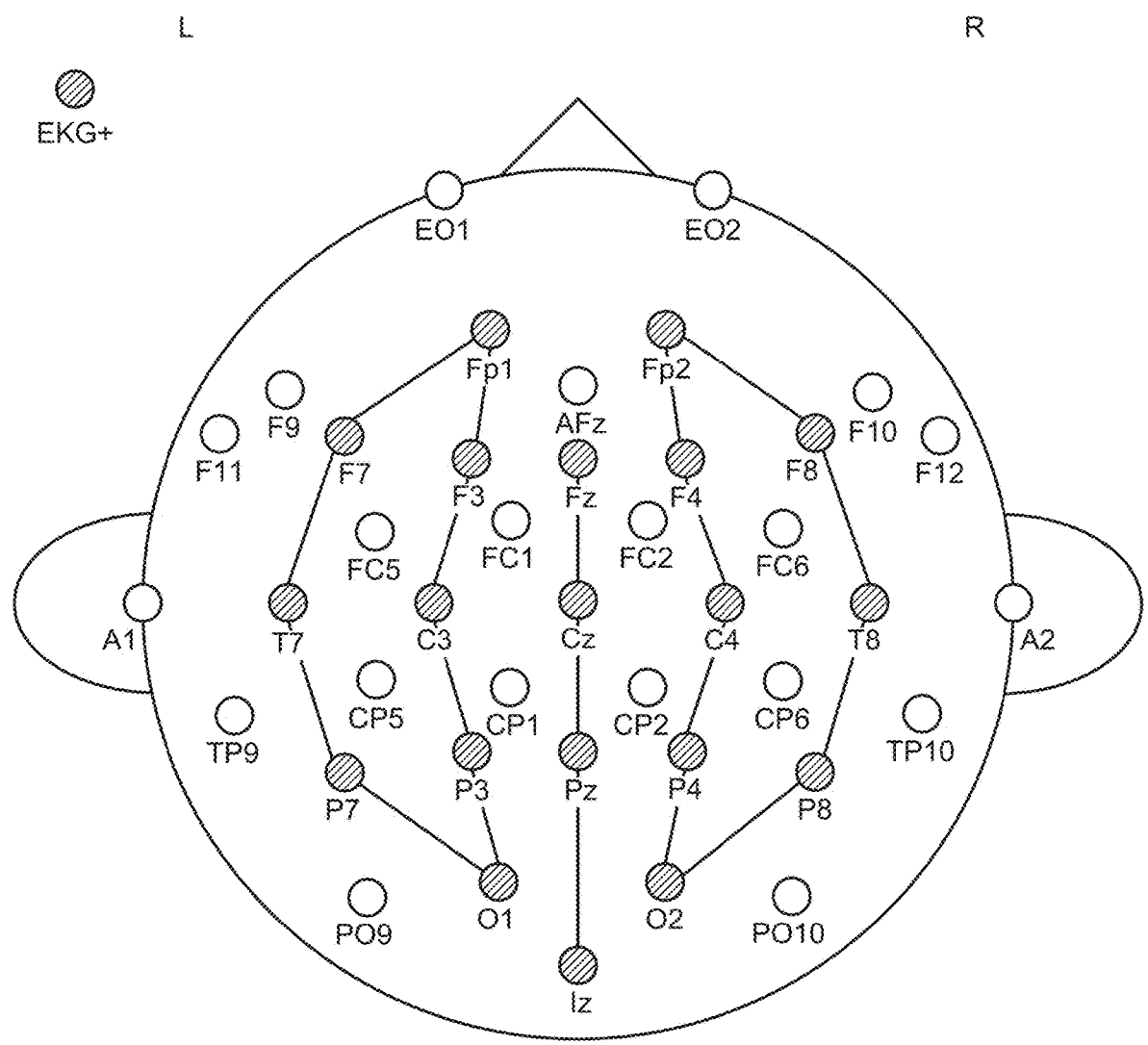
FIG. 22 is a diagram illustrating an example of a longitudinal bipolar montage.
Figure 23:
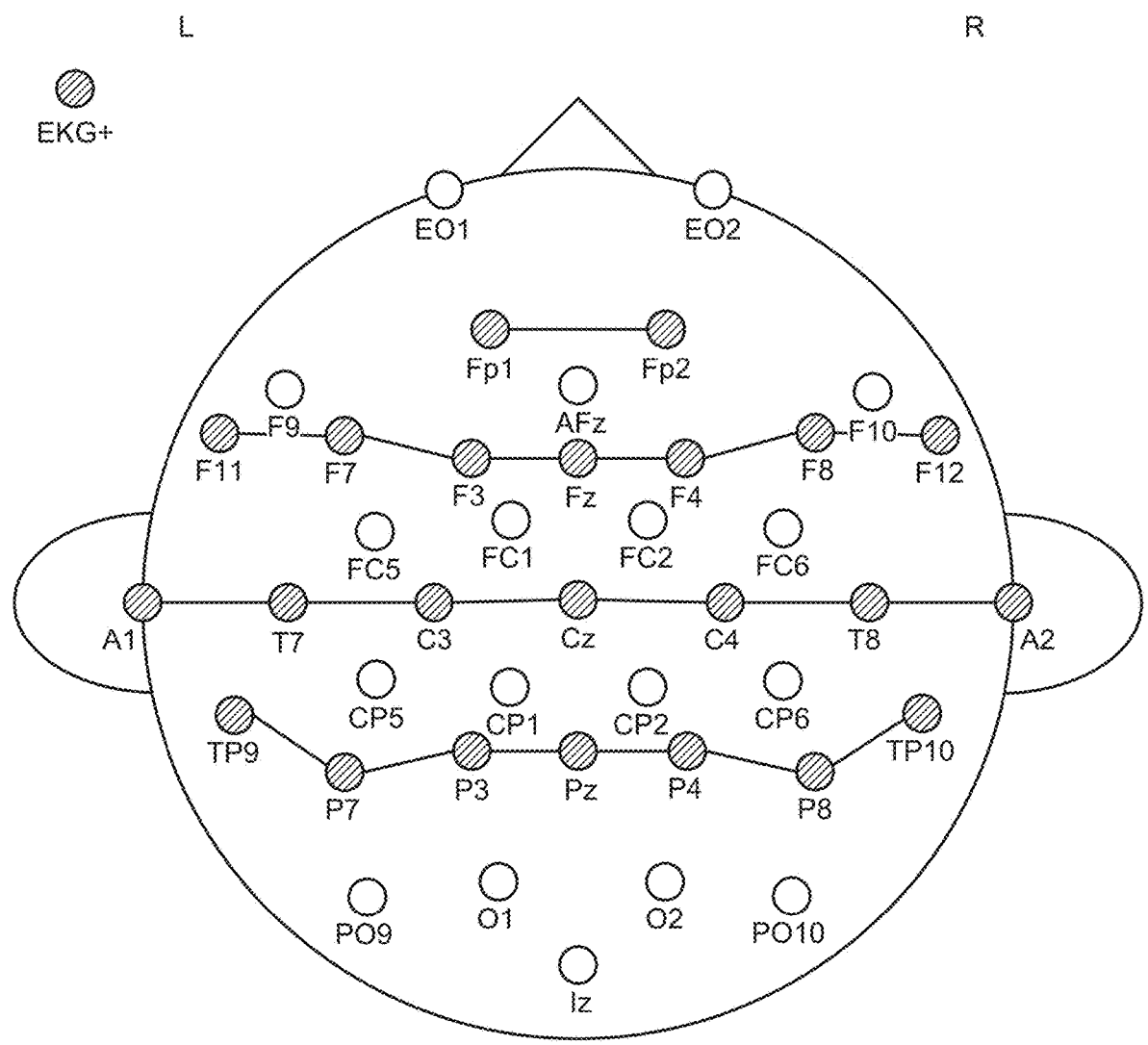
FIG. 23 is a diagram illustrating an example of a transverse bipolar montage.

Further, the details of the layout change described above are mere example, and embodiments are not limited to this example. For example, it may be possible to change the layout by filtering measurement data (a magnetoencephalography signal, an electroencephalography signal, and the like) in accordance with the medical examination result, selecting a specific channel of the magnetoencephalography signal, or displaying an electroencephalography signal with a specific montage pattern (the distribution map 130 illustrated in FIG. 14) in the display region 103 illustrated in FIG. 7. Examples of the montage pattern include a unipolar lead using a common reference electrode (for example, FIG. 21), a longitudinal bipolar lead (for example, FIG. 22) using electrodes between two points on the head, and a transverse bipolar lead (for example, FIG. 23).

Furthermore, while it is explained that the layout is changed by acquiring a layout content associated with a medical examination result from the layout table 1001 on the basis of the medical examination result included in the patient information, embodiments are not limited to this example. For example, it may be possible to associate layout information on a finally customized layout (for example, a layout at the time of terminating the analysis process, or the like) with the patient information or include the layout information in the patient information, with respect to the analysis screen that is opened to analyze the measurement data of a specific patient, and store the patient information with the layout information in the server 40. Then, when the analysis screen is opened again to confirm measurement data of the same patient or the like, the layout of the analysis screen may be changed in accordance with the layout information that is included in the patient information on the patient or that is associated with the patient information.

Figure 24:
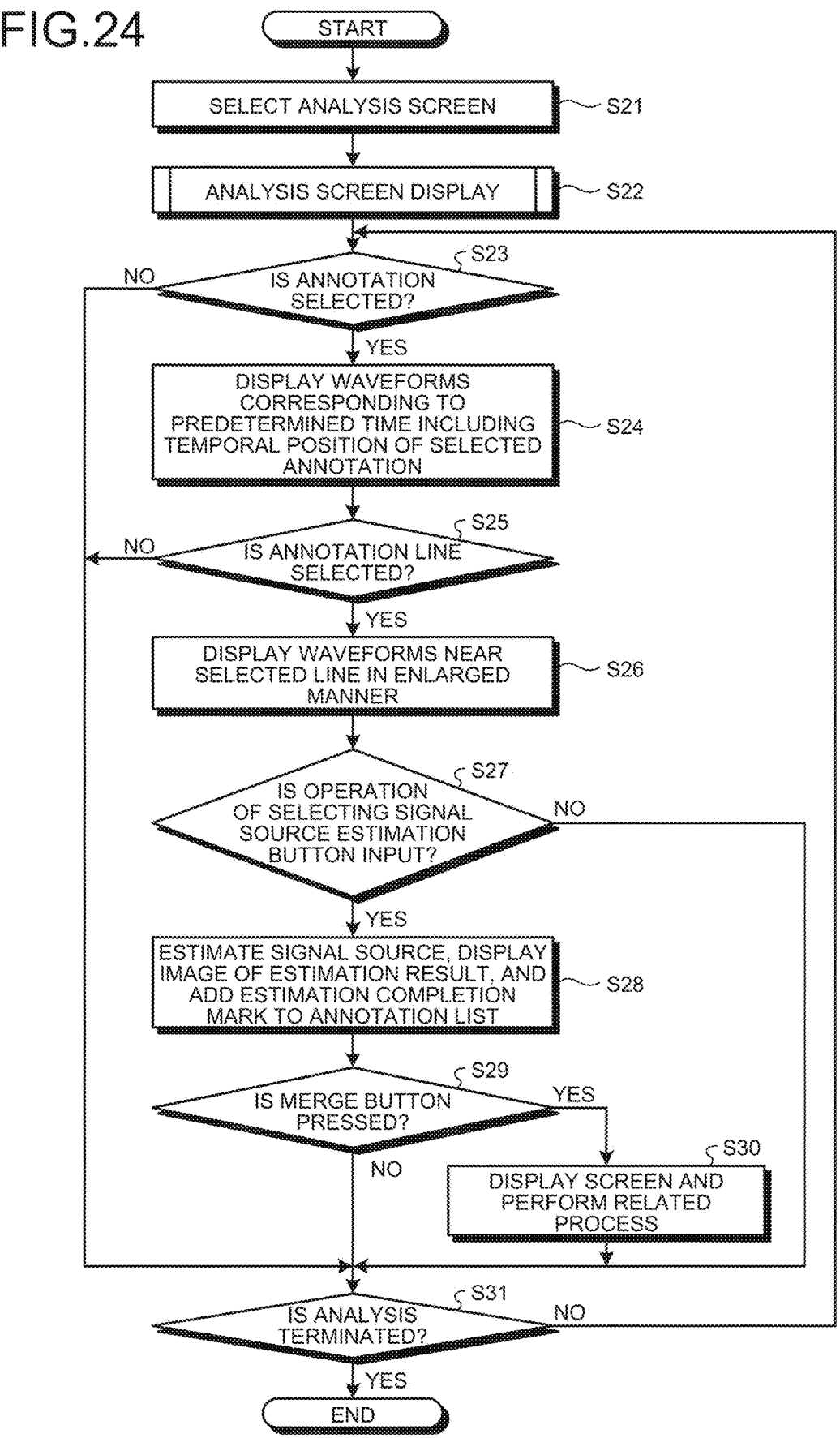
FIG. 24 is a flowchart illustrating operation that is performed by the information processing apparatus at the time of analysis.
Figure 25:
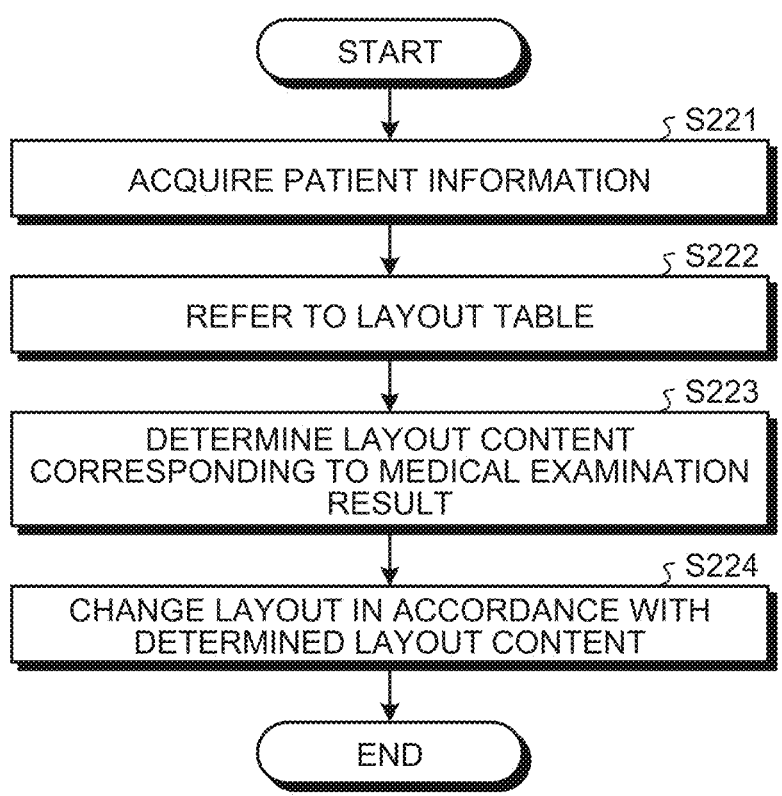
FIG. 25 is a flowchart illustrating operation that is performed at the time of displaying the analysis screen.

FIG. 24 is a flowchart illustrating operation performed by the information processing apparatus at the time of analysis. FIG. 25 is a flowchart illustrating operation that is performed at the time of displaying the analysis screen. When "analysis" is selected in the start screen 204 (see FIG. 5) (Step S21), analysis is started and the analysis screen is displayed (Step S22).

At this time, a layout of initial display of the analysis screen is changed as described below. When the user (doctor or the like) of the analysis screen opens an analysis screen in the information processing apparatus 50 to analyze measurement data (a magnetoencephalography signal, an electroencephalography signal, and the like) on a specific patient, the layout information acquiring unit 308 acquires the patient information (including the medical examination result) associated with the measurement data of the patient from the server 40 via the communication unit 306 (Step S221). Subsequently, the layout determining unit 309 refers to the layout table 1001 stored in the storage unit 310 (Step S222), acquires a layout corresponding to the medical examination result in the patient information acquired by the layout information acquiring unit 308, and determines the layout content as a layout of the analysis screen (Step S223). Then, the analysis display control unit 302 constructs an initial layout by changing the layout of the analysis screen that has a basic layout as illustrated in FIG. 12 etc., in accordance with the layout content of the analysis screen determined by the layout determining unit 309, and displays the initial layout (Step S224).

When the analysis screen is displayed, it is determined whether a specific annotation is selected (Step S23). The annotation may be selected by selecting a specific annotation number or a specific row in the annotation list 180 or by specifying a temporal position by operating the time zone 120b on the time axis 122 in the display region 120. If an annotation is selected (YES at Step S23), signal waveforms corresponding to a predetermined time including the temporal position of the selected annotation are displayed (Step S24).

In the displayed situation, it is determined whether a line 117 indicating a temporal position of a mark displayed in a highlighted manner is selected (Step S25). If the line 117 is selected (YES at Step S25), signal waveforms in a certain time range including the selected line are displayed in an enlarged manner (Step S26). A channel of the waveform displayed in the enlarged display region 200 corresponds to a sensor that is determined at Step S224. Here, it is not always necessary to display enlarged views of signal waveforms that are present near the mark being displayed in a highlighted manner in the enlarged display region 200, but it may be possible to display enlarged views of signal waveforms of a different kind that are present at the same temporal position. For example, when a mark displayed in a highlighted manner is added to electroencephalography signal waveforms, it may be possible to display enlarged views of magnetoencephalography signal waveforms that are present at the same temporal position. Further, it may be possible to display enlarged views of signal waveforms that are acquired by channels in a certain range including a channel that has acquired the marked signal waveform, instead of displaying enlarged views of signal waveforms of all of the channels. In this case, it may be possible to determine a type of signal waveforms to be displayed in an enlarged manner or determine whether designation of a channel range is input or not.

Subsequently, it is determined whether the signal source estimation button 212 is pressed (Step S27). If the signal source estimation button 212 is pressed (YES at Step S27), calculation for estimating a signal source is performed. An estimation result is displayed on an MRI tomography screen and the estimation completion mark 182 is added to the annotation list 180 (Step S28). Then, if operation of pressing a merge button 185 (see FIG. 17) that is arranged below the annotation list 180 is received (YES at Step S29), the merge display control unit 303 of the information processing apparatus 50 displays the merge screen 400 (to be described later) and performs a process related to the merge screen 400 (Step S30). Details of Step S29 and Step S30 will be described later. If operation of pressing the merge button 185 is not received (NO at Step S29), or after Step S30, it is determined whether an analysis termination command is input (Step S31). If an annotation is not selected (NO at Step S23), if an annotation line for displaying an enlarged view is not selected (NO at Step S25), or if operation of pressing the signal source estimation button 212 is not received (NO at Step S27), the process proceeds to Step S31 and it is determined whether to terminate the analysis. Steps S23 to S30 are repeated until the analysis termination command is input (YES at Step S31).

Meanwhile, it may be possible to determine whether an annotation is changed between Step S26 and Step S27. If an annotation is changed, this change is reflected in the annotation list 180, and the process proceeds to the determination at Step S27.

Through the display processing operation as described above, it is possible to display information with excellent visibility and operability.

As described above, signal sources are sequentially estimated through analysis by the analyzing unit 305, and when operation of pressing the merge button 185 that is arranged below the annotation list 180 is received, the merge display control unit 303 displays, in a superimposed manner, a signal source that corresponds to a part of biological data that indicates a temporal change of a biological signal on biological tomography images that are images sliced in a predetermined direction, and initially displays a biological tomography image on which a predetermined signal source is superimposed among the plurality of sliced biological tomography images in the display region. Here, the predetermined signal source is a signal source that meets a predetermined condition. In this example, the predetermined condition is the number of signal sources, but embodiments are not limited to this example. In the first embodiment, the predetermined signal source is a signal source that is most observed among the signal sources in each of the sliced biological tomography images. While details will be described later, the merge display control unit 303 initially displays a biological tomography image including the largest number of signal sources near the center of the display region. Then, the merge display control unit 303 displays the other biological tomography images such that the biological tomography images are arranged in a slice sequence on the left and right of the biological tomography image arranged near the center. Further, the merge display control unit 303 is able to display a biological tomography image on which a signal source is not superimposed, or hide a biological tomography image on which a signal source is not superimposed. This will be described in detail below.

In the first embodiment, when receiving operation of pressing the merge button 185 that is arranged below the annotation list 180 illustrated in FIG. 17, the merge display control unit 303 displays the merge screen 400 as illustrated in FIG. 26 on the display device 507. The merge screen 400 includes a region 401A for displaying a plurality of biological tomography images side by side in the horizontal direction, and a region 401B for displaying tomographic positions of biological tomography images that are selected from the region 401A.

The region 401A includes a display region 410A for displaying tomography images viewed from above (hereinafter, may be referred to as "slice images A" in some cases), a display region 410B for displaying tomography images viewed from a lateral direction (hereinafter, may be referred to as "slice images B" in some cases), and a display region 410C for displaying tomography images viewed from a backside direction (hereinafter, may be referred to as "slice images C" in some cases). In the following description, the slice images A, B, and C may be collectively referred to as a "slice image" when they need not be distinguished from one another. Meanwhile, vertical arrangement directions of the tomography images in the region 401A are not limited to the example of the first embodiment.

Figure 27:
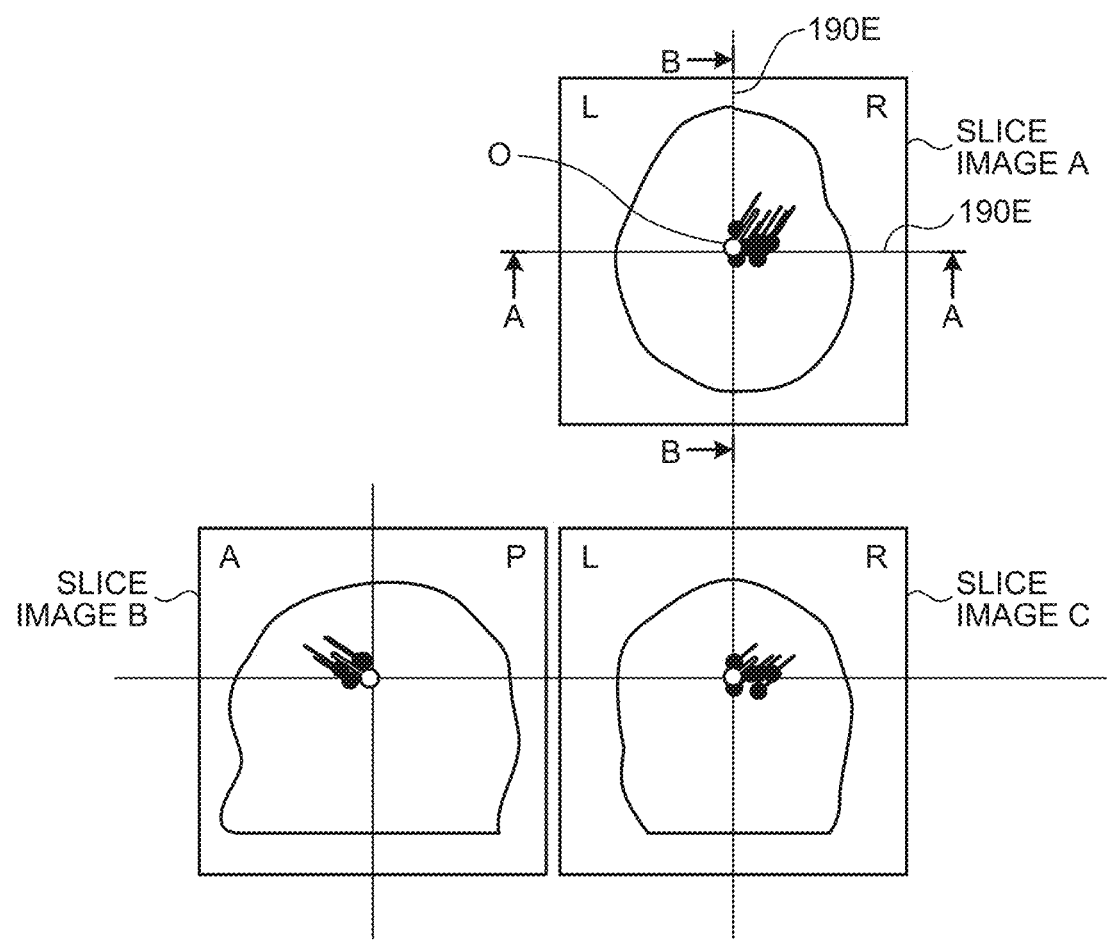
FIG. 27 is a diagram for explaining a relationship among three slice images corresponding to three-dimensional directions.

Here, a relationship among the slice image A, the slice image B, and the slice image C corresponding to the three-dimensional directions will be described with reference to FIG. 27. In FIG. 27, positions of the slice images A to C are linked in the three-dimensional directions. Reference lines 190E are displayed across each of the slice images, and an intersection O of the reference lines 190E displays a tomographic position of each of the slice images. In this example, the slice image C is a cross-sectional view of a section that is cut along the reference line 190E in the horizontal direction (left-right direction) in the slice image A and that is viewed in a direction A illustrated in FIG. 27. Further, the slice image B is a cross-sectional view of a section that is cut along the reference line 190E in the vertical direction in the slice image A and that is viewed in a direction B illustrated in FIG. 27. In the following description, a viewpoint corresponding to the slice image A is referred to as an "axial view", a viewpoint corresponding to the slice image B is referred to as a "sagittal view", and a viewpoint corresponding to the slice image C is referred to as a "coronal view".

In other words, in this example, the biological tomography image includes a first tomography image (for example, the slice image A) that is a cross section in a first direction, a second tomography image (for example, the slice image B) that is a cross section in a second direction perpendicular to the first direction, and a third tomography image (for example, the slice image C) that is a cross section in a third direction perpendicular to the first direction and the second direction.

Referring back to FIG. 26, explanation is continued. The merge display control unit 303 displays information indicating the number of superimposed signal sources, together with a corresponding biological tomography image. In each of the display regions 410A to 410C, information 440A on a slice number that indicates a tomographic position of the image and information 440B on the number of signal sources (the number of dipole estimation results) that are superimposed on the slice image are displayed in each of the slice images.

The region 401B includes a display region 420A corresponding to the display region 410A, a display region 420B corresponding to the display region 410B, and a display region 420C corresponding to the display region 410C.

The display region 420A displays information indicating at which positions in a tomography image viewed from side (a left-side image in the display region 420A) and a tomography image viewed from back (a right-side image in the display region 420A) the slice images A displayed in the display region 410A are sliced, and displays tomographic position lines 450 indicating the tomographic positions in a superimposed manner. Each of the adjacent tomographic position lines 450 between a slice position A viewed from side and a slice position B viewed from back are located at the same position in the vertical direction in the figure. Further, slice numbers corresponding to the respective tomographic position lines 450 are associated with the slice images A displayed in the display region 410A. For example, slice numbers 01 to 15 are assigned from the bottom to the top of the display region 420A.

Similarly, the display region 420B displays information indicating at which positions in a tomography image viewed from above (a left-side image in the display region 420B) and a tomography image viewed from back (a right-side image in the display region 420B) the slice images B displayed in the display region 410B are sliced, and displays the tomographic position lines 450 indicating the tomographic positions in a superimposed manner. The tomographic position lines 450 at a slice position C viewed from above and at a slice position D viewed from back are located at the same positions in the horizontal direction in the figure. Further, slice numbers corresponding to the respective tomographic position lines 450 are associated with the slice images B displayed in the display region 410B. For example, slice numbers 01 to 14 are assigned from left to right of the display region 420B.

Similarly, the display region 420C displays information indicating at which positions in a tomography image viewed from above (a left-side image in the display region 420C) and a tomography image viewed from side (a right-side image in the display region 420C) the slice images C displayed in the display region 410C are sliced, and displays the tomographic position lines 450 indicating the tomographic positions in a superimposed manner. Top-to-bottom positions of the tomographic position line 450 at a slice position E viewed from above and left-to-right positions of the tomographic position lines 450 at a slice position F viewed from side correspond to one another. Further, slice numbers corresponding to the respective tomographic position lines 450 are associated with the slice images C displayed in the display region 410C. For example, slice numbers 01 to 15 are assigned from top to bottom of the display region 420C (in the case of the left tomography image viewed from above) or from left to right of the display region 420C (in the case of the right side tomography image viewed from side).

In other words, the merge display control unit 303 displays information indicating the tomographic positions of the biological tomography images displayed in the region 401A (display region). In this example, the merge display control unit 303 displays information indicating the tomographic positions of biological tomography images that are selected from among a plurality of biological tomography images (slice images). Meanwhile, each of the tomographic position lines 450 as described above and the information 440A indicating the slice numbers as described above are stored in a storage device (the auxiliary storage device 504 or the like) in an associated manner.

In this example, a slice image, in which the largest number of dipole estimation results is displayed in a superimposed manner, is arranged in the center among the slice images displayed in each of the display regions 410A to 410C. Further, other slice images are arranged such that the slice images are arranged in numerical order of the slice number (in a slice sequence) on the left and right of the central slice image. For example, in the display region 410A, a slice image with a slice number 10 is arranged in the center, and slice images with slice numbers 11, 12, and 13 (only a part) are arranged in this order on the right side of the slice image with the slice number 10. Further, slice images with slice numbers 9, 8, and 7 (only a part) are arranged in this order on the left side of the slice image with the slice number 10. In the display region 410B, a slice image with the slice number 10 is arranged in the center, and slice images with slice numbers 11, 12, and 13 (only a part) are arranged in this order on the right side of the slice image with the slice number 10. Further, slice images with slice numbers 9, 8, and 7 (only a part) are arranged in this order on the left side of the slice image with the slice number 10. In the display region 410C, a slice image with a slice number 7 is arranged in the center, and slice images with the slice numbers 8, 9, and 10 (only a part) are arranged in this order on the right side of the slice image with the slice number 7. Further, slice images with slice numbers 6, 5, and 4 (only a part) are arranged in this order on the left side of the slice image with the slice number 7. Here, the center is a center in the width direction of the region 401A (corresponding to a "display region"). Further, for example, it may be possible to display a title (axial view, sagittal view, or coronal view) above the slice image having the largest number of dipole estimation results as illustrated in FIG. 26 to allow an analyzer to visually easily find the slice image. In this case, it may be possible to move the tile in a linked manner when the analyzer scrolls the slice image in the horizontal direction from the initial display state to display a different slice image. By moving the title in a linked manner, it is possible to easily find the slice image having the largest number of dipole estimation results after the scrolling. In contrast, if a direction of the tomography image is focused on, it is preferable to fix the title even when scrolling is performed.

Meanwhile, in the first embodiment, the slice images A displayed in the display region 410A, the slice images B displayed just below the slice images A, and the slice images C displayed just below the slice images B are not associated with one another in the three-dimensional directions. In other words, in each of the display regions 410A to 410C, a slice image, in which the largest number of the dipole estimation results 190*a* is displayed in a superimposed manner, is arranged in the center among the plurality of slice images displayed in the display region 410, and other slice images are arranged such that the slice images are arranged in numerical order of the slice number on the left and right of the central slice image. With this display, it is possible to visually recognize the spread of the dipole estimation results 190*a* from the center to the left and right.

Further, the information 440B indicating the number of dipole estimation results is also displayed in each of the slice images, so that it is possible to concurrently check the amount of dipole estimation results superimposed in each of the slice images. Furthermore, it is possible to recognize whether the dipole estimation results are present within a predetermined range (for example within 1 millimeter (mm)) on the basis of the tomographic position lines 450 in the region 401B and the information 440A indicating the slice number of the selected (focused) slice image. Moreover, if it is difficult to display all of the slice images in the region 401A, it may be possible to display a new slice image by, for example, scrolling the slice image in the horizontal direction by a mouse. In other words, the merge display control unit 303 is able to display a new slice image by moving the slice image in the horizontal direction in accordance with operation of forwarding or returning the slice image (operation for scrolling).

Figure 28:
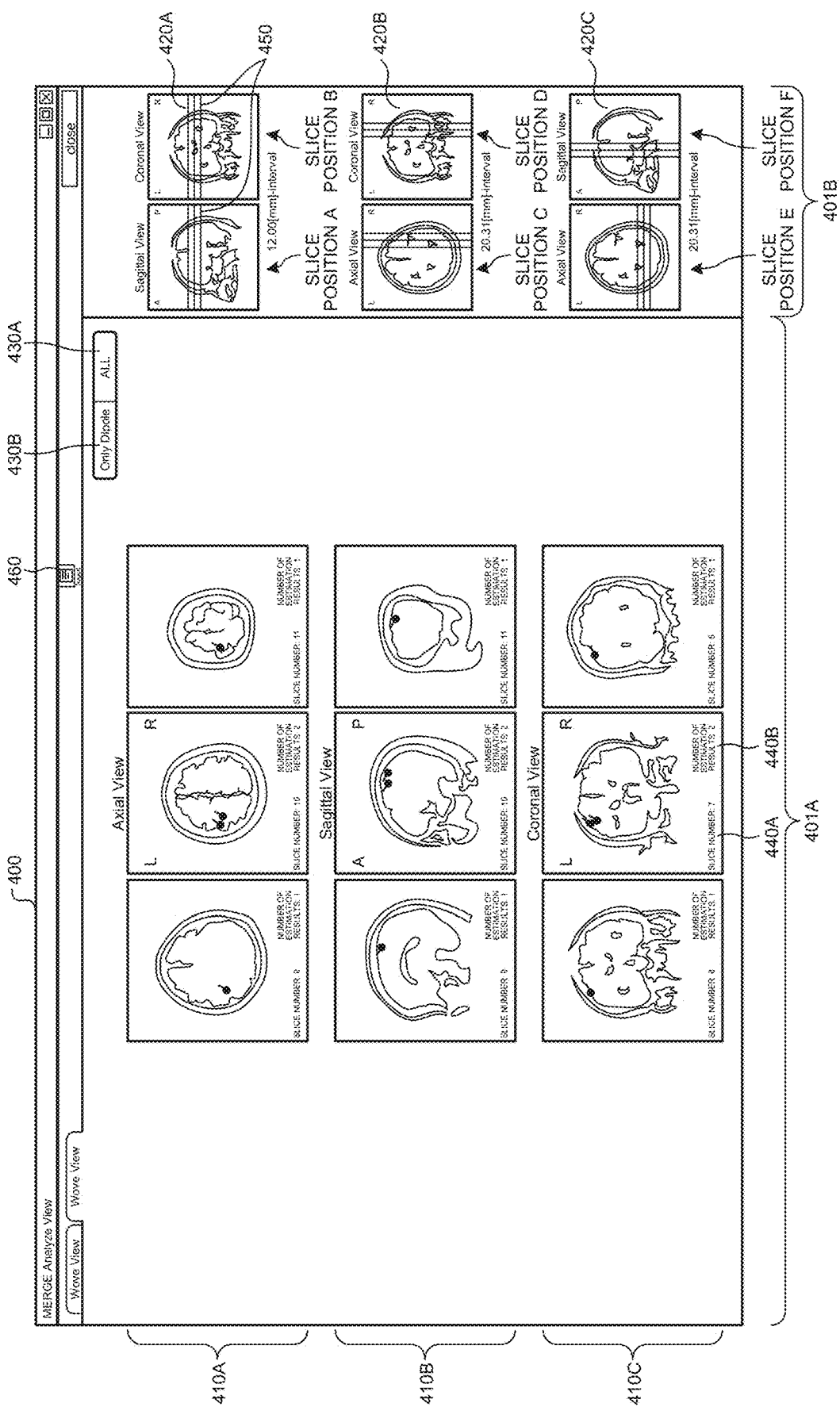
FIG. 28 is a diagram illustrating an example of a screen that is displayed when an "only dipole" button is pressed.
Figure 29:
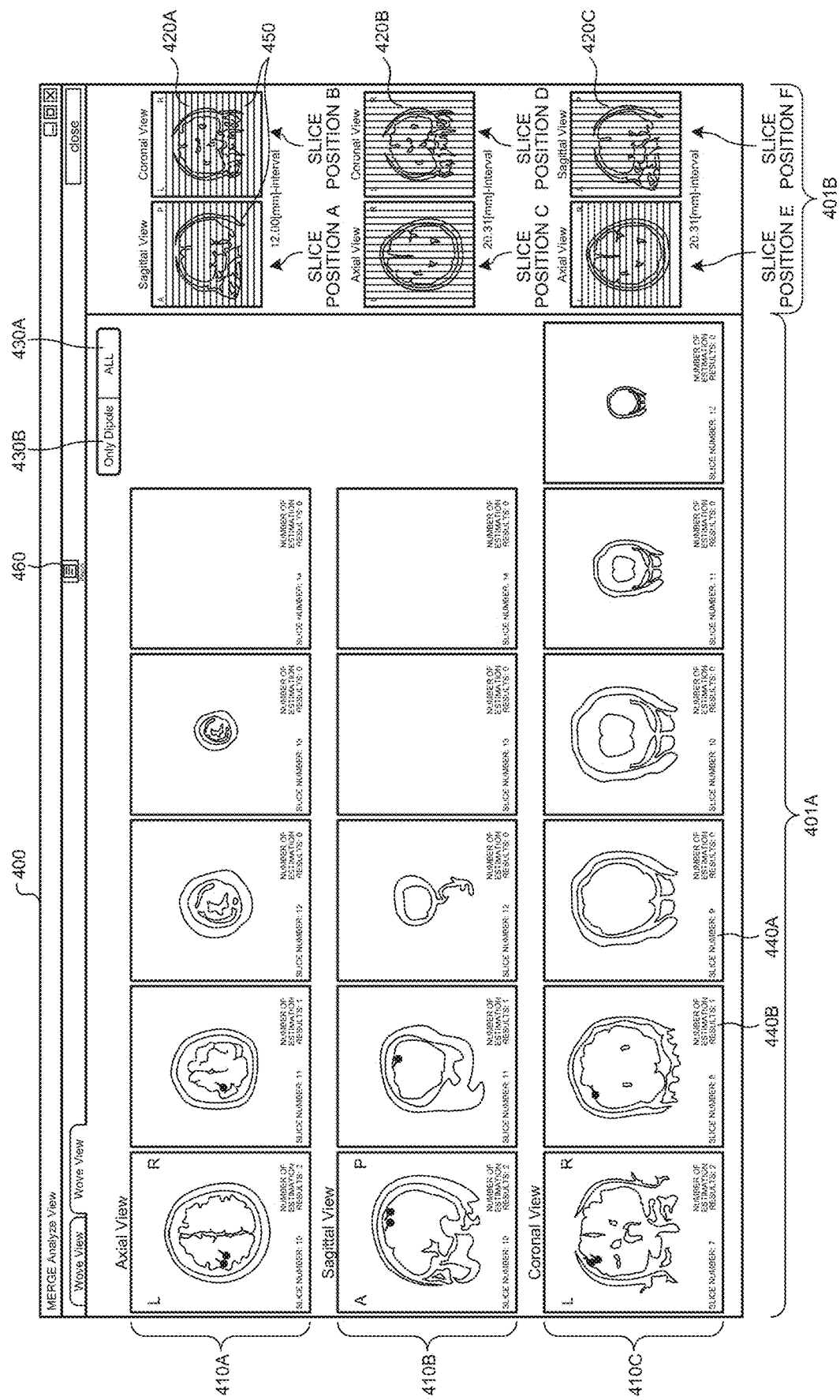
FIG. 29 is a diagram illustrating another example of the screen that is displayed when the merge button is pressed.

Furthermore, in this example, an "only dipole" button 430B, which is for selecting a mode for displaying only a slice image in which a diploe estimation result is displayed in a superimposed manner, and an "all" button 430A, which is for selecting a mode for displaying all of the slice images including a slice image on which a diploe estimation result is not superimposed, are arranged above the display region 410A. FIG. 26 is a diagram illustrating an example of the merge screen 400 that is displayed when the "all" button 430A is pressed. FIG. 28 is a diagram illustrating an example of the merge screen 400 that is displayed when the "only dipole" button 430B is pressed. As illustrated in FIG. 28, only slice images in which dipole estimation results are displayed in a superimposed manner are displayed in the region 401A, and the tomographic position lines 450 corresponding to slice images on which dipole estimation results are not superimposed are hidden in the region 401B. In other words, only the tomographic position lines 450 corresponding to the slice images on which the dipole estimation results are superimposed are displayed. In this manner, by comparing the slice images of interest and the corresponding tomographic position lines 450 on the same screen, it is possible to easily recognize distances between the positions of the dipole estimation results.

The analyzer is able to verify a position at which the largest number of dipole estimation results is present from the slice images in which the dipole estimation results are displayed in a superimposed manner. Then, when an output button 460 is pressed, the slice images in which the dipole estimation results are displayed in a superimposed manner are output (the merge screen 400 at this time is output) and printed out. In this manner, it is possible to more precisely identify a three-dimensional position of a signal source (dipole estimation result) as compared to the conventional technique.

As described above, at least a slice image having the largest number of signal sources is displayed as initial display by adopting a condition that a slice image has the largest number of signal sources as a condition of a slice image to be initially displayed in the region 401A. In this example, as described above, the merge display control unit 303 initially displays a slice image having the largest number of signal sources near the center of the region 401A, and displays other slice images such that the other slice images are arranged in a slice sequence on the left and right of the slice image arranged near the center. With this display, it is possible to visually recognize the spread of the signal sources from the center to the left and right, so that it is possible for an analyzer to improve accuracy for identifying a target portion that may be a cause of symptoms. Further, it is possible to confirm presence or absence of a signal source between adjacent slice images.

Meanwhile, for example, it may be possible to generate slice images on which signal sources are superimposed by superimposing signal sources (group) on all of the slice images, and then select a signal-source-superimposed slice image on which the largest number of signal sources is superimposed. The merge display control unit 303 may be provided with the above-described function to select the signal-source-superimposed slice image on which the largest number of signal sources is superimposed, but embodiments are not limited to this example. For example, it may be possible to provide the above-described function separately from the merge display control unit 303. In other words, a function (selecting unit) to select a biological tomography image that meets a predetermined condition (a biological tomography image that is initially displayed in the region 401A) may be provided separately from the merge display control unit 303. Meanwhile, the above-described function (selecting unit) may be implemented by software (for example, may be implemented by causing the CPU 501 to execute a program) or may be implemented by a dedicated hardware circuit.

Furthermore, for example, it may be possible to identify signal sources (group) that are present in each of the slice images, select a slice image having the largest number of signal sources from identification results, and thereafter display the signal sources on the selected slice image in a superimposed manner. Meanwhile, for example, it may be possible to initially display the slice image selected as above (the slice image having the largest number of signal sources) without superimposing the signal sources, and display information indicating the signal sources (group) or the number of the signal sources in a superimposed manner at an arbitrary timing. Further, it may be possible to display the information indicating the signal sources (group) or the number of the signal sources in a scrolled manner in the display region, in addition to the superimposed display. In this case, even a slice image in which a signal source is not displayed in a superimposed manner can be regarded as a slice image with which a signal source is potentially associated, so that when this slice image is displayed, this display can be regarded as one example of a mode in which "a biological tomography image on which a predetermined signal source is superimposed is initially displayed in the display region".

Figure 30:
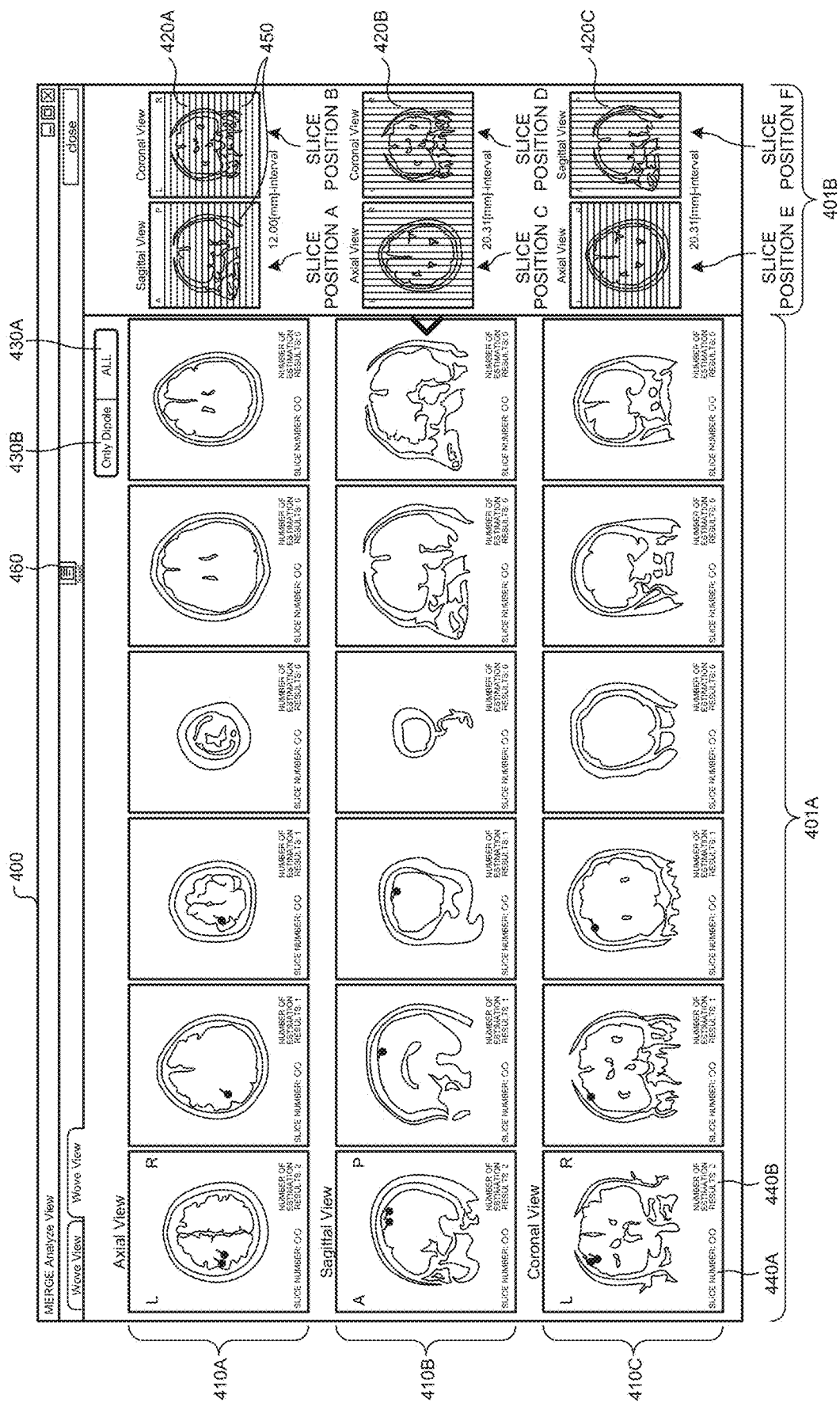
FIG. 30 is a diagram illustrating still another example of the screen that is displayed when the merge button is pressed.

Types of display of the merge screen 400 will be described below with reference to FIG. 30 to FIG. 33. First, as illustrated in FIG. 30, slice images are displayed in each of the display regions 410A to 410C such that a slice image in which the largest number of dipole estimation results is displayed in a superimposed manner is arranged on the left side. Further, other slice images are arranged in numerical order of the slice number (in a slice sequence) on the left and right of the slice image arranged on the leftmost side, similarly to the example illustrated in FIG. 26. If the same slice number as in the example in FIG. 26 is assigned to the slice image having the largest number of dipole estimation results, the state as illustrated in FIG. 30 is obtained. For example, in the display region 410A, the slice image with the slice number 10 is arranged on the leftmost side, and the slice images with the slice numbers 11, 12, 13, and 14 are arranged in this order on the right side of the slice image with the slice number 10. Further, in the display region 410B, the slice image with the slice number 10 is arranged on the leftmost side, and the slice images with the slice numbers 11, 12, 13, and 14 are arranged in this order on the right side of the slice image with the slice number 10. Furthermore, in the display region 410C, the slice image with the slice number 7 is arranged on the leftmost side, and the slice images with the slice numbers 8, 9, 10, 11, and 12 are arranged in this order on the right side of the slice image with the slice number 7.

In this manner, by arranging the slice image having the largest number of dipole estimation results on the leftmost side, it becomes possible to more easily find the slice image having the largest number of dipole estimation results.

Furthermore, for example, it may be possible to arrange slice images (biological tomography images) in a predetermined direction in descending order of the number of signal sources superimposed on the slice images, as the condition of slice images that are initially displayed in the region 401A. In other words, the merge display control unit 303 may adopt the slice image having the largest number of signal sources (a biological tomography image on which a predetermined signal source is superimposed) as a reference image, and arrange and display other biological tomography images in a predetermined direction in descending order of the number of signal sources. For example, as illustrated in FIG. 30, the merge display control unit 303 may arrange the slice image having the largest number of superimposed signal sources on the leftmost side, and arrange and display other slice images such that the number of superimposed signal sources decreases from left to right (one example of the predetermined direction). This type has an advantage in terms of visibility when only checking the number of signal sources (the number of dipole estimation results) on the slice images because it is only necessary to move the line of sight in a single direction from left to right of the region 401A, as compared to the example illustrated in FIG. 26 etc. Moreover, similarly to the example illustrated in FIG. 26, it may be possible to arrange the slice image having the largest number of signal sources in the center, and arrange other slice images on the left and right such that the number of signal sources is gradually decreased.

Figure 31:
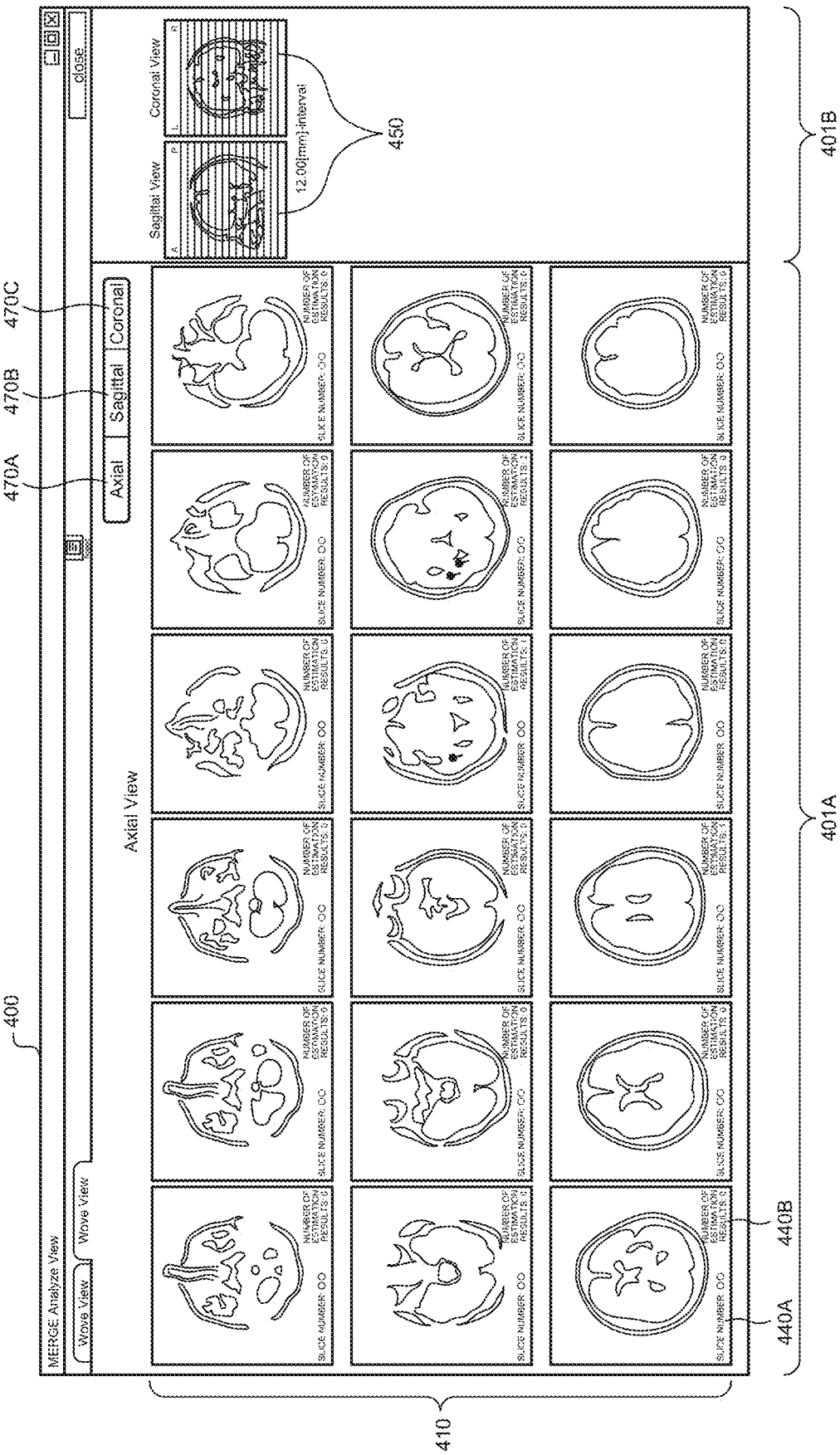
FIG. 31 is a diagram illustrating still another example of the screen that is displayed when the merge button is pressed.

Further, the merge display control unit 303 may display slice images in only a single direction and hide slice images in the other two directions. For example, if slice images are displayed in line in a single direction in the region 401A, visibility of the slice images in the single direction is improved. Furthermore, when a large number of slice images are present, and if tomography images in a single direction are displayed over a plurality of rows as illustrated in FIG. 31, it is possible to reduce the number of times of scrolling, so that it is possible to more effectively recognize the entire image and improve the visibility. FIG. 31 illustrates an example in which a slice image having the largest number of signal sources is arranged in the center, other slice images are arranged on the left and right sides such that the number of signal sources is gradually reduced, and the screen is scrolled after the initial display. Meanwhile, in the example illustrated in FIG. 31, a button 470A for selecting a direction corresponding to the slice images A (direction of "axial view"), a button 470B for selecting a direction corresponding to the slice images B (direction of "sagittal view"), and a button 470C for selecting a direction corresponding to the slice images C (direction of "coronal view") are arranged above the display region 410 in which the slice images in only a single direction are displayed. The merge display control unit 303 displays only a group of the slice images A when receiving operation of pressing the button 470A, displays only a group of the slice images B when receiving operation of pressing the button 470B, and displays only a group of the slice images C when receiving operation of pressing the button 470C.

Further, while the slice images A displayed in the display region 410A, the slice images B displayed just below the slice images A, and the slice images C displayed just below the slice images B are not associated with one another in the three-dimensional directions in the example illustrated in FIG. 26, it may be possible to adopt a mode in which the slice images A displayed in the display region 410A, the slice images B displayed just below the slice images A, and the slice images C displayed just below the slice images B are associated with one another in the three-dimensional directions. In this case, any of the display regions 410A to 410C is adopted as a reference, a slice image having the largest number of superimposed signal sources among the plurality of slice images displayed in the reference display region 410 is arranged and displayed in the center, other slice images are arranged and displayed such that they are arranged in a slice sequence (in numerical order of the slice number) on the left and right of the central slice image, and thereafter slice images in the other display regions 410 are displayed in an associated manner. For example, when the display region 410A is adopted as a reference, a slice image having the largest number of superimposed signal sources among the slice images displayed in the display region 410A is arranged and displayed in the center, and other slice images are arranged and displayed such that they are arranged in a slice sequence on the left and right of the central slice image. Then, each of the slice images displayed in each of the other display regions 410B and 410C is displayed in association with each of the slice images that are displayed in the display region 410A. In this manner, by displaying three slice images that are three-dimensionally associated with one another such that the slice images are aligned in the vertical direction, it is possible to recognize a three-dimensional position of the dipole estimation result (signal source). Further, it may be possible to arrange the slice image having the largest number of dipole estimation results among a plurality of slice images that are displayed in the reference display region 410 on the leftmost side as illustrated in FIG. 30.

Furthermore, it may be possible to combine and superimpose, in a predetermined slice image, each of signal sources that are superimposed on a plurality of slice images, and display the predetermined slice image in the region 401A. For example, a plurality of slice images are divided into groups of ten slice images in numerical order of the slice number, and a total number of signal sources corresponding to the slice images included in each of the groups is calculated. Subsequently, the total numbers of the signal sources of all of the groups are compared with one another, and (any of) the slice images included in a group with the largest total number is displayed in the center of the region 401A as illustrated in FIG. 32. Then, the slice images included in the other groups are arranged such that they are arranged in numerical order of the slice number (in a slice sequence) on the left and right of the central slice image.

Here, each of the slice images displayed in the region 401A is any of the slice images included in the groups. For example, it may be possible to display slice images having the middle slice numbers, slice images having the smallest slice numbers, or slice images having the largest slice numbers among the slice images with the consecutive slice numbers in the groups. Then, all of signal sources of the slice images included in the same groups as the slice images that are identified as images to be displayed are superimposed on the identified slice images. Further, when the slice numbers for the slice images to be displayed are determined, it is sufficient to assign slice numbers that are shifted by the same number of slice images included in the groups to slice images to be displayed on the left and right of the central slice images. For example, when a single group is constituted of ten slice images, the slice number of a slice image that is displayed on the left or right of the central slice image is calculated by adding or reducing ten to the slice number of the slice image that is displayed in the center.

Furthermore, as illustrated in FIG. 32, the information 440A indicating the slice number displays a range of the slice numbers of the slice images included in a group. Moreover, the information 440B indicating the number of signal sources displays a total value of the number of signal sources corresponding to all of the slice images included in the same group as the displayed slice image. Meanwhile, FIG. 32 illustrates an example in which a slice image is displayed in the center of the region 401A and only a single slice image is displayed on each of the left side and the right side of the central slice image, but it may be possible to display a plurality of slice images in the left-right direction. With this configuration, it is possible to reduce the total number of slice images displayed in the region 401A, so that it is possible to improve browsability as compared to the example described above.

Furthermore, while the number of signal sources superimposed on a slice image is used as a condition for a slice image to be initially displayed in the region 401A in the example described above, embodiments are not limited to this example. For example, it may be possible to apply a condition, such as a vector direction or strength of a signal source, which fits the purpose of analysis. As one example, it may be possible to use a value indicating validity or reliability of an estimated signal source or a value indicating approximate validity or approximate reliability of a signal source, and display a slice image on which a signal source with the highest value is superimposed in the center of the region 401A. The value indicating validity or reliability (hereinafter, simply referred to as reliability) may be calculated by using, for example, good of fitness (GOF). Then, slice images, on which signal sources for which the calculated values indicating the reliability exceed a predetermined threshold are superimposed, are displayed in the region 401A. Then, a slice image, on which a signal source with the largest value of reliability (with the highest reliability) is superimposed, is displayed in the region 401A, and other slice images are arranged and displayed such that they are arranged in numerical order of the slice number (in a slice sequence) on the left and right of the central slice image.

Here, FIG. 33 illustrates an example in which the display mode illustrated in FIG. 32 is applied. FIG. 33 is different from FIG. 32 in that the number indicated by the information 440B is not the number of signal sources but the value indicating the reliability. Further, the value indicating the reliability illustrated in FIG. 33 may be an average of the reliability of signal sources that are superimposed on slice images included in a single group, or may be a value of a signal source having a value indicating the highest reliability among signal sources superimposed on slice images included in a single group. With this configuration, by identifying a signal source with high reliability, it is possible to improve accuracy for identifying a target portion that may be a cause of symptoms. Furthermore, it may be possible to apply the number of signal sources as the number indicated by the information 440B as illustrated in FIG. 32, and express the signal sources (colors, shapes, sizes, or the like) in accordance with the value of GOF in a distinguished manner.

Meanwhile, while the slice images that are initially displayed in the region 401A in the examples illustrated in FIG. 26 to FIG. 33 are controlled without referring to the layout table 1001 illustrated in FIG. 19, embodiments are not limited to this example. In other words, as will be described below, it may be possible to refer to a layout table 1001*a* illustrated in FIG. 34 and control a layout of slice images that are initially displayed in the region 401A. The layout table 1001a illustrated in FIG. 34 is another mode of the layout table 1001 illustrated in FIG. 19, and is obtained by adding, to the layout table 1001, an item of a layout content of the merge screen 400 that is to be displayed when the merge button 185 in the analysis screen is pressed.

Figure 35:
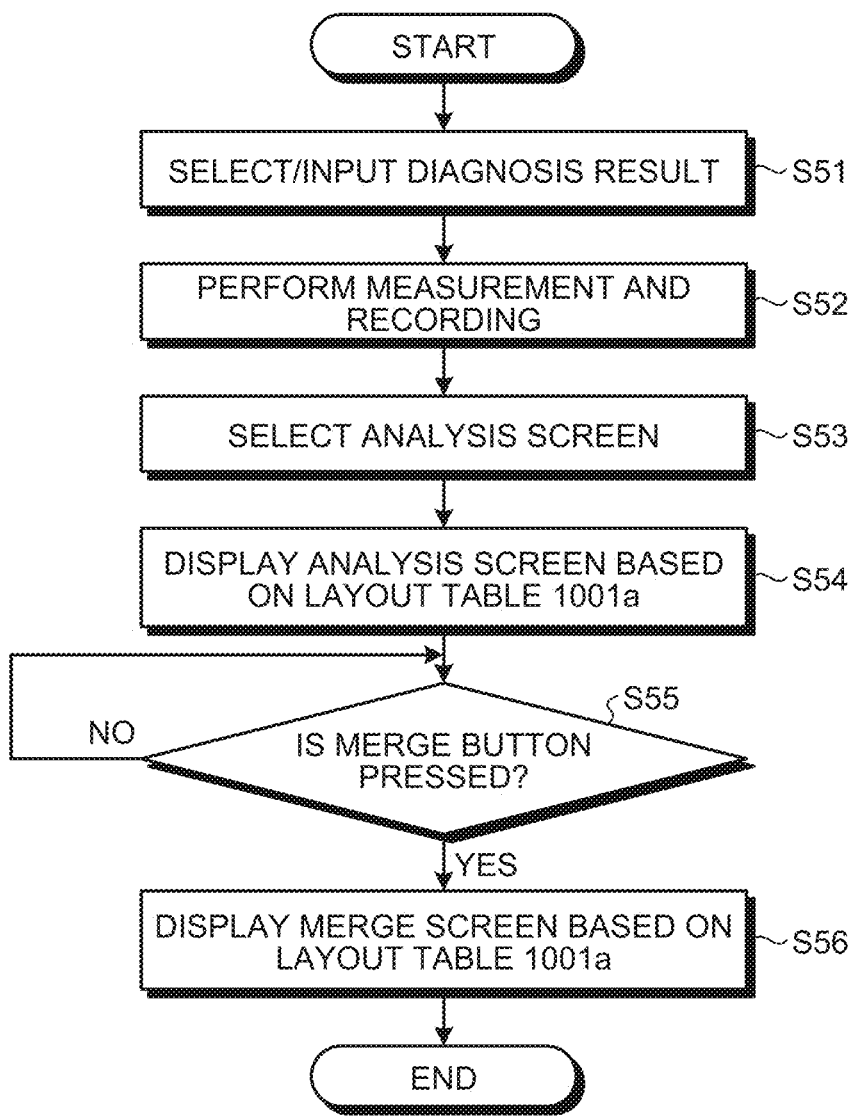
FIG. 35 is a flowchart illustrating operation of changing layouts of the analysis screen and the merge screen.

Operation of changing layouts of the analysis screen and the merge screen using the layout table 1001a as described above will be described with reference to FIG. 35. FIG. 35 is a flowchart illustrating operation of changing layouts of the analysis screen and the merge screen.

First, the information processing apparatus 50 has the layout table 1001a for associating a type of the medical examination result on the patient with types of layouts of the analysis screen and the merge screen 400. For example, when a user (doctor or the like) of the analysis screen performs operation of inputting a medical examination result (diagnosis result) via the input unit 311 illustrated in FIG. 3, the setting unit 304 sets, in accordance with the input operation, the layout table 1001a (one example of the layout information) for associating the medical examination result (including the medical interview result) with a layout content to be displayed in the analysis screen and a layout content to be displayed in the merge screen 400 that is displayed when the merge button 185 in the analysis screen is pressed, and stores the layout table 1001a in the storage unit 310 (Step S51). For example, with use of the input unit 311, it may be possible to perform operation of selecting one of options such as a medical examination result in the layout table 1001a or inputting the medical examination result via a menu in the measurement recording screen, or it may be possible to perform the selection operation or the input operation via an input screen that is different from the measurement recording screen. Meanwhile, while the layout table 1001a is described as information in a table format, embodiments are not limited to this example, and the layout table may be in any format as long as values in a plurality of fields of the layout table can be managed in an associated manner.

Further, when the doctor performs a medical examination on the patient before performing measurement and recording using the measurement recording screen illustrated in FIG. 6, the doctor reflects information on the medical examination result (including the medical interview result) in the patient information that is about the patient and that is stored in the storage unit 353 of the server 40. The patient information may be reflected (updated) by performing input operation on the information processing apparatus 50 or by directly inputting the patient information to the server 40.

Then, after performing measurement and recording on the specific patient (Step S52), the user (doctor or the like) of the analysis screen selects and opens an analysis screen in the information processing apparatus 50 to analyze measurement data (a magnetoencephalography signal, an electroencephalography signal, and the like) on the specific patient (Step S53), and the layout information acquiring unit 308 acquires the patient information (including the medical examination result) associated with the measurement data of the patient from the server 40 via the communication unit 306. The layout determining unit 309 refers to the layout table 1001a stored in the storage unit 310, acquires layout contents that correspond to the medical examination result on the patient information acquired by the layout information acquiring unit 308, and determines the layout contents as layouts of the analysis screen and the merge screen 400. The analysis display control unit 302 constructs an initial layout by changing the layout of the analysis screen that has a basic layout as illustrated in FIG. 12 etc., in accordance with the layout content of the analysis screen determined by the layout determining unit 309, and displays the initial layout (Step S54). Meanwhile, it is of course possible for the user to manually change, through input operation, a layout of the initially-displayed analysis screen for which the layout has been changed.

Thereafter, signal sources are appropriately estimated, and if operation of pressing the merge button 185 illustrated in FIG. 17 is received (YES at Step S55), the analysis display control unit 302 constructs an initial layout by changing the layout of the merge screen 400 that has a basic layout, in accordance with the layout content of the merge screen 400 determined by the layout determining unit 309, and displays the initial layout (Step S56).

In this manner, when an affected area is identified or estimated at the time of a medical examination, the layout of the merge screen 400 that is displayed when the merge button 185 is pressed can be changed using the layout table 1001a such that the affected area is focused on, in addition to changing the layout of the analysis screen.

Next, examples of the layout of the merge screen 400 displayed at Step S56 in FIG. 35 will be described with reference to FIG. 36 to FIG. 39. The examples illustrated in FIG. 36 to FIG. 39 are based on the assumption that information indicating that an affected area is present in the left brain is input or selected in the layout table 1001a.

Figure 36:
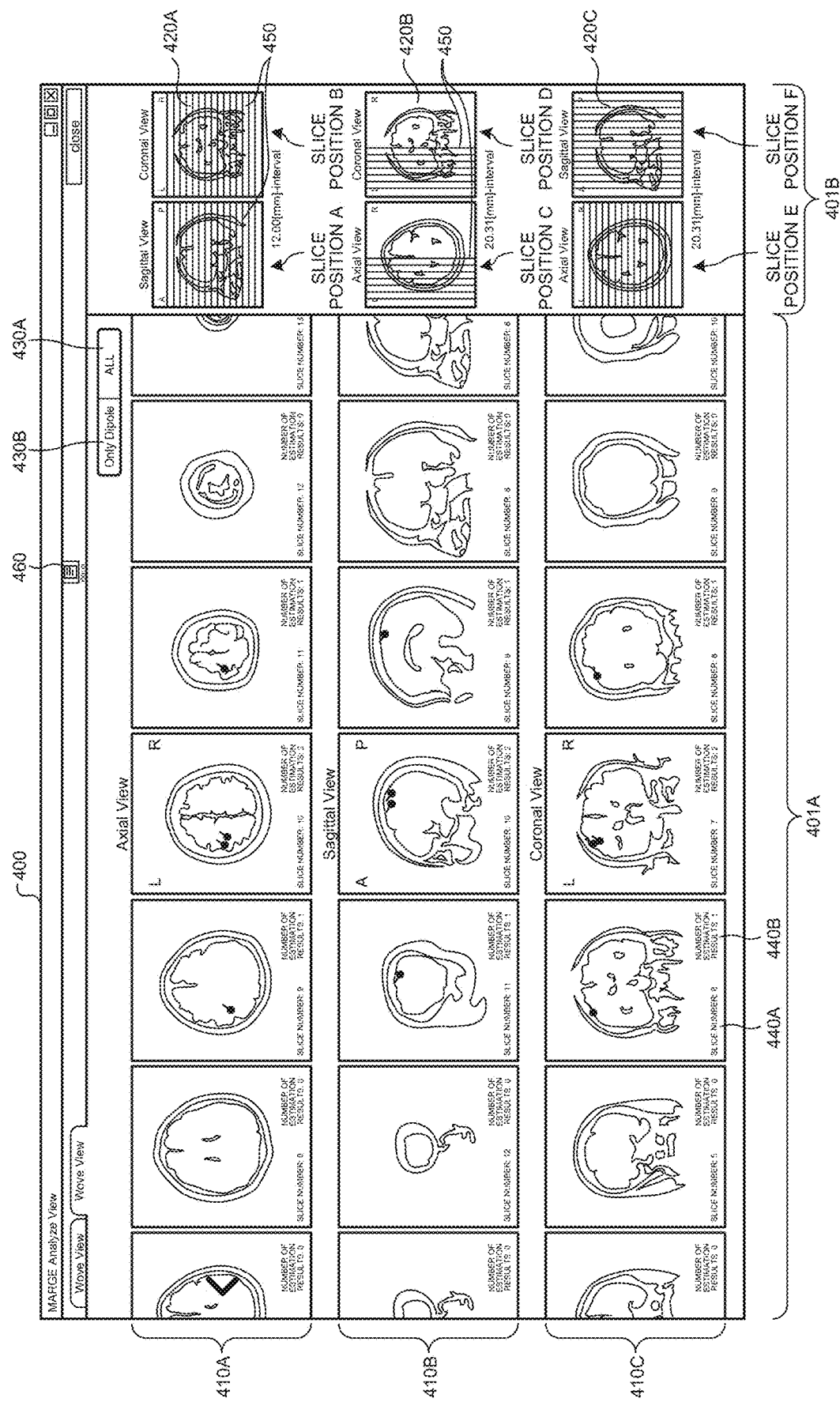
FIG. 36 is a diagram illustrating still another example of the screen that is displayed when the merge button is pressed.

FIG. 36 illustrates an example of the merge screen 400 whose layout is changed from the basic layout of the merge screen 400 illustrated in FIG. 26. As the slice positions C and D in the display region 420B, only the tomographic position lines 450 corresponding to the left brain that is input or selected in the layout table 1001a are displayed. Further, the display region 410B displays only slice images corresponding to the display region 420B. In contrast, the slice positions A, B, E, and F are the same as those of FIG. 26. In this manner, by hiding slice images of the right brain that is not specified in the layout table 1001a, it is possible to display only necessary slice images, so that it is possible to display necessary information in an easily viewable manner and it is possible to simplify analysis operation.

Figure 37:
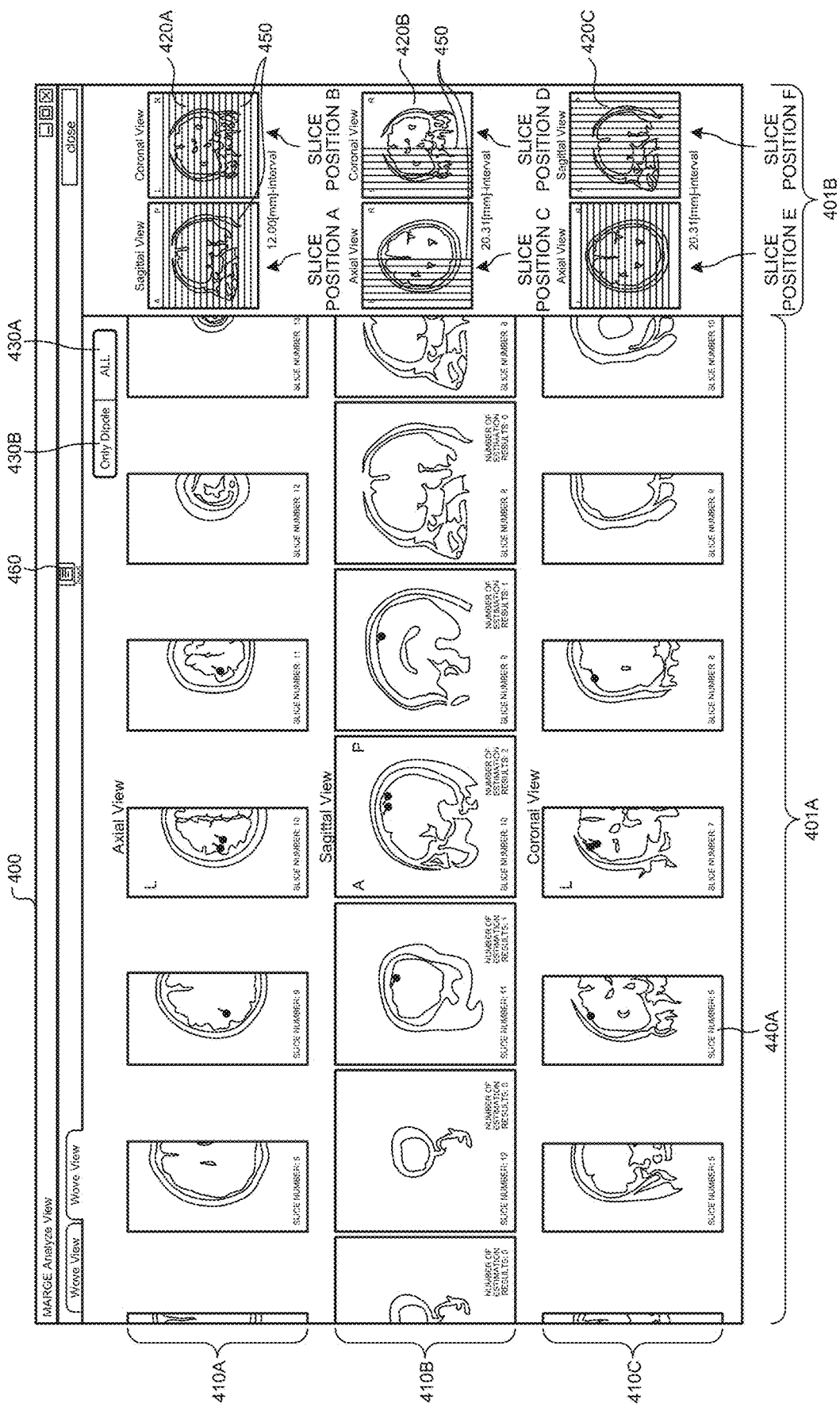
FIG. 37 is a diagram illustrating still another example of the screen that is displayed when the merge button is pressed.

In the example of the merge screen 400 illustrated in FIG. 37, right halves of the slice images in the display regions 410A and 410C corresponding to the slices A, B, E, and F are further hidden as compared to the merge screen 400 illustrated in FIG. 36. With this configuration, only images of the left brain are displayed in all of the directions of the display regions 410A to 410C and images of the right brain are hidden, so that visibility of the correspondence relationship among the display regions 410A to 410C can be improved.

Figure 38:
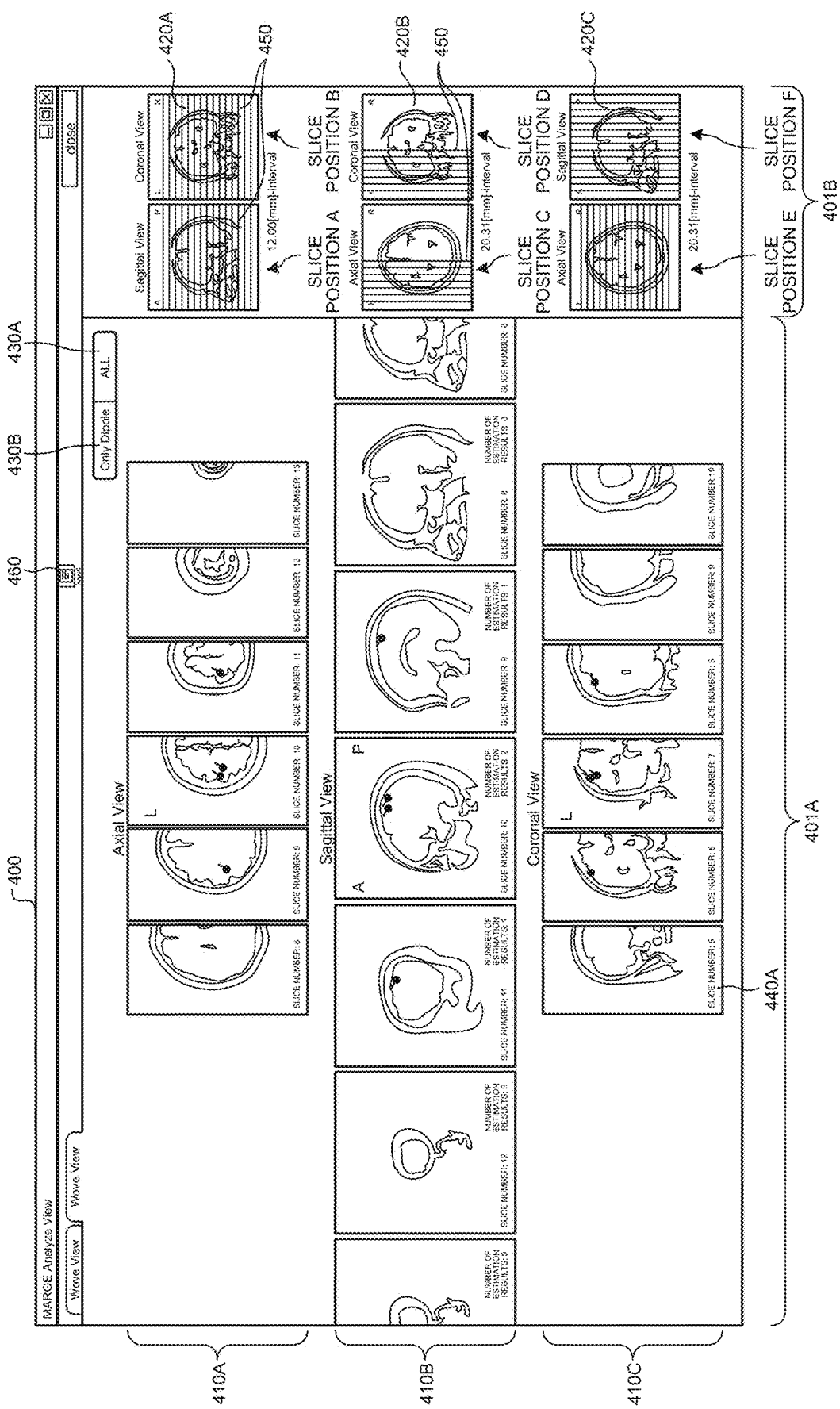
FIG. 38 is a diagram illustrating still another example of the screen that is displayed when the merge button is pressed.

In the example of the merge screen 400 illustrated in FIG. 38, intervals between the adjacent slice images in the display regions 410A and 401C are reduced as compared to the merge screen 400 illustrated in FIG. 37. With this configuration, it is possible to display an increased number of slice images in the left-right direction in the display regions 410A and 410C as compared to the display region 410B, so that listing property can be improved. Meanwhile, while only the slice images on which signal sources are superimposed are displayed in the display regions 410A and 410C, it may be possible to additionally display slice images on which signal sources are not superimposed.

While slice images corresponding to the respective tomographic position lines 450 in the display regions 420A to 420C are displayed in the display regions 410A to 410C in the examples of the merge screen 400 illustrated in FIG. 36 to FIG. 38 as described above, embodiments are not limited to this example. For example, it may be possible to display, in the display region 410B, only slices corresponding to the display region 420B, and hide the display regions 420A, 420C, the display regions 410A, 410C, and the slice positions A, B, E, and F. By limiting a display target to the left half, it is possible to display an increased number of slices in the same region. With this configuration, it is possible to display slice images with small slice widths, so that it is possible to perform analysis at high resolution.

Figure 39:
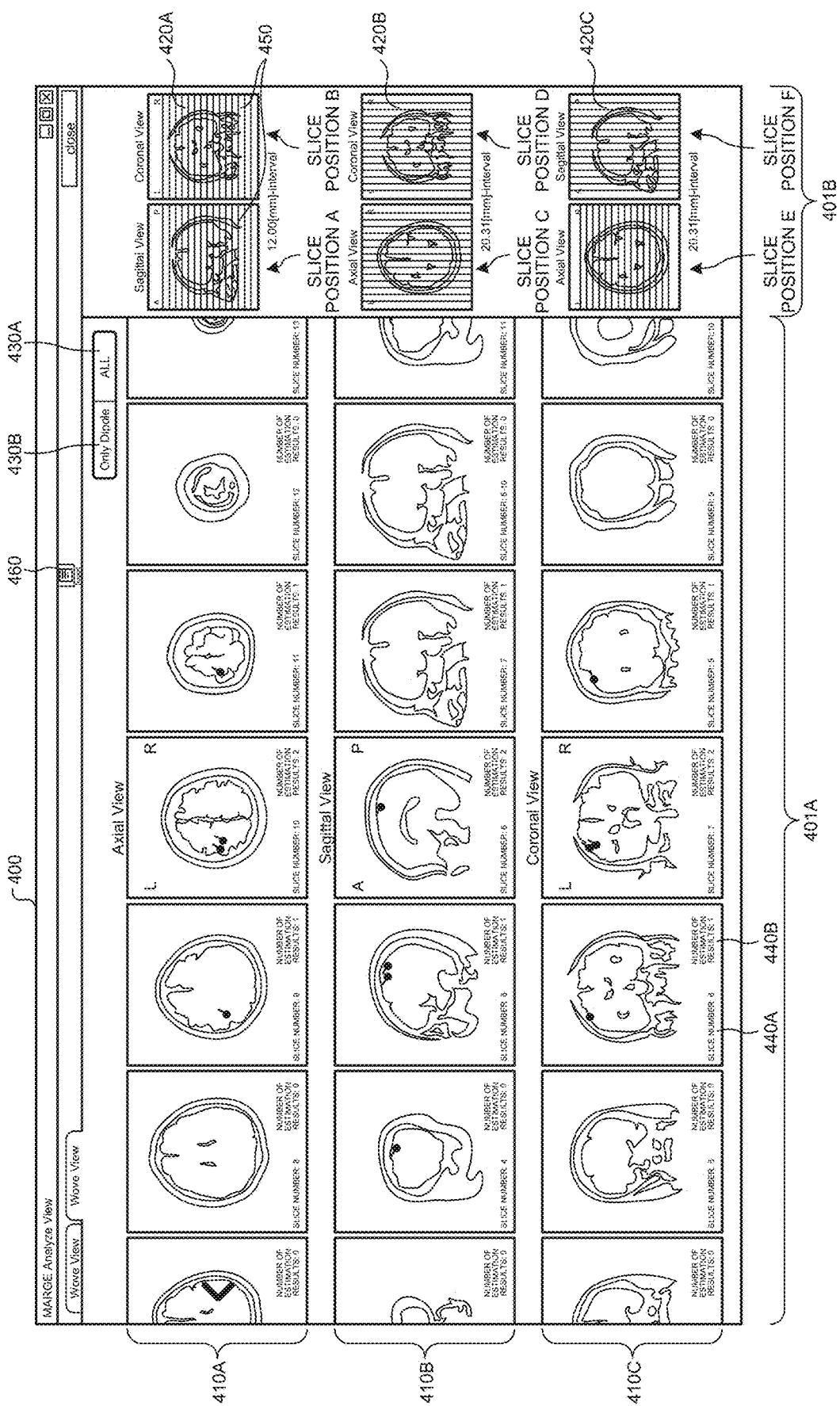
FIG. 39 is a diagram illustrating still another example of the screen that is displayed when the merge button is pressed.

FIG. 39 illustrates another example of the merge screen 400 whose layout is changed from the basic layout of the merge screen 400 illustrated in FIG. 26. Slice images at positions corresponding to the left brain among the slice positions C and D are displayed one by one in the display region 410B. In contrast, slice images at positions corresponding to the right brain among the slice positions C and D are divided into groups of a plurality of (for example, three) slice images in numerical order of the slice number, a total number of signal sources corresponding to the slice images included in each of the groups is calculated, and the signal sources are displayed on representative slice images in a superimposed manner. Further, slice images are displayed at the slice positions A, B, E, and F in the same manner as FIG. 26. In this manner, by displaying slice images of the left brain specified in the layout table 1001a for each of slices and thinning out slice images of the right brain that is not specified, it is possible to display necessary information in an easily viewable manner and simplify analysis operation.

As described above, the information processing apparatus 50 according to the first embodiment acquires information (patient information) on a result of a medical examination (including a medical interview) that is performed on a patient in advance, changes a layout of the analysis screen in accordance with the result, and display the changed layout as an initial layout. With this configuration, it is possible to appropriately change a layout of information to be displayed, in accordance with the medical examination result (one example of a predetermined condition). Therefore, it is possible to save time and effort of manually changing the layout, hide information that is not needed based on observation on the patient, and display necessary information in an easily viewable manner, so that it is possible to simplify analysis operation.

Second Embodiment

A biological signal measurement system 1 according to a second embodiment will be described mainly in terms of a difference from the biological signal measurement system 1 according to the first embodiment. In the first embodiment, operation of changing a layout of the analysis screen in accordance with a result of a medical examination (including a medical interview) that is performed on a patient in advance and displaying the changed layout as an initial layout has been described. In the second embodiment, operation of changing a layout of the analysis screen in accordance with a signal source estimation state will be described. Meanwhile, an entire configuration of the biological signal measurement system 1 and hardware configurations and functional block configurations of an information processing apparatus 50 and a server 40 according to the second embodiment are the same as those described in the first embodiment.

Operation of Functional Blocks of Information Processing Apparatus

The functional block configuration and operation of the information processing apparatus 50 according to the second embodiment will be described with reference to FIG. 3 described earlier.

The setting unit 304 sets a layout table for associating the signal source estimation state with a layout content to be displayed in the analysis screen, in accordance with input operation received by the input unit 311, and stores the layout table in the storage unit 310.

The layout information acquiring unit 308 acquires information (one example of the determination information) indicating a specific condition for determining a layout of the analysis screen. Specifically, in the second embodiment, the layout information acquiring unit 308 acquires, as the information indicating the specific condition, information indicating how many signal sources are estimated by operation of pressing the estimation button 212 (see FIG. 16) (one example of information indicating the signal source estimation state and information related to an analysis result).

The layout determining unit 309 determines whether the information indicating the signal source estimation state acquired by the layout information acquiring unit 308 matches a "signal source estimation state" defined in the layout table, which is stored in the storage unit 310 and in which the signal source estimation state and the layout content of the analysis screen are associated. Then, the layout determining unit 309 acquires a layout content corresponding to the information indicating the signal source estimation state, which is acquired by the layout information acquiring unit 308 and which matches the "signal source estimation state" defined in the layout table, and determines the acquired layout content as a layout of the analysis screen.

Meanwhile, operation performed by the recording display control unit 301, the analysis display control unit 302, the merge display control unit 303, the analyzing unit 305, the communication unit 306, the sensor information acquiring unit 307, the storage unit 310, and the input unit 311 are the same as the operation described in the first embodiment.

Operation of Changing Layout of Display Contents of Analysis Screen

Figure 40:
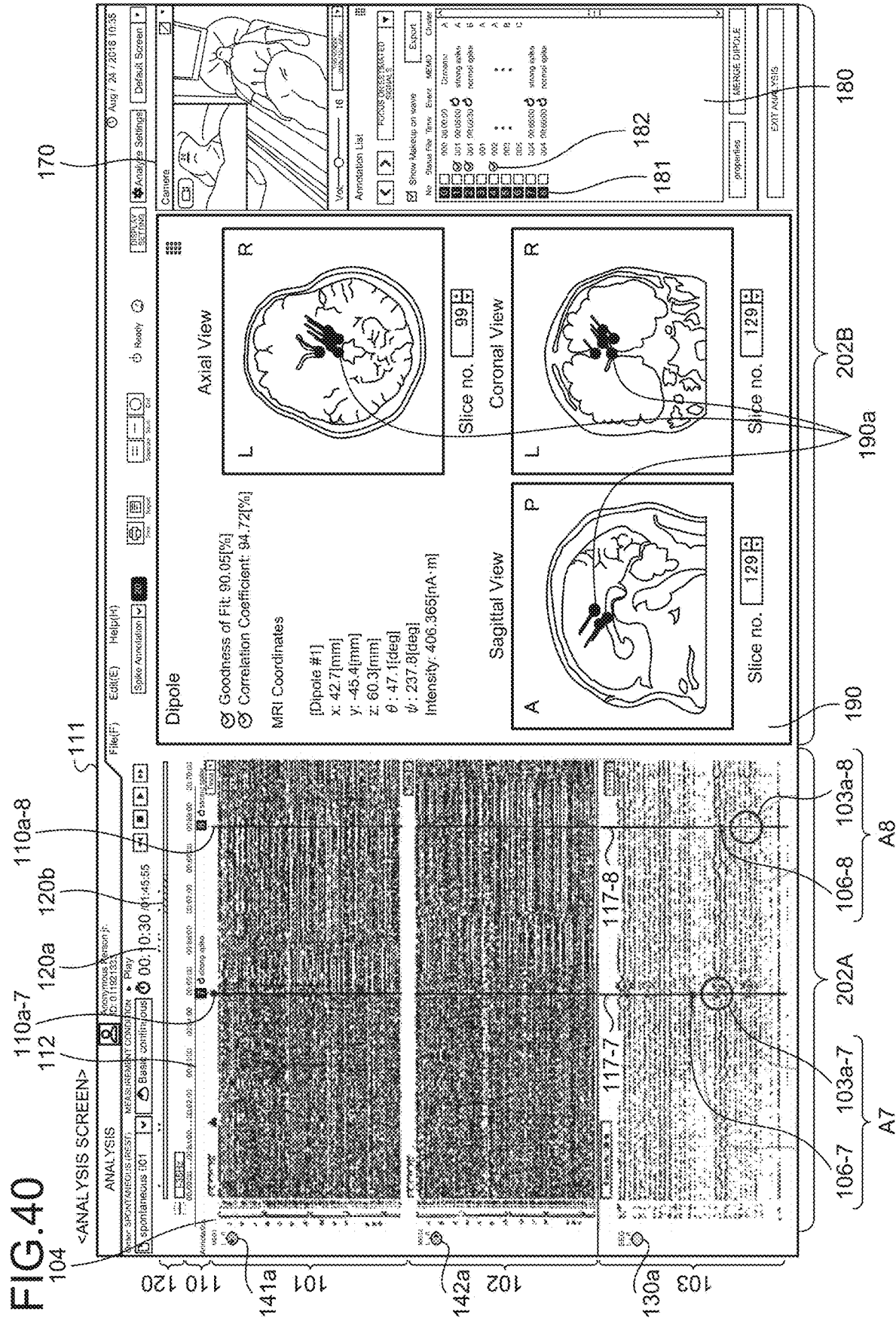
FIG. 40 is a diagram illustrating an example in which an MRI image is enlarged in an analysis screen according to a second embodiment.
Figure 41:
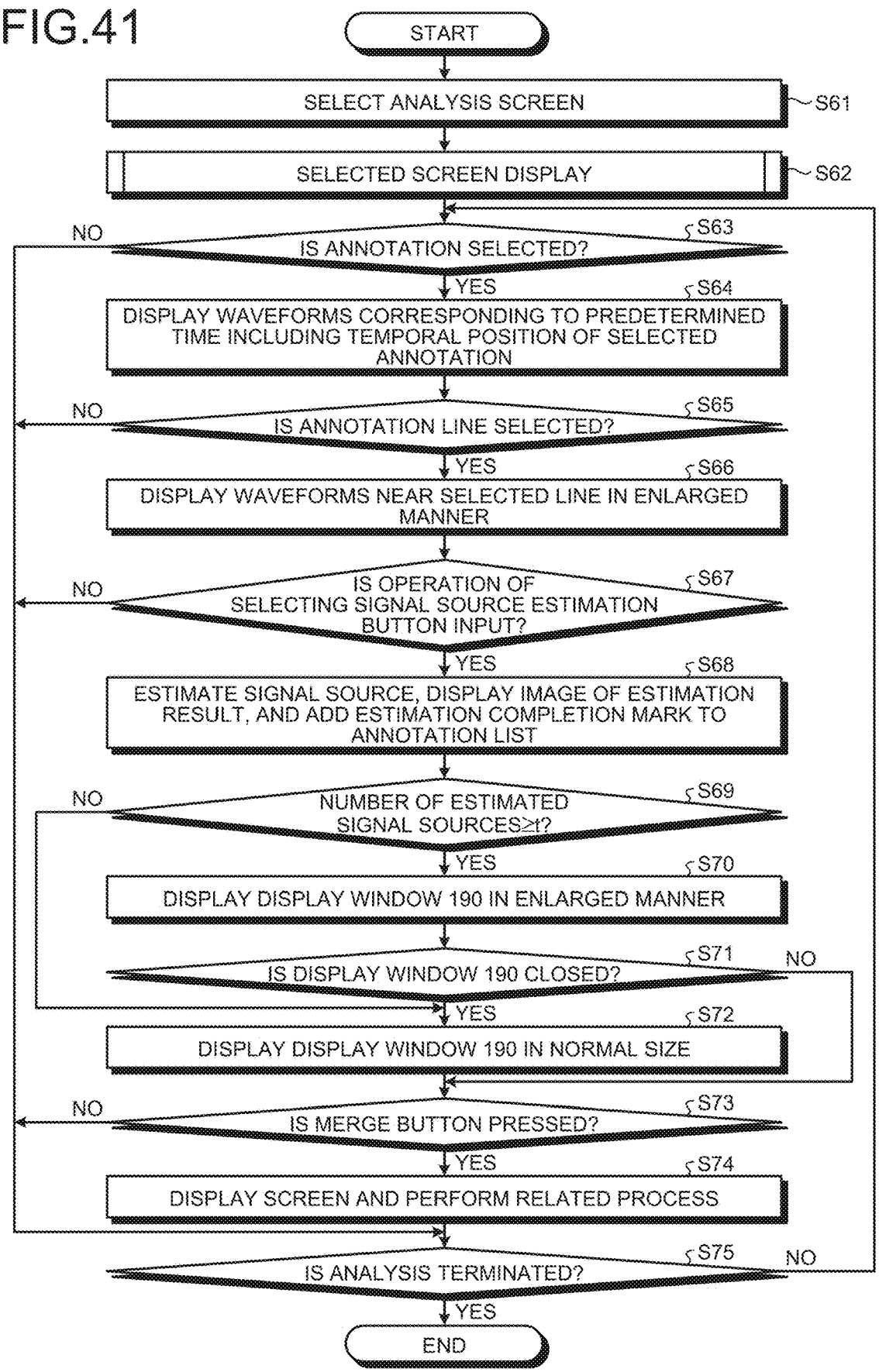
FIG. 41 is a flowchart illustrating operation that is performed by an information processing apparatus of the second embodiment at the time of analysis.

FIG. 40 is a diagram illustrating an example in which an MRI image is enlarged in the analysis screen according to the second embodiment. FIG. 41 is a flowchart illustrating operation performed by the information processing apparatus of the second embodiment at the time of analysis. FIG. 42 is a diagram illustrating an example of the layout table of the second embodiment. Operation performed by the information processing apparatus 50 according to the second embodiment for changing a layout of display contents of the analysis screen will be described below with reference to FIG. 40 to FIG. 42.

As described above, when information measured by magnetoencephalograph or electroencephalograph or related information is to be displayed, in some cases, an appropriate mode of displaying the information in the analysis screen may be substantially determined depending on, for example, the signal source estimation state (dipole estimation). For example, if the number of estimated signal sources is equal to or larger than a predetermined number, the analysis display control unit 302 displays the estimated signal sources (the dipole estimation results 190a) on the display window 190 in a superimposed manner as illustrated in FIG. 40 in the current layout of the analysis screen, and displays the display window 190 in an enlarged manner. At this time, it is desirable for the analysis display control unit 302 to display all of the estimated signal sources in the display window 190. This makes it possible to check positions of the estimated signal sources in the display window 190 that is displayed in an enlarged manner, so that it is possible to improve checking accuracy of positions of affected areas. Further, when a predetermined number of estimated signal sources are obtained, the analysis display control unit 302 may determine that it is not necessary to estimate a new signal source and hide the enlarged display region 200 as a result of displaying the display window 190 in an enlarged manner as illustrated in FIG. 40.

Details of the above-described operation of changing the layout of display contents of the analysis screen (for example, operation of displaying the display window 190 in an enlarged manner as described above) depending on the signal source estimation state (dipole estimation) will be described below. First, a user of the analysis screen sets a layout table for associating a type of the signal source estimation state (dipole estimation) with a type of the layout of the analysis screen. For example, as illustrated in FIG. 42, when a user (doctor or the like) of the analysis screen performs input operation on the input unit 311, the setting unit 304 sets, in accordance with the input operation, a layout table 1002 (one example of the layout information) for associating the signal source estimation state with a layout content to be displayed in the analysis screen, and stores the layout table 1002 in the storage unit 310. In the example of the layout table 1002 illustrated in FIG. 42, for example, a layout content of "enlarge an MRI tomography image" (enlarge the display window 190) is associated with a signal source estimation state of "ten or more signal sources are estimated". Meanwhile, while the layout table 1002 is described as information in a table format, embodiments are not limited to this example, and the layout table may be in any format as long as values in a plurality of fields of the layout table can be managed in an associated manner.

The layout information acquiring unit 308 acquires, as the information indicating the specific condition, information (information indicating the signal source estimation state) indicating how many signal sources are estimated by operation of pressing the estimation button 212 (see FIG. 16). The layout determining unit 309 determines whether the information indicating the signal source estimation state acquired by the layout information acquiring unit 308 matches a "signal source estimation state" that is defined in the layout table 1002 stored in the storage unit 310. Then, the layout determining unit 309 acquires, from the layout table 1002, a layout content corresponding to the information indicating the signal source estimation state, which is acquired by the layout information acquiring unit 308 and which matches the "signal source estimation state" defined in the layout table 1002, and determines the acquired layout content as a layout of the analysis screen. The analysis display control unit 302 changes the layout from the current analysis screen in accordance with the layout content of the analysis screen determined by the layout determining unit 309.

The flow of the operation as described above will be explained with reference to FIG. 41. The layout table 1002 illustrated in FIG. 42 is set through the above-described operation in the same manner as the operation of setting the layout table 1001. When "analysis" is selected in the start screen 204 (see FIG. 5) (Step S61), analysis is started and the analysis screen is displayed (Step S62). In this case, a layout of the analysis screen is changed through the same operation as described above with reference to FIG. 20 or FIG. 25.

When the analysis screen is displayed, it is determined whether a specific annotation is selected (Step S63). The annotation may be selected by selecting a specific annotation number or a specific row in the annotation list 180 or by specifying a temporal position by operating the time zone 120b on the time axis 122 in the display region 120. If an annotation is selected (YES at Step S63), signal waveforms corresponding to a predetermined time including the temporal position of the selected annotation are displayed (Step S64).

In the displayed situation, it is determined whether the line 117 indicating a temporal position of a mark displayed in a highlighted manner is selected (Step S65). If the line 117 is selected (YES at Step S65), signal waveforms in a certain time range including the selected line are displayed in an enlarged manner (Step S66). A channel of the waveform displayed in the enlarged display region 200 corresponds to the sensor that is determined at Step S224. Here, it is not always necessary to display enlarged views of signal waveforms that are present near the mark displayed in a highlighted manner in the enlarged display region 200, but it may be possible to display enlarged views of signal waveforms of a different kind that are present at the same temporal position. For example, when a mark displayed in a highlighted manner is added to electroencephalography signal waveforms, it may be possible to display enlarged views of magnetoencephalography signal waveforms that are present at the same temporal position. Further, it may be possible to display enlarged views of signal waveforms that are acquired by channels in a certain range including a channel that has acquired the marked signal waveform, instead of displaying enlarged views of signal waveforms of all of the channels. In this case, it may be possible to determine a type of signal waveforms to be displayed in an enlarged manner or determine whether designation of a channel range is input or not.

Subsequently, it is determined whether the signal source estimation button 212 is pressed (Step S67). If the signal source estimation button 212 is pressed (YES at Step S67), calculation for estimating a signal source is performed. An estimation result is displayed on an MRI tomography screen and the estimation completion mark 182 is added to the annotation list 180 (Step S68).

Subsequently, the layout information acquiring unit 308 acquires, as the information indicating the specific condition, information (information indicating the signal source estimation state) indicating how many signal sources are estimated by operation of pressing the estimation button 212 (see FIG. 16). The layout determining unit 309 determines whether the information indicating the signal source estimation state acquired by the layout information acquiring unit 308 matches the "signal source estimation state" that is defined in the layout table 1002 stored in the storage unit 310 (Step S69). If the number of signal sources included in the information indicating the signal source estimation state acquired by the layout information acquiring unit 308 is equal to or larger than a predetermined number t (for example, ten illustrated in FIG. 42) (YES at Step S69), the analysis display control unit 302 displays the estimated signal sources on the display window 190 in a superimposed manner as illustrated in FIG. 40 in the current layout of the analysis screen, and displays the display window 190 in an enlarged manner (Step S70).

In contrast, if the number of signal sources included in the information indicating the signal source estimation state acquired by the layout information acquiring unit 308 is smaller than the predetermined number t (NO at Step S69)

or if the display window 190 displayed in an enlarged manner is closed (YES at Step S71), the analysis display control unit 302 displays the display window 190 in a normal size in the analysis screen as illustrated in FIG. 15 for example (Step S72).

Then, if operation of pressing the merge button 185 (see FIG. 17) that is arranged below the annotation list 180 is received (YES at Step S73), the merge display control unit 303 of the information processing apparatus 50 displays the merge screen 400 and performs a process related to the merge screen 400 (Step S74). If operation of pressing the merge button 185 is not received (NO at Step S73) or after Step S74, it is determined whether an analysis termination command is input (Step S75). If an annotation is not selected (NO at Step S63), if an annotation line for displaying an enlarged view is not selected (NO at Step S65), or if operation of pressing the signal source estimation button 212 is not received (NO at Step S67), the process proceeds to Step S75 and it is determined whether to terminate the analysis. Step S63 to S74 are repeated until the analysis termination command is input (YES at Step S75).

Meanwhile, for example, when the display window 190 is displayed in an enlarged manner, as operation of changing a layout of the analysis screen, it may be possible to return the layout to the original layout upon receiving operation of clicking waveforms displayed in the display regions 101 to 103 in the analysis screen illustrated in FIG. 40, that is, it may be possible to return the size of the display window 190 to a normal size and display the enlarged display region 200 again.

In this manner, the layout of the analysis screen is changed depending on the signal source estimation state. With this configuration, it is possible to appropriately change the layout of information to be displayed, in accordance with the signal source estimation state (one example of the specific condition). Therefore, it is possible to save time and effort of manually changing the layout and display necessary information in an easily viewable manner depending on the signal source estimation state, so that it is possible to simplify operation of checking a state of an affected area.

Figure 43:
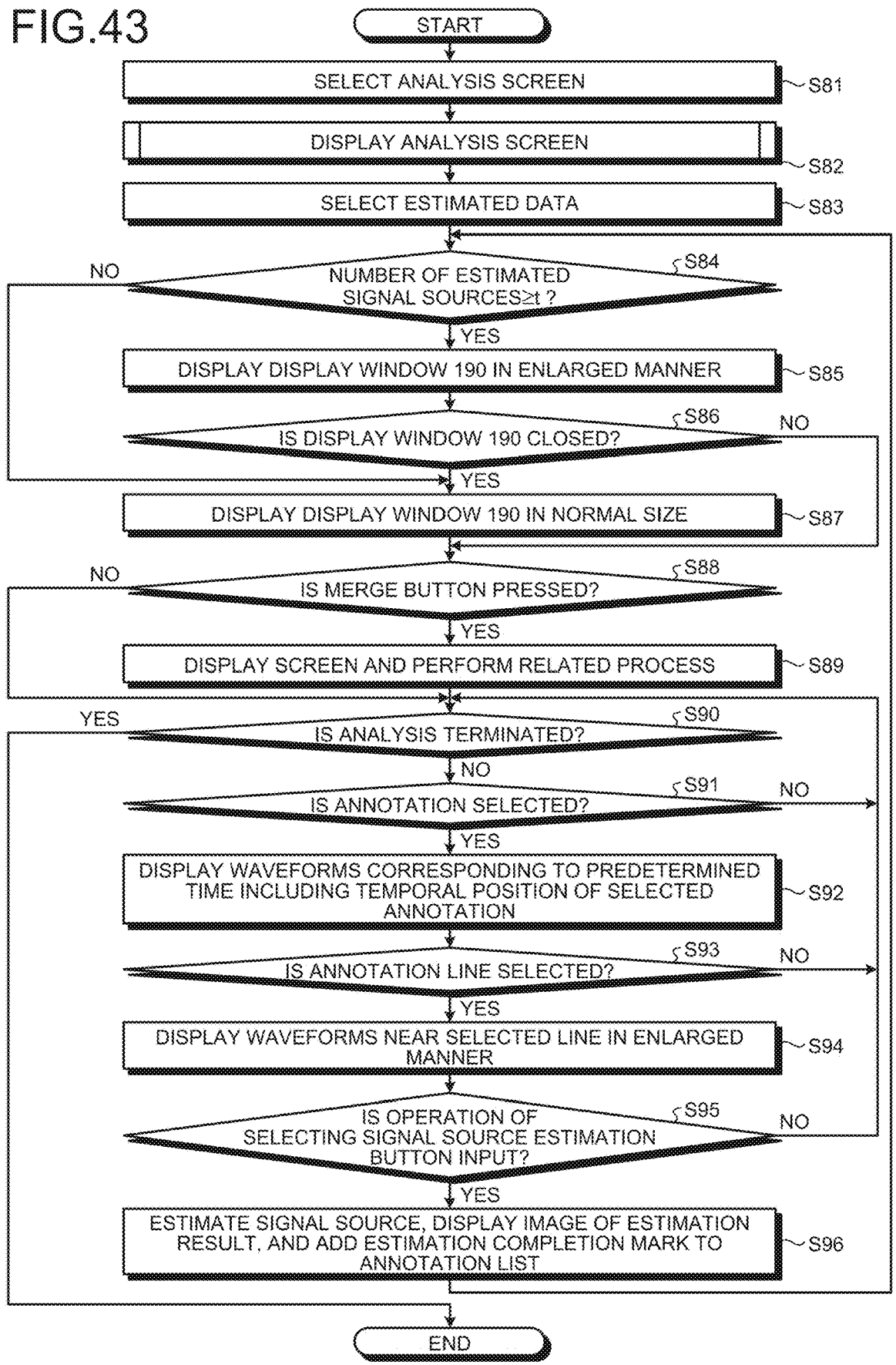
FIG. 43 is a flowchart illustrating another example of the operation that is performed by the information processing apparatus of the second embodiment at the time of analysis.

Meanwhile, as described above, when estimation of a signal source is reflected in an annotation by pressing the estimation button 212, information on the annotation is stored in the server 40 or the like, and, it may be possible to change the initial layout of the analysis screen when the analysis screen is opened, on the basis of the signal source estimation state (the number of signal sources or the like) that is included in annotation information associated with measurement data of a patient to be checked. Specifically, the layout information acquiring unit 308 acquires, from the server 40, the signal source estimation state (the number of signal sources or the like) that is included in annotation information associated with measurement data of a patient to be checked. Then, the layout determining unit 309 may acquire, from the layout table 1002, a layout content corresponding to the information indicating the signal source estimation state, which is acquired by the layout information acquiring unit 308 and which matches the "signal source estimation state" defined in the layout table 1002, and determine the acquired layout content as an initial layout of the analysis screen. This operation will be described below with reference to FIG. 43.

When "analysis" is selected in the start screen 204 (see FIG. 5) (Step S81), analysis is started and the analysis screen is displayed (Step S82). In this case, a layout of the analysis screen is changed through the same operation as the operation described above with reference to FIG. 20 or FIG. 25.

A user (doctor or the like) of the analysis screen selects, in the analysis screen, measurement data that is about a specific patient and that is stored in the server 40 (Step S83). With this operation, the layout information acquiring unit 308 acquires information (information indicating the signal source estimation state) indicating how many signal sources are estimated from the measurement data. The layout determining unit 309 determines whether the information indicating the signal source estimation state acquired by the layout information acquiring unit 308 matches a "signal source estimation state" that is defined in the layout table 1002 stored in the storage unit 310 (Step S84). If the number of signal sources included in the information indicating the signal source estimation state acquired by the layout information acquiring unit 308 is equal to or larger than the predetermined number t (for example, ten illustrated in FIG. 42) (YES at Step S84), the analysis display control unit 302 displays the estimated signal sources on the display window 190 in a superimposed manner as illustrated in FIG. 40 in the current layout of the analysis screen, and displays the display window 190 in an enlarged manner (Step S85).

In contrast, if the number of signal sources included in the information indicating the signal source estimation state acquired by the layout information acquiring unit 308 is smaller than the predetermined number t (NO at Step S84) or if the display window 190 displayed in an enlarged manner is closed (YES at Step S86), the analysis display control unit 302 displays the display window 190 in a normal size in the analysis screen as illustrated in FIG. 15 for example (Step S87).

Then, if operation of pressing the merge button 185 (see FIG. 17) that is arranged below the annotation list 180 is received (YES at Step S88), the merge display control unit 303 of the information processing apparatus 50 displays the merge screen 400 and performs a process related to the merge screen 400 (Step S89). If operation of pressing the merge button 185 is not received (NO at Step S88) or after Step S89, it is determined whether an analysis termination command is input (Step S90).

If the analysis termination command is not input (NO at Step S90), it is determined whether a specific annotation is selected (Step S91). The annotation may be selected by selecting a specific annotation number or a specific row in the annotation list 180 or by specifying a temporal position by operating the time zone 120b on the time axis 122 in the display region 120. If an annotation is selected (YES at Step S91), signal waveforms corresponding to a predetermined time including the temporal position of the selected annotation are displayed (Step S92).

In the displayed situation, it is determined whether the line 117 indicating a temporal position of a mark displayed in a highlighted manner is selected (Step S93). If the line 117 is selected (YES at Step S93), signal waveforms in a certain time range including the selected line are displayed in an enlarged manner (Step S94). A channel of the waveform displayed in the enlarged display region 200 corresponds to the sensor that is determined at Step S224. Here, it is not always necessary to display enlarged views of signal waveforms that are present near the mark displayed in a highlighted manner in the enlarged display region 200, but it may be possible to display enlarged views of signal waveforms of a different kind that are present at the same temporal position. For example, when a mark displayed in a highlighted manner is added to electroencephalography signal waveforms, it may be possible to display enlarged views of magnetoencephalography signal waveforms that are present at the same temporal position. Further, it may be possible to display enlarged views of signal waveforms that are acquired by channels in a certain range including a channel that has acquired the marked signal waveform, instead of displaying enlarged views of signal waveforms of all of the channels. In this case, it may be possible to determine a type of signal waveforms to be displayed in an enlarged manner or determine whether designation of a channel range is input or not.

Subsequently, it is determined whether the signal source estimation button 212 is pressed (Step S95). If the signal source estimation button 212 is pressed (YES at Step S95), calculation for estimating a signal source is performed. An estimation result is displayed on an MRI tomography screen and the estimation completion mark 182 is added to the annotation list 180 (Step S96). Further, information on the annotation in which the estimated signal source is reflected is additionally included in the measurement data on the patient, and stored (updated) in the server 40 or the like. Then, the process returns to Step S84.

Figure 44:
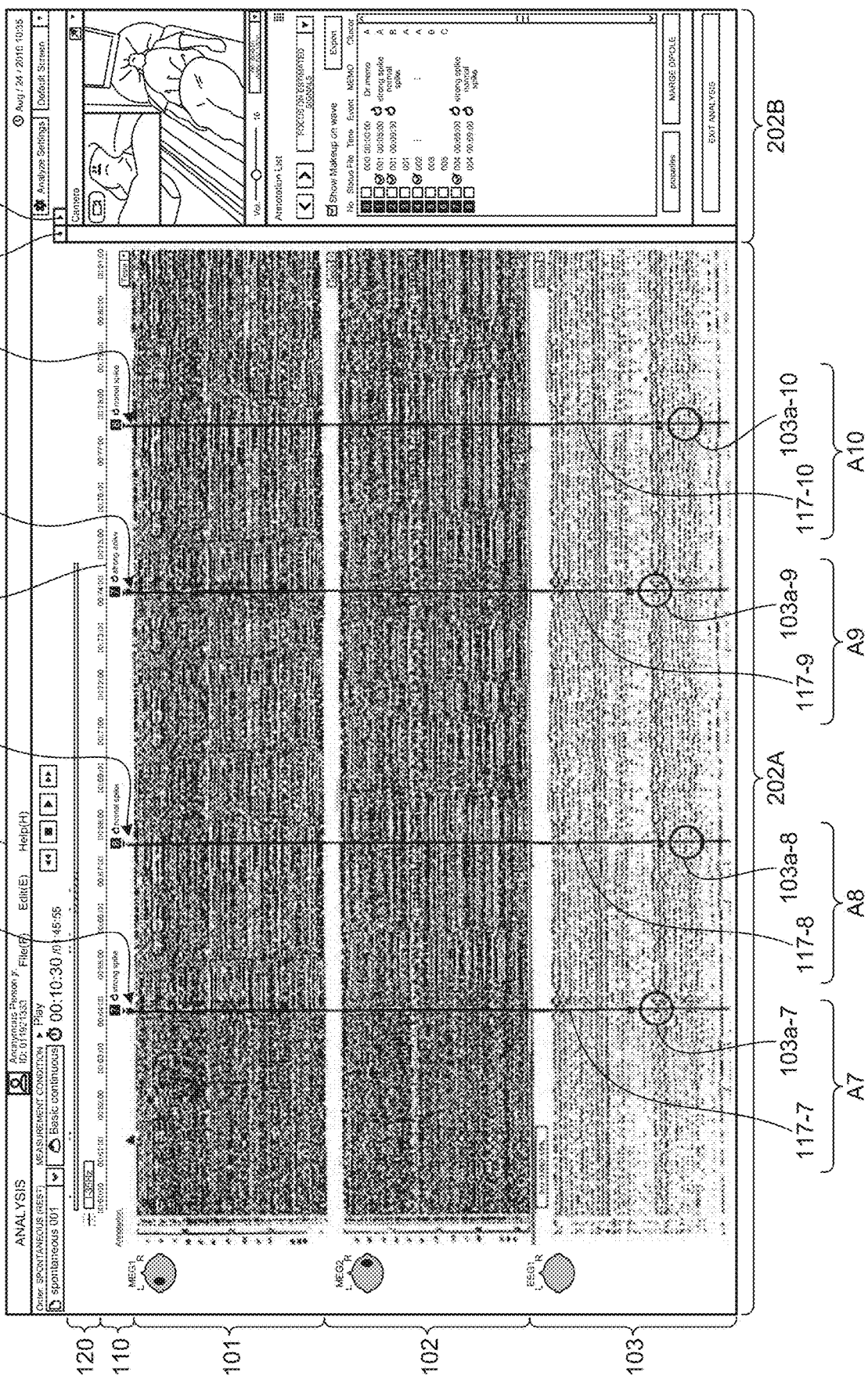
FIG. 44 is a diagram illustrating an example in which a display window is hidden in the analysis screen.
Figure 45:
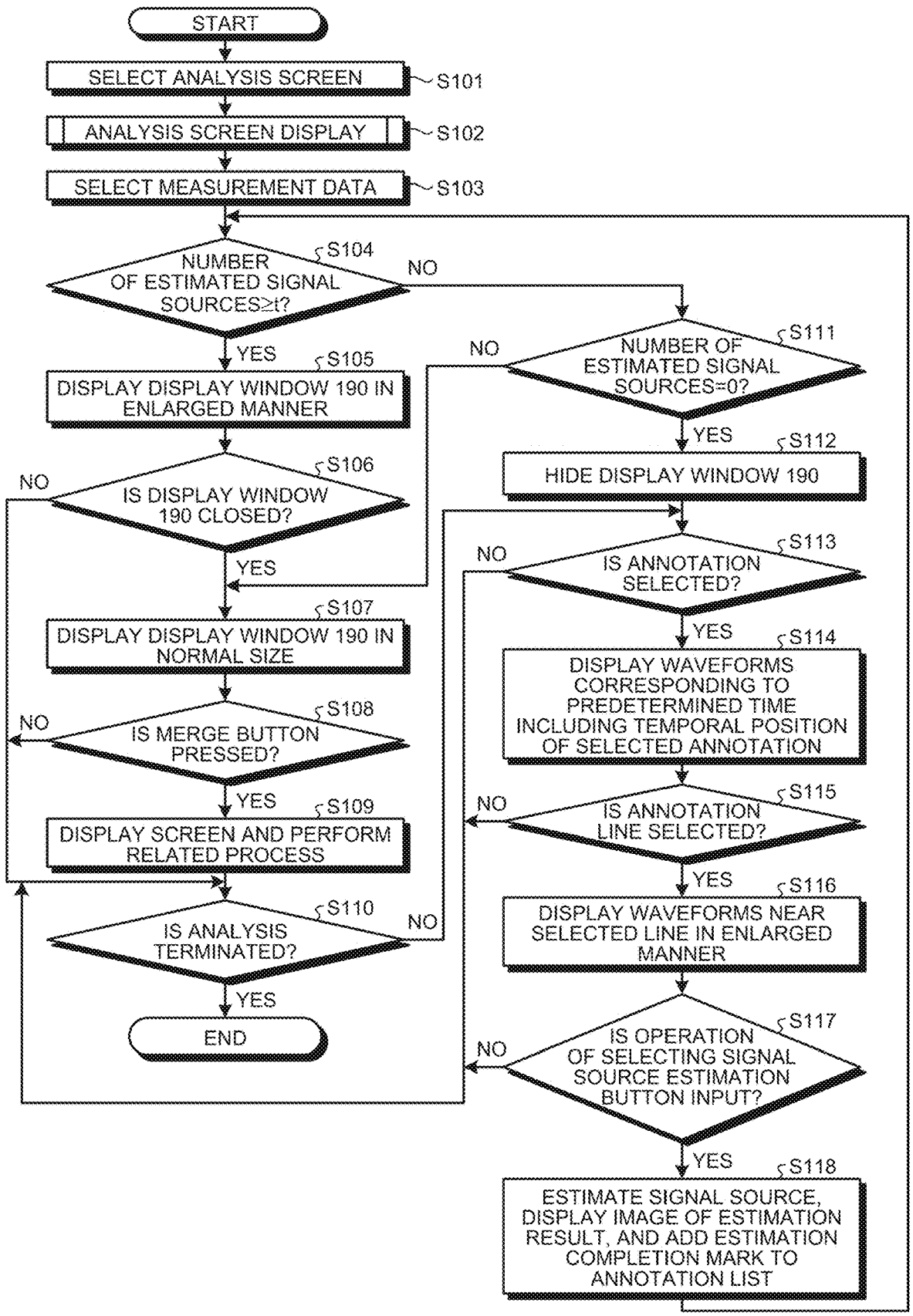
FIG. 45 is a flowchart illustrating operation of changing a layout of the analysis screen.

The details of the layout change described above are mere example, and embodiments are not limited to this example. For example, if no signal source is estimated as the signal source estimation state, it may be possible to hide the display window 190 and display at least any of the display regions 101 to 103 in an enlarged manner in the time axis direction by the amount corresponding to the display area of the display window 190 as illustrated in FIG. 44 for example. Alternatively, it may be possible to hide the display window 190 when the number of signal sources is below the predetermined number t. The analysis screen illustrated in FIG. 44 is different from the analysis screens illustrated in FIG. 12 and FIG. 14 in that the display window 190, the isofield contour map 150, and the map area 160 are hidden. Further, waveforms in the display regions 101 to 103 are displayed even in the regions where the display window 190, the isofield contour map 150, and the map area 160 have been displayed. In this manner, by displaying the display regions 101 to 103 in an enlarged manner in the left-right direction, an annotation A9 including a line 117-9 and a mark 103a-9 and an annotation A10 including a line 117-10 and a mark 103a-10 are displayed in addition to the annotations A7 and A8. Furthermore, annotations 110a-9 and 110a-10 are displayed along the time axis 112 in addition to the annotations 110a-7 and 110a-8. Moreover, the display window 190, the isofield contour map 150, and the map area 160 are displayed again when a window open button 145 is pressed in FIG. 44, and the display window 190, the isofield contour map 150, and the map area 160 are hidden again when a window close button 146 is pressed. The waveforms in the display regions 101 to 103 in FIG. 44 can be displayed in an enlarged manner in the time axis direction as compared to those illustrated in FIG. 12, so that it is possible to view longer waveforms at once. The above-described operation of hiding the display window 190 will be described below with reference to FIG. 45.

When "analysis" is selected in the start screen 204 (see FIG. 5) (Step S101), analysis is started and the analysis screen is displayed (Step S102). In this case, a layout of the analysis screen is changed through the same operation as described above with reference to FIG. 20 or FIG. 25. A user (doctor or the like) of the analysis screen selects, in the analysis screen, measurement data that is about a specific patient and that is stored in the server 40 (Step S103). With this operation, the layout information acquiring unit 308 acquires information (information indicating the signal source estimation state) indicating how many signal sources are estimated from the measurement data. The layout determining unit 309 determines whether the information indicating the signal source estimation state acquired by the layout information acquiring unit 308 matches a "signal source estimation state" that is defined by the layout table 1002 stored in the storage unit 310 (Step S104). If the number of signal sources included in the information indicating the signal source estimation state acquired by the layout information acquiring unit 308 is equal to or larger than the predetermined number t (for example, ten illustrated in FIG. 42) (YES at Step S104), the analysis display control unit 302 displays the estimated signal sources on the display window 190 in a superimposed manner as illustrated in FIG. 40 in the current layout of the analysis screen, and displays the display window 190 in an enlarged manner (Step S105).

In contrast, if the number of signal sources included in the information indicating the signal source estimation state acquired by the layout information acquiring unit 308 is smaller than the predetermined number t (NO at Step S104), the layout determining unit 309 further determines whether the number of signal sources included in the information indicating the signal source estimation state acquired by the layout information acquiring unit 308 is zero (Step S111). If the number of signal sources is zero (YES at Step S111), the analysis display control unit 302 hides the display window 190 in the current layout of the analysis screen as illustrated in FIG. 44 (Step S112).

In contrast, if the display window 190 displayed in an enlarged manner is closed at Step S106 (YES at Step S106) or if the number of signal sources is not zero at Step S111 (NO at Step S111), the analysis display control unit 302 displays the display window 190 in a normal size in the analysis screen as illustrated in FIG. 15 for example (Step S107).

Then, if operation of pressing the merge button 185 (see FIG. 17) that is arranged below the annotation list 180 is received (YES at Step S108), the merge display control unit 303 of the information processing apparatus 50 displays the merge screen 400 and performs a process related to the merge screen (Step S109). If operation of pressing the merge button 185 is not received (NO at Step S108) or after Step S109, it is determined whether an analysis termination command is input (Step S110).

If the analysis termination command is not input (NO at Step S110) or if the display window 190 is hidden (Step S112), it is determined whether a specific annotation is selected (Step S113). The annotation may be selected by selecting a specific annotation number or a specific row in the annotation list 180 or by specifying a temporal position by operating the time zone 120b on the time axis 122 in the display region 120. If an annotation is selected (YES at Step S113), signal waveforms corresponding to a predetermined time including the temporal position of the selected annotation are displayed (Step S114).

In the displayed situation, it is determined whether the line 117 indicating a temporal position of a mark displayed in a highlighted manner is selected (Step S115). If the line 117 is selected (YES at Step S115), signal waveforms in a certain time range including the selected line are displayed in an enlarged manner (Step S116). A channel of the waveform displayed in the enlarged display region 200 corresponds to the sensor that is determined at Step S224. Here, it is not always necessary to display enlarged views of signal waveforms that are present near the mark displayed in a highlighted manner in the enlarged display region 200, but it may be possible to display enlarged views of signal waveforms of a different kind that are present at the same temporal position. For example, when a mark displayed in a highlighted manner is added to electroencephalography signal waveforms, it may be possible to display enlarged views of magnetoencephalography signal waveforms that are present at the same temporal position. Further, it may be possible to display enlarged views of signal waveforms that are acquired by channels in a certain range including a channel that has acquired the marked signal waveform, instead of displaying enlarged views of signal waveforms of all of the channels. In this case, it may be possible to determine a type of signal waveforms to be displayed in an enlarged manner or determine whether designation of a channel range is input or not.

Subsequently, it is determined whether the signal source estimation button 212 is pressed (Step S117). If the signal source estimation button 212 is pressed (YES at Step S117), calculation for estimating a signal source is performed. An estimation result is displayed on an MRI tomography screen and the estimation completion mark 182 is added to the annotation list 180 (Step S118). Further, information on the annotation in which the estimated signal source is reflected is additionally included in the measurement data on the patient, and stored (updated) in the server 40 or the like. Then, the process returns to Step S104.

As described above with reference to FIG. 44 and FIG. 45, if a signal source is not estimated, it is possible to view waveforms of a magnetoencephalography signal and a electroencephalography signal over a long period of time in the measurement time, so that it is possible to simplify analysis operation, such as identification of an affected area, on the waveforms.

Third Embodiment

A biological signal measurement system 1 according to a third embodiment will be described mainly in terms of a difference from the biological signal measurement system 1 according to the first embodiment. In the first embodiment, operation of changing a layout of the analysis screen in accordance with a result of a medical examination (including a medical interview) that is performed on a patient in advance and displaying the changed layout as an initial layout has been described. In the third embodiment, operation of changing a layout of the analysis screen in accordance with selection of a channel of a magnetoencephalography signal or selection of a montage pattern of an electroencephalography signal will be described. Meanwhile, an entire configuration of the biological signal measurement system 1 and hardware configurations and functional block configurations of an information processing apparatus 50 and a server 40 according to the third embodiment are the same as those described in the first embodiment.

Operation of Functional Blocks of Information Processing Apparatus

The functional block configuration and operation of the information processing apparatus 50 according to the third embodiment will be described with reference to FIG. 3 described earlier.

The setting unit 304 sets a layout table for associating one of a selection state of a channel of a magnetoencephalography signal and a selection state of a montage pattern of an electroencephalography signal with a layout content to be displayed in the analysis screen, in accordance with input operation received by the input unit 311, and stores the layout table in the storage unit 310.

The layout information acquiring unit 308 acquires information (one example of the determination information) indicating a specific condition for determining a layout of the analysis screen. Specifically, in the third embodiment, the layout information acquiring unit 308 acquires, as the information indicating the specific condition, information indicating the selection state of the channel of the magnetoencephalography signal or the selection state of the montage pattern of the electroencephalography signal. Here, each of the information indicating the selection state of the channel of the magnetoencephalography signal and the selection state of the montage pattern of the electroencephalography signal are information indicating a selection state of a biological signal (the magnetoencephalography signal, the electroencephalography signal, or the like) to be displayed on the analysis screen. Further, the channel of the magnetoencephalography signal is selected by, for example, selecting each of channels on the distribution maps 141 and 142 illustrated in FIG. 14 or selecting, from a combo box arranged near the distribution maps 141 and 142, a channel group constituted of a plurality of channels that are registered in advance. Furthermore, the montage pattern of the electroencephalography signal is selected by, for example, selecting a montage pattern that is registered in advance from a combo box arranged near the distribution map 130 illustrated in FIG. 14.

The layout determining unit 309 determines whether the information that indicates the selection state of the channel of the magnetoencephalography signal or the selection state of the montage pattern of the electroencephalography signal and that is acquired by the layout information acquiring unit 308 matches a "channel etc. selection state" defined in the layout table, which is stored in the storage unit 310 and in which the selection state and the layout content of the analysis screen are associated. Then, the layout determining unit 309 acquires a layout content corresponding to the information indicating the selection state of the channel of the magnetoencephalography signal or the selection state of the montage pattern of the electroencephalography signal, where the information is acquired by the layout information acquiring unit 308 and matches the "channel etc. selection condition" defined in the layout table, and determines the acquired layout content as a layout of the analysis screen.

Meanwhile, operation performed by the recording display control unit 301, the analysis display control unit 302, the merge display control unit 303, the analyzing unit 305, the communication unit 306, the sensor information acquiring unit 307, the storage unit 310, and the input unit 311 are the same as the operation described in the first embodiment.

Operation of Changing Layout of Display Contents of Analysis Screen

Figure 46:
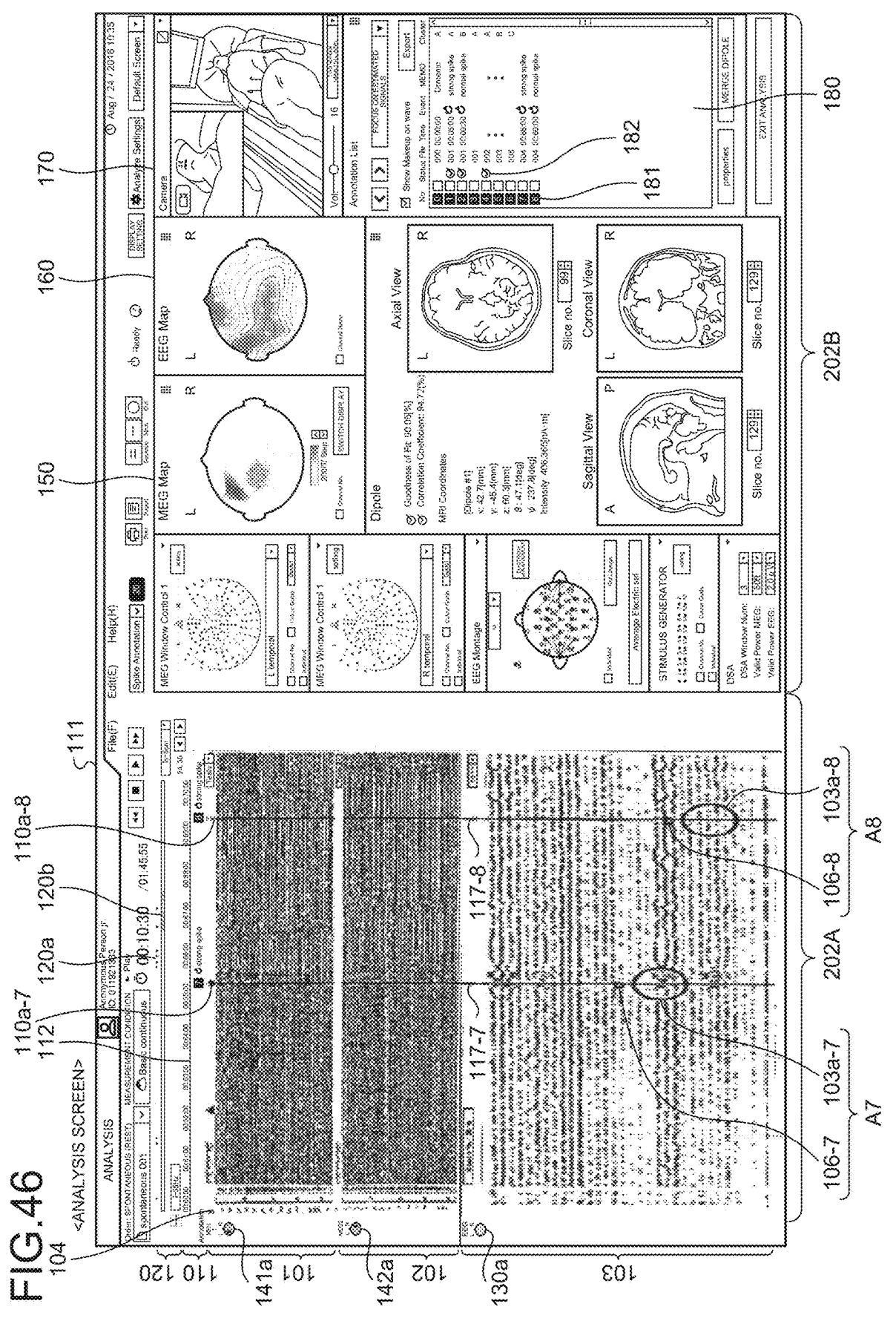
Figures 47, 48:
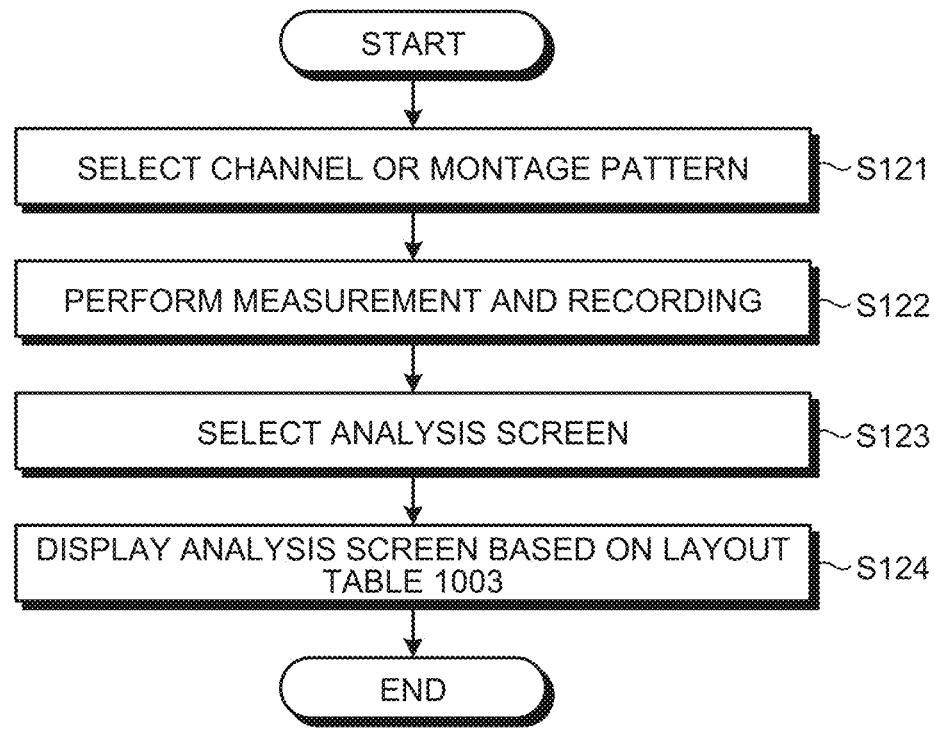
FIG. 47 is a diagram illustrating an example of a layout table of the third embodiment.
FIG. 48 is a flowchart illustrating operation of changing a layout of the analysis screen.

FIG. 46 is a diagram illustrating an example in which an electroencephalography signal waveform is enlarged in the analysis screen according to the third embodiment. FIG. 47 is a diagram illustrating an example of the layout table of the third embodiment. FIG. 48 is a flowchart illustrating operation of changing a layout of the analysis screen. Operation performed by the information processing apparatus 50 according to the third embodiment for changing a layout of display contents of the analysis screen will be described with reference to FIG. 46 to FIG. 48.

As described above, when information is measured by magnetoencephalograph or electroencephalograph or related information is to be displayed, in some cases, an appropriate mode of displaying the information in the analysis screen may be substantially determined depending on, for example, the selection state of the channel of the magnetoencephalography signal or the selection state of the montage pattern of the electroencephalography signal. For example, if a different montage pattern is selected with respect to a montage pattern of a brain wave, the analysis display control unit 302 displays an enlarged view of the display region 103 in which the electroencephalography signal is displayed as illustrated in FIG. 46. With this operation, it is possible to save time and effort of setting an optimal or preferable layout after selecting a montage pattern. In this case, as illustrated in FIG. 46, the analysis display control unit 302 may display reduced views of the display regions 101 and 102 in which magnetoencephalography signals of a patient are displayed. Further, when displaying the display regions 101 and 102 in a reduced manner, it may be possible to display all of signals by reducing intervals between the signals corresponding to channels that are selected in the reduced images 141a and 142a, or may display only signals corresponding to channels after thinning the selected channels. Meanwhile, when it is desired to check the electroencephalography signal prior to the magnetoencephalography signals on the basis of a medical examination result, the analysis display control unit 302 may hide the display regions 101 and 102 in which the magnetoencephalography signals are displayed.

Details of the above-described operation of changing the layout of display contents of the analysis screen (for example, operation of displaying the display region 103 in an enlarged manner and displaying the display regions 101 and 102 in a reduced manner) depending on the selection state of the channel of the magnetoencephalography signal or the selection state of the montage pattern of the electroencephalography signal will be described below with reference to FIG. 47 and FIG. 48. First, the information processing apparatus 50 has a layout table for associating a type of the selection state of the channel of the magnetoencephalography signal or the selection state of the montage pattern of the electroencephalography signal with a type of the layout of the analysis screen. For example, as illustrated in FIG. 47, when a user (doctor or the like) of the analysis screen performs operation of inputting a selected channel or a selected montage pattern via the input unit 311, the setting unit 304 sets, in accordance with the input operation, a layout table 1003 (one example of the layout information) for associating the selection state of the channel of the magnetoencephalography signal or the selection state of the montage pattern of the electroencephalography signal with a layout content to be displayed in the analysis screen, and stores the layout table 1003 in the storage unit 310 (Step S121). In the example of the layout table 1003 illustrated in FIG. 47, for example, a layout content of "display a waveform of a montage pattern corresponding to a channel group (L)" is associated with a channel etc. selection condition of "select the channel group (L)". Meanwhile, while the layout table 1003 is described as information in a table format, embodiments are not limited to this example, and the layout table may be in any format as long as values in a plurality of fields of the layout table can be managed in an associated manner.

Subsequently, the doctor performs measurement and recording on a specific patient using the measurement recording screen illustrated in FIG. 6 (Step S122). Then, after performing measurement and recording on the specific patient, the user (doctor or the like) of the analysis screen selects and opens an analysis screen in the information processing apparatus 50 to analyze measurement data (a magnetoencephalography signal, an electroencephalography signal, and the like) on the specific patient (Step S123), and the layout information acquiring unit 308 acquires, as the information indicating the specific condition, the information indicating the selection state of the channel of the magnetoencephalography signal or the selection state of the montage pattern of the electroencephalography signal. The layout determining unit 309 determines whether the information that indicates the selection state of the channel of the magnetoencephalography signal or the selection state of the montage pattern of the electroencephalography signal and that is acquired by the layout information acquiring unit 308 matches a "channel etc. selection condition" that is defined in the layout table 1003 stored in the storage unit 310. Then, the layout determining unit 309 acquires, from the layout table 1003, a layout content corresponding to the information indicating the selection state of the channel of the magnetoencephalography signal or the selection state of the montage pattern of the electroencephalography signal, where the information is acquired by the layout information acquiring unit 308 and which matches the "channel etc. selection condition" defined in the layout table, and determines the acquired layout content as a layout of the analysis screen. The analysis display control unit 302 changes the layout from the current analysis screen in accordance with the layout content of the analysis screen determined by the layout determining unit 309, and displays the changed layout (Step S124).

In this manner, a layout of the analysis screen is changed depending on the selection state of the channel of the magnetoencephalography signal or the selection state of the montage pattern of the electroencephalography signal. With this configuration, it is possible to appropriately change the layout of information to be displayed, in accordance with the selection state of the channel of the magnetoencephalography signal or the selection state of the montage pattern of the electroencephalography signal (one example of the specific condition). Therefore, it is possible to save time and effort of manually changing the layout and display necessary information in an easily viewable manner depending on the selection state, so that it is possible to simplify operation of checking a state of an affected area.

Meanwhile, the details of the layout change described above are mere example, and embodiments are not limited to this example. For example, it may be possible to change a ratio between the display region 101 and the display region 102 depending on a ratio between the number of channels selected in the distribution map 141 and the number of channels selected in the distribution map 142. With this configuration, it is possible to check waveforms of magnetoencephalography signals corresponding to the channels selected in the distribution maps 141 and 142 in the entirely same state, so that it is possible to simplify analysis operation, such as identification of an affected area, on the waveforms.

Fourth Embodiment

A biological signal measurement system 1 according to a fourth embodiment will be described mainly in terms of a difference from the biological signal measurement system 1 according to the first embodiment. In the first embodiment, operation of changing a layout of the analysis screen in accordance with a result of a medical examination (including a medical interview) that is performed on a patient in advance and displaying the changed layout as an initial layout has been described. In the fourth embodiment, operation of changing a layout of the analysis screen in accordance with role information indicating a specialty or the like of a user and displaying the changed layout as an initial layout will be described. Meanwhile, an entire configuration of the biological signal measurement system 1 and hardware configurations and functional block configurations of an information processing apparatus 50 and a server 40 according to the fourth embodiment are the same as those described in the first embodiment.

Operation of Functional Blocks of Information Processing Apparatus

The functional block configuration and operation of the information processing apparatus 50 according to the fourth embodiment will be described with reference to FIG. 3 described earlier.

The layout information acquiring unit 308 acquires information indicating a specific condition for determining a layout of the analysis screen (one example of determination information). Specifically, in the fourth embodiment, the layout information acquiring unit 308 acquires role information indicating a specialty or the like of a user (doctor or the like) of the analysis screen from the server 40 via the communication unit 306. Meanwhile, as a method of acquiring the role information by the layout information acquiring unit 308, the following method may be adopted, for example. User information (including a login ID, a password, and the like) is referred to when a user of the analysis screen logs into an application that controls the information processing apparatus 50 or the analysis screen. It is sufficient to manage the user information in the server 40, for example. It is assumed that, in the user information, the user is associated with not only a login ID and a password, but also the role information. In this case, the layout information acquiring unit 308 is able to acquire the role information from the user information on the user who has logged in the application that controls the information processing apparatus 50 or the analysis screen.

The layout determining unit 309 refers to a layout table, which is stored in the storage unit 310 (to be described later) and in which the role information indicating a specialty or the like of the user and the layout content of the analysis screen are associated, acquires a layout content corresponding to the role information that is acquired by the layout information acquiring unit 308 and that serves as the information indicating the specific condition, and determines the acquired layout content as a layout of the analysis screen.

Meanwhile, operation performed by the recording display control unit 301, the analysis display control unit 302, the merge display control unit 303, the analyzing unit 305, the communication unit 306, the sensor information acquiring unit 307, the storage unit 310, and the input unit 311 are the same as the operation described in the first embodiment.

Operation of Changing Layout of Display Contents of Analysis Screen

FIG. 49 is a diagram illustrating an example of the layout table of the fourth embodiment. FIG. 50 is a flowchart illustrating operation of changing a layout of the analysis screen. Operation performed by the information processing apparatus 50 according to the fourth embodiment for changing a layout of display contents of the analysis screen will be described below with reference to of FIG. 49 and FIG. 50.

As described above, when information measured by magnetoencephalograph or electroencephalograph or related information is to be displayed, in some cases, an appropriate mode of displaying the information in the analysis screen may be substantially determined depending on, for example, the role information indicating a specialty or the like of a user. For example, if a user of the analysis screen is a brain surgeon, the analysis display control unit 302 displays the display window 190 containing an MRI tomography image in an enlarged manner as illustrated in FIG. 40. In this case, if an estimated signal source is present, the analysis display control unit 302 may display, in a superimposed manner, the estimated signal source on the tomography image displayed in the display window 190. Further, as illustrated in FIG. 40 as described above, the analysis display control unit 302 may hide the enlarged display region 200 as a result of displaying the display window 190 in an enlarged manner.

Details of the above-described operation of changing the layout of display contents of the analysis screen (for example, operation of displaying the display window 190 in an enlarged manner as described above) depending on the role information indicating the specialty or the like of the user will be described below. First, a user of the analysis screen sets a layout table for associating a type of the role information with a type of the layout of the analysis screen. For example, as illustrated in FIG. 49, when a user (doctor or the like) of the analysis screen performs input operation on the input unit 311, the setting unit 304 sets, in accordance with the input operation, a layout table 1004 (one example of the layout information) for associating the role information with a layout content to be displayed in the analysis screen, and stores the layout table 1004 in the storage unit 310. In the example of the layout table 1004 illustrated in FIG. 49, for example, a layout content of "enlarge a waveform and hide an MRI tomography image" is associated with role information of an "epilepsy doctor". Meanwhile, while the layout table 1004 is described as information in a table format, embodiments are not limited to this example, and the layout table may be in any format as long as values in a plurality of fields of the layout table can be managed in an associated manner.

When the user (doctor or the like) of the analysis screen opens an analysis screen in the information processing apparatus 50 to analyze measurement data on a specific patient, the layout information acquiring unit 308 acquires the role information indicating the specialty or the like of the user from the server 40 via the communication unit 306. The layout determining unit 309 refers to the layout table 1004 stored in the storage unit 310, acquires a layout content that corresponds to the role information acquired by the layout information acquiring unit 308, and determines the acquired layout content as a layout of the analysis screen. The analysis display control unit 302 constructs an initial layout by changing the layout of the analysis screen that has a basic layout as illustrated in FIG. 12 etc., in accordance with the layout content of the analysis screen determined by the layout determining unit 309, and displays the initial layout.

In this manner, the layout of the analysis screen is changed depending on the role information indicating the specialty or the like of the user. With this configuration, it is possible to appropriately change the layout of information to be displayed, in accordance with the role information indicating the specialty or the like of the user (one example of the specific condition). Therefore, it is possible to save time and effort of manually changing the layout suitable for the user each time and display necessary information in an easily viewable manner depending on the role information, so that is possible to simplify operation of checking a state of an affected area.

The above-described operation will be explained with reference to FIG. 50. The operation illustrated in FIG. 50 is an example for selecting the analysis screen corresponding to the specialty of the user as illustrated in FIG. 49 and reflecting a medical examination result in the analysis screen. For example, when a user (doctor or the like) of the analysis screen performs operation of inputting a medical examination result (diagnosis result) via the input unit 311 illustrated in FIG. 3 (Step S141), the setting unit 304 sets, in accordance with the input operation, the layout table 1001 (see FIG. 19) for associating the medical examination result (including the medical interview result) with a layout content to be displayed in the analysis screen, and stores the layout table 1001 in the storage unit 310. Further, when the doctor performs a medical examination on the patient before performing measurement and recording using the measurement recording screen illustrated in FIG. 6, the doctor reflects information on a medical examination result (including a medical interview result) in the patient information that is about the patient and that is stored in the storage unit 353 of the server 40.

Then, after performing measurement and recording on the specific patient (Step S142), the user (doctor or the like) of the analysis screen selects and opens an analysis screen in the information processing apparatus 50 to analyze measurement data (a magnetoencephalography signal, an electroencephalography signal, and the like) on the specific patient (Step S143), and the layout information acquiring unit 308 acquires the role information indicating the specialty or the like of the user from the server 40 via the communication unit 306. Further, the layout information acquiring unit 308 acquires the patient information (including the medical examination result) associated with the measurement data of the patient from the server 40 via the communication unit 306. The layout determining unit 309 acquires a layout content corresponding to the role information acquired by the layout information acquiring unit 308 (Step S144), acquires a layout content corresponding to the medical examination result in the patient information acquired by the layout information acquiring unit 308, and determines a layout of the analysis screen by combining the acquired layout contents (Step S145).

Meanwhile, it is of course possible for the user to manually change, through input operation, a layout of the initially-displayed analysis screen for which the layout has been changed. Further, the details of the layout change described above are mere example, and embodiments are not limited to this example.

Moreover, in each of the embodiments as described above, when at least any of the functional units of the biological signal measurement system 1 is implemented by executing a program, the program is provided by being incorporated in a ROM or the like in advance. Furthermore, in each of the embodiments as described above, the program executed by the biological signal measurement system 1 may be provided by being recorded in a computer-readable recording medium, such as a compact disc-ROM (CD-ROM), a flexible disk (FD), a compact disc-recordable (CD-R), or a digital versatile disk (DVD), in a computer-installable or computer-executable file format. Moreover, in each of the embodiments as described above, the program executed by the biological signal measurement system 1 may be stored in a computer connected to a network, such as the Internet, and may be provided by being downloaded via the network. Furthermore, in each of the embodiments as described above, the program executed by the biological signal measurement system 1 may be provided or distributed via a network, such as the Internet. Moreover, in each of the embodiments as described above, the program executed by the biological signal measurement system 1 has a module structure including at least any of the functional units as described above. As actual hardware, the CPU 501 reads the program from the above-described storage device (for example, the ROM 503, the auxiliary storage device 504, or the like) and executes the program, so that each of the functional units as described above is loaded and generated on a main storage device (for example, the RAM 502).

According to an embodiment of the present invention, it is possible to appropriately change a layout of information to be displayed, depending on a specific condition.

The above-described embodiments are illustrative and do not limit the present invention. Thus, numerous additional modifications and variations are possible in light of the above teachings. For example, at least one element of different illustrative and exemplary embodiments herein may be combined with each other or substituted for each other within the scope of this disclosure and appended claims. Further, features of components of the embodiments, such as the number, the position, and the shape are not limited the embodiments and thus may be preferably set. It is therefore to be understood that within the scope of the appended claims, the disclosure of the present invention may be practiced otherwise than as specifically described herein.

The method steps, processes, or operations described herein are not to be construed as necessarily requiring their performance in the particular order discussed or illustrated, unless specifically identified as an order of performance or clearly identified through the context. It is also to be understood that additional or alternative steps may be employed.

Further, any of the above-described apparatus, devices or units can be implemented as a hardware apparatus, such as a special-purpose circuit or device, or as a hardware/software combination, such as a processor executing a software program.

Further, as described above, any one of the above-described and other methods of the present invention may be embodied in the form of a computer program stored in any kind of storage medium. Examples of storage mediums include, but are not limited to, flexible disk, hard disk, optical discs, magneto-optical discs, magnetic tapes, non-volatile memory, semiconductor memory, read-only-memory (ROM), etc.

Alternatively, any one of the above-described and other methods of the present invention may be implemented by an application specific integrated circuit (ASIC), a digital signal processor (DSP) or a field programmable gate array (FPGA), prepared by interconnecting an appropriate network of conventional component circuits or by a combination thereof with one or more conventional general purpose microprocessors or signal processors programmed accordingly.

Each of the functions of the described embodiments may be implemented by one or more processing circuits or circuitry. Processing circuitry includes a programmed processor, as a processor includes circuitry. A processing circuit also includes devices such as an application specific integrated circuit (ASIC), digital signal processor (DSP), field programmable gate array (FPGA) and conventional circuit components arranged to perform the recited functions.

What is claimed is:

1. An information processing apparatus comprising:
processing circuitry configured to,
receive a plurality of biological signals associated with a patient from a plurality of measurement devices, the plurality of measurement devices including measurement devices of at least two different measurement device types;
acquire determination information for displaying information related to one or more biological signals of the plurality of biological signals, the determination information including at least patient information corresponding to the patient and role information corresponding to a user, the role information indicating a medical specialty of the user;

determine an analysis screen display layout corresponding to the acquired determination information;

change a display layout of the analysis screen in accordance with the determined display layout, the changing the display layout of the analysis screen including displaying a subset of the plurality of biological signals based on the acquired determination information and the measurement device types of the corresponding measurement devices;

receive an estimation user input associated with a selected annotation on at least one biological signal from the plurality of biological signals displayed on the analysis screen; and estimate at least one signal source corresponding to the annotation in response to the received estimation user input.

2. The information processing apparatus according to claim 1, wherein the processing circuitry is further configured to:

set layout information for associating determination information and the display layout of the analysis screen;

acquire the analysis screen display layout corresponding to the acquired determination information from the layout information; and determine the acquired display layout as the display layout of the analysis screen.

3. The information processing apparatus according to claim 1, wherein the processing circuitry is further configured to:

determine, as the display layout corresponding to the determination information, the analysis screen display layout for displaying, in an enlarged manner, at least any piece of information on the one or more biological signals, the at least any piece information corresponding to the determination information.

4. The information processing apparatus according to claim 1, wherein the processing circuitry is further configured to:

determine, as the display layout corresponding to the determination information, a display layout for displaying, in a reduced manner, or hiding at least any piece of information on the one or more biological signals, the at least any piece information not corresponding to the determination information.

5. The information processing apparatus according to claim 1, wherein the processing circuitry is further configured to:

change an initial layout of the analysis screen in accordance with the determined display layout.

6. The information processing apparatus according to claim 5, wherein the processing circuitry is further configured to:

acquire, as the determination information, the patient information including a medical examination result on the patient;

determine the display layout corresponding to the medical examination result; and change an initial layout of the analysis screen in accordance with the determined display layout that corresponds to the medical examination result.

7. The information processing apparatus according to claim 6, wherein the processing circuitry is further configured to:

acquire the patient information including, as the medical examination result, a medical interview result on the patient.

8. The information processing apparatus according to claim 1, wherein the processing circuitry is further configured to:

analyze the one or more biological signals;

acquire, as the determination information, information on an analysis result of the analyzing the one or more biological signals; and determine the display layout corresponding to the information on the analysis result.

9. The information processing apparatus according to claim 8, wherein the processing circuitry is further configured to:

acquire, as the information on the analysis result, information indicating an estimation state of one or more signal sources corresponding to a part of the one or more biological signals; and determine the display layout corresponding to the information indicating the estimation state of the one or more signal sources.

10. The information processing apparatus according to claim 1, wherein the processing circuitry is further configured to:

acquire, as the determination information, information indicating a selection state of whether any of the one or more biological signals is to be displayed in the analysis screen; and determine the display layout corresponding to the information indicating the selection state.

11. A biological signal measurement system comprising:

the plurality of measurement devices each configured to measure the one or more biological signals from a subject; and the information processing apparatus according to claim 1.

12. The information processing apparatus according to claim 1, wherein the analysis screen display layout includes a plurality of graphical user interface (GUI) windows, each of the plurality of GUI windows corresponding to one of the at least two different measurement device types; and the processing circuitry is further configured to change the display layout of the analysis screen by reducing a number of GUI windows included in the display layout based on the acquired determination information and the measurement device types of the corresponding measurement devices.

13. The information processing apparatus according to claim 1, wherein the at least two different measurement device types includes at least two of a magnetoencephalography (MEG) measurement device, an electroencephalography (EEG) measurement device, an electrocardiogram (EKG) measurement device, a magnetic resonance imaging (MRI) device, or any combinations thereof.

14. The information processing apparatus according to claim 1, wherein the processing circuitry is further configured to:

receive at least one video signal associated with the patient from at least one camera; and change the display layout of the analysis screen to include the received at least one video signal.

15. The information processing apparatus according to claim 1, wherein the processing circuitry is further configured to:

change the display layout of the analysis screen to include at least one window wherein at least one received biological signal of the received plurality of biological signals is superimposed on a biological tomography image corresponding to the patient.

16. The information processing apparatus according to claim 1, wherein the processing circuitry is further configured to:
   superimpose the estimated signal source on at least one biological tomography image corresponding to the patient; and
   display the superimposed estimated signal source on the analysis screen.

17. The information processing apparatus according to claim 16, wherein the estimated signal source is an estimated dipole result.

18. The information processing apparatus according to claim 17, wherein the processing circuitry is further configured to:
   superimpose the at least one estimated signal source on a plurality of slices of biological tomography images, the plurality of slices of biological tomography images corresponding to a three-dimensional position of the at least one estimated signal source; and
   display the plurality of slices of biological tomography images corresponding to the patient on the analysis screen.

19. An information processing method comprising:
   receiving a plurality of biological signals associated with a patient from a plurality of measurement devices, the plurality of measurement devices including measurement devices of at least two different measurement device types;
   acquiring determination information for displaying information related to one or more biological signals of the plurality of biological signals, the determination information including at least patient information corresponding to the patient and role information corresponding to a user, the role information indicating a medical specialty of the user;
   determining an analysis screen display layout corresponding to the acquired determination information;
   changing a display layout of the analysis screen in accordance with the determined display layout, the changing the display layout of the analysis screen including displaying a subset of the plurality of biological signals based on the acquired determination information and the measurement device types of the corresponding measurement devices;
   receive an estimation user input associated with a selected annotation on at least one biological signal from the plurality of biological signals displayed on the analysis screen; and
   estimate at least one signal source corresponding to the annotation in response to the received estimation user input.

20. A non-transitory computer-readable medium including programmed instructions that cause a computer to execute:
   receiving a plurality of biological signals associated with a patient from a plurality of measurement devices, the plurality of measurement devices including measurement devices of at least two different measurement device types;
   acquiring determination information for displaying information related to one or more biological signals of the plurality of biological signals, the determination information including at least patient information corresponding to the patient and role information corresponding to a user, the role information indicating a medical specialty of the user;
   determining an analysis screen display layout corresponding to the acquired determination information;
   changing a display layout of the analysis screen in accordance with the determined display layout, the changing the display layout of the analysis screen including displaying a subset of the plurality of biological signals based on the acquired determination information and the measurement device types of the corresponding measurement devices;
   receive an estimation user input associated with a selected annotation on at least one biological signal from the plurality of biological signals displayed on the analysis screen; and
   estimate at least one signal source corresponding to the annotation in response to the received estimation user input.

* * * * *